US008021880B2

(12) United States Patent
Peters et al.

(10) Patent No.: US 8,021,880 B2
(45) Date of Patent: *Sep. 20, 2011

(54) PC5 AS A FACTOR IX PROPEPTIDE PROCESSING ENZYME

(75) Inventors: Robert T. Peters, West Roxbury, MA (US); Alan J. Bitonti, Acton, MA (US)

(73) Assignee: Syntonix Pharmaceuticals, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/841,072

(22) Filed: Jul. 21, 2010

(65) Prior Publication Data

US 2011/0053222 A1 Mar. 3, 2011

Related U.S. Application Data

(62) Division of application No. 12/489,391, filed on Jun. 22, 2009, now Pat. No. 7,795,400, which is a division of application No. 11/728,045, filed on Mar. 23, 2007, now Pat. No. 7,566,565.

(60) Provisional application No. 60/785,421, filed on Mar. 24, 2006.

(51) Int. Cl.
*C12N 15/00* (2006.01)
*C12N 5/00* (2006.01)

(52) U.S. Cl. ........................................ 435/325; 435/383

(58) Field of Classification Search ........................ None
See application file for complete search history.

(56) References Cited

U.S. PATENT DOCUMENTS

| | | | |
|---|---|---|---|
| 4,215,051 A | 7/1980 | Schroeder et al. | |
| 4,713,339 A | 12/1987 | Levinson et al. | |
| 4,981,952 A | 1/1991 | Yan | |
| 5,252,714 A | 10/1993 | Harris et al. | |
| 5,272,071 A | 12/1993 | Chappel | |
| 5,460,950 A | 10/1995 | Barr et al. | |
| 5,641,670 A | 6/1997 | Treco et al. | |
| 5,691,183 A | 11/1997 | Franzusoff et al. | |
| 5,714,583 A | 2/1998 | Foster et al. | |
| 5,733,761 A | 3/1998 | Treco et al. | |
| 5,807,706 A | 9/1998 | Carter et al. | |
| 5,840,529 A | 11/1998 | Seidah et al. | |
| 5,866,351 A | 2/1999 | Franzusoff et al. | |
| 5,910,573 A | 6/1999 | Plückthun et al. | |
| 5,935,815 A | 8/1999 | van de Ven et al. | |
| 5,981,216 A | 11/1999 | Kenten et al. | |
| 6,030,613 A | 2/2000 | Blumberg et al. | |
| 6,086,875 A | 7/2000 | Blumberg et al. | |
| 6,380,171 B1 | 4/2002 | Day et al. | |
| 6,485,726 B1 | 11/2002 | Blumberg et al. | |
| 7,566,565 B2 * | 7/2009 | Peters et al. | 435/325 |
| 7,795,400 B2 * | 9/2010 | Peters et al. | 530/384 |
| 2005/0032174 A1 | 2/2005 | Peters et al. | |

FOREIGN PATENT DOCUMENTS

| | | |
|---|---|---|
| EP | 0 154 316 A2 | 9/1985 |
| EP | 0 246 709 A1 | 11/1987 |
| EP | 0 401 384 A1 | 12/1990 |
| WO | WO 90/11354 A1 | 10/1990 |
| WO | WO 91/06666 A1 | 5/1991 |
| WO | WO 91/06667 A1 | 5/1991 |
| WO | WO 92/16221 A1 | 10/1992 |
| WO | WO 95/34326 A1 | 12/1995 |
| WO | WO 03/077834 A2 | 9/2003 |
| WO | WO 2004/101740 A2 | 11/2004 |
| WO | WO 2005/001025 A2 | 1/2005 |

OTHER PUBLICATIONS

Armour, K.L., "Recombinant human IgG molecules lacking Fcγ receptor I binding and monocyte triggering activities," *Eur. J. Immunol.* 29(8): 2613-2624, Wiley-VCH, Germany (1999).

Bitonti, A.J., et al., "Pulmonary delivery of an erythropoietin Fc fusion protein in non-human primates through an immunoglobulin transport pathway," *Proc. Natl. Acad. Sci. USA* 101(26): 9763-9768, National Academy of Sciences, United States (2004).

Brennan, M., et al., "Preparation of bispecific antibodies by chemical recombination of monoclonal immunoglobulin G1 fragments," *Science* 229(4708): 81-83, American Association for the Advancement of Science, United States (1985).

Brumeanu, T.D., et al., "Enzymatically Mediated Coupling of Peptides and IgGs to Form Vaccines," *Genetic Engineering News* 15(17): 16, Mary Ann Liebert, Inc., United States (1995).

Burmeister, W.P., et al., "Crystal structure of the complex of rat neonatal Fc receptor with Fc,"*Nature* 372(6504): 379-383, Nature Publishing Group, England (1994).

Chamow, S.M., et al., "Modification of CD4 immunoadhesin with monomethoxypoly (ethylene glycol) aldehyde via reductive alkylation," *Bioconjugate Chem.* 5(2): 133-140, American Chemical Society, United States (1994).

Dumont, J.A., et al., "Monomeric Fc fusions: impact on pharmacokinetic and biological activity of protein therapeutics," *Biodrugs* 20(3): 151-160, Adis International, New Zealand (2006).

Friend, P.J., et al., "Phase I study of an engineered aglycosylated humanized CD3 antibody in renal transplant rejection," *Transplantation* 68(11): 1625-1631, Lippincott Williams & Wilkins, United States (1999). Gill, S.C.& von Hippel, P.H., "Calculation of protein extinction coefficients from amino acid sequence data," *Anal. Biochem.* 182(2): 319-326, Academic Press, United States (1989)

Harrison, S., et al., "The manufacturing process for recombinant factor IX," *Semin. Hematol.* 35(2 Suppl . 2): 4-10, W.B. Saunders, United States (1998).

Kostelny, S.A., et al., "Formation of a bispecific antibody by the use of leucine zippers," *J. Immunol.* 148(5): 1547-1553, American Association of Immunologists, United States (1992).

Kurachi, S., et al., "Role of intron I in expression of the human factor IX gene," *J. Biol. Chem.* 270(10): 5276-5281, American Society for Biochemistry and Molecular Biology, United States (1995).

Logan, J. & Shark, T., "Adenovirus tripartite leader sequence enhances translation of mRNAs late after infection," *Proc. Natl. Acad. Sci. USA* 81(12): 3655-3659, National Academy of Sciences, United States (1984).

(Continued)

*Primary Examiner* — Suzanne M. Noakes

(74) *Attorney, Agent, or Firm* — Sterne, Kessler, Goldstein & Fox, P.L.L.C.

(57) ABSTRACT

Compositions and methods for preparing Factor IX, Factor IX-containing fusion proteins, and Factor IX-containing conjugates with processing of Factor IX propeptide by PC5, are provided. In one embodiment PC5 is used to process a precursor polypeptide for a Factor IX-Fc monomer-dimer hybrid.

23 Claims, 16 Drawing Sheets

OTHER PUBLICATIONS

Lusson, J., et al., "cDNA structure of the mouse and rat subtilisin/kexin-like PC5: a candidate proprotein convertase expressed in endocrine and nonendocrine cells," *Proc. Natl. Acad. Sci. USA 90*(14): 6691-6695, National Academy of Sciences, United States (1993).

Mackett, M., et al., "General method for production and selection of infectious vaccinia virus recombinants expressing foreign genes," *J. Virology 49*(3): 857-864, American Society for Microbiology, United States (1984).

Mackett, M., et al., "Vaccinia virus: a selectable eukaryotic cloning and expression vector," *Proc. Natl. Acad. Sci. USA 79*(23): 7415-7419, National Academy of Sciences, United States (1982).

MacLennan, D.H., et al., "Structure-function relationships in the $Ca^{2+}$-binding and translocation domain of SERCA1: physiological correlates in Brody disease," *Acta Physiol. Scand. Suppl. 163* (Suppl, 643): 55-67, Blackwell Scientific Publication, England (1998).

Malik, F., et al., "Polyethylene glycol (PEG)-modified granulocyte-macrophage colony-stimulating factor (GM-CSF) with conserved biological activity," *Exp. Hematol. 20*(8): 1028-1035, Elsevier Science Inc., Netherlands (1992).

Nakagawa, T., et al., "Identification and functional expression of a new member of the mammalian Kex2-like processing endoprotease family: its striking structural similarity to PACE4," *J. Biochem. 113*(2): 132-135, Oxford University Press, England (1993).

Nakayama, K., "Furin: a mammalian subtilisin/Kex2p-like endoprotease involved in processing of a wide variety of precursor proteins," *J. Biochem. 327*(Pt. 3): 625-635, Portland Press on behalf of the Biochemical Society, England (1997).

NCBI Entrez, GenBank Report, GenBank Accession No. AB050084, Entry Date Apr. 2002.

NCBI Entrez, GenBank Report, GenBank Accession No. NM_000133, Entry Date Jun. 2007.

NCBI Entrez, GenBank Report, GenBank Accession No. NM_006200, Entry Date Jun. 2007.

NCBI Entrez, GenBank Report, GenBank Accession No. NP_000124, Entry Date Jun. 2007.

NCBI Entrez, GenBank Report, GenBank Accession No. NP_006191, Entry Date Jun. 2007.

NCBI Entrez, GenBank Report, GenBank Accession No. Y14735, Entry Date Aug. 1998.

Neumann, E., et al., "Gene transfer into mouse lyoma cells by electroporation in high electric fields," *The EMBO J. 1*(7): 841-845, Nature Pub. Group, England (1982).

Panicali, D. & Paoletti, E., "Construction of poxviruses as cloning vectors: insertion of the thymidine kinase gene from herpes simplex virus into the DNA of infectious vaccinia virus," *Proc. Natl. Acad. Sci. USA 79*(16): 4927-4931, National Academy of Sciences, United States (1982).

Rehemtulla, A., et al., "PACE4 is a member of the mammalian propeptidase family that has overlapping but not identical substrate specificity to PACE," *Biochemistry 32*(43): 11586-11590, American Chemical Society, United States (1993).

Rockwell, N.C., et al., "Precursor processing by kex2/furin proteases," *Chem. Rev. 102*(12): 4525-4548, American Chemical Society, United States (2002).

Routledge, E.G., et al., "The effect of aglycosylation on the immunogenicity of a humanized therapeutic CD3 monoclonal antibody," *Transplantation 60*(8): 847-853, Lippincott Williams & Wilkins, United States (1995).

Rüther, U. & Müller-Hill, B., "Easy identification of cDNA clones," *The EMBO J. 2*(10): 1791-1794, Nature Pub. Group, England (1983).

Sasaki, N. & Sutoh, K., "Structure-mutation analysis of the ATPase site of *Dictyostelium discoideum* myosin II," *Adv. Biophys. 35*: 1-24, Japan Scientific Societies Press, Japan (1998).

Shields, R.L., et al., "High resolution mapping of the binding site on human IgG1 for FcγRI, FcγRII, and FcRn and design of IgG1 variants with improved binding to the FcγR," *J. Biol. Chem. 276*(9): 6591-6604, American Society for Biochemistry and Molecular Biology, United States (2001).

Simonsen, C.C. & Levinson, A.D., "Isolation and expression of an altered mouse dihydrofolate reductase cDNA," Proc. Natl. Acad. Sci. USA 80(9): 2495-2499, National Academy of Sciences, United States (1983).

Smith, G.E., et al., "Molecular engineering of the *Autographa californica* Nuclear polyhedrosis virus genome: deletion mutations within the polyhedrin gene," *J. Virol. 46*(2): 584-593, American Society for Microbiology, United States (1983).

Story, C.M., et al., "A major histocompatibility complex Class I-like Fc receptor cloned from human placenta: possible role in transfer of immunoglobulin G from mother to fetus," *J. Exp. Med. 180*(6): 2377-2381, Rockefeller University Press, United States (1994).

van den Ouweland, A.M., et al., "Structural homology between the human *fur* gene product and the subtilisn-like protease encoded by yeast KEX2," *Nucl. Acids Res. 18*(3): 664 (1990); Erratum in: *Nucleic Acids Res. 18*: 1332, Oxford University Press, England (1990).

Ward, E.S. & Ghetie, V., "The effector functions of immunoglobulins: implications for therapy," *Ther. Immunol. 2*(2): 77-94, Blackwell Scientific Publications, England (1995).

Wasley, L.C. et al., "PACE/Furin Can Process the Vitamin K-dependent Pro-factor IX Precursor within the Secretory Pathway," *J. Biol. Chem. 268*(12): 8458-8465, American Society for Biochemistry and Molecular Biology, United States (1993).

Wigler, M., et al., "Biochemical transfer of single-copy eucaryotic genes using total cellular DNA as donor," *Cell 14*(3): 725-731, Cell Press, United States (1978).

Yan, S.B., "Review of conformation-specific affinity purification methods for plasma vitamin K-dependent proteins," *J. Mol. Recognit. 9*(3): 211-218, John Wiley & Sons, England (1996).

International Search Report for International Application No. PCT/US2007/007252, United States Patent and Trademark Office, U.S.A., mailed on May 11, 2007.

The Written Opinion of the International Searching Authority for International Application No. PCT/US2007/007252, United States Patent and Trademark Office, U.S.A., mailed on May 11, 2007.

\* cited by examiner

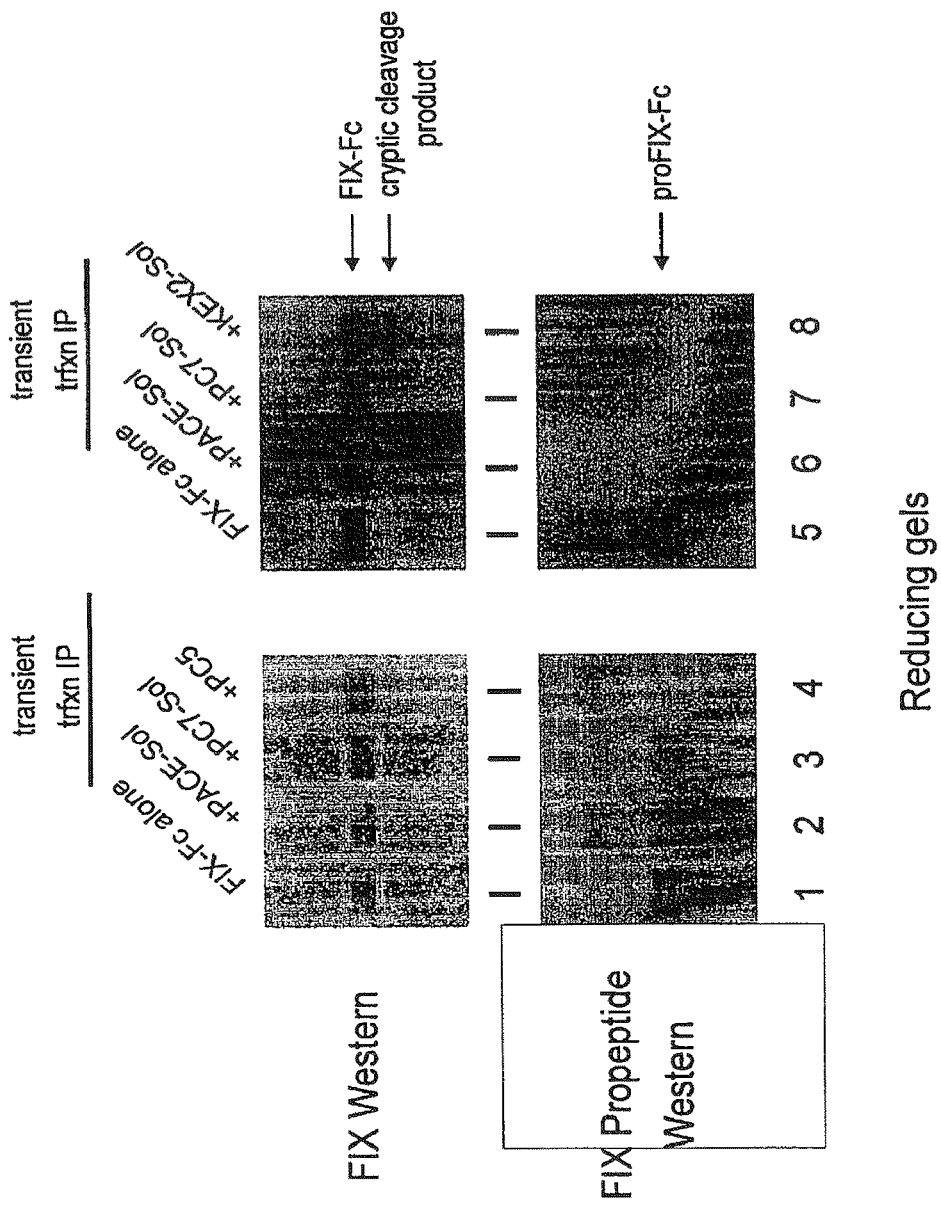
Fig 4: CHO transient

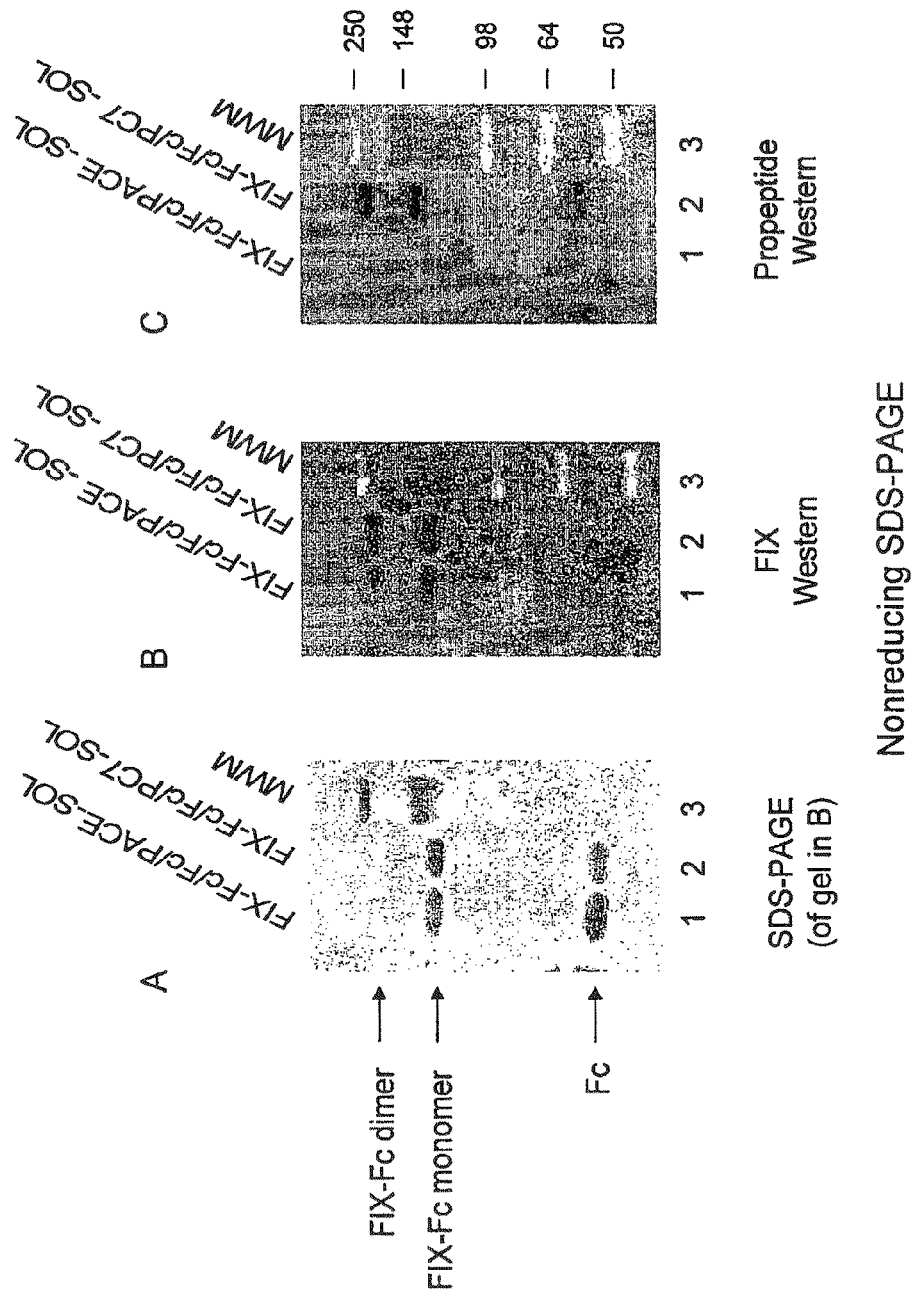

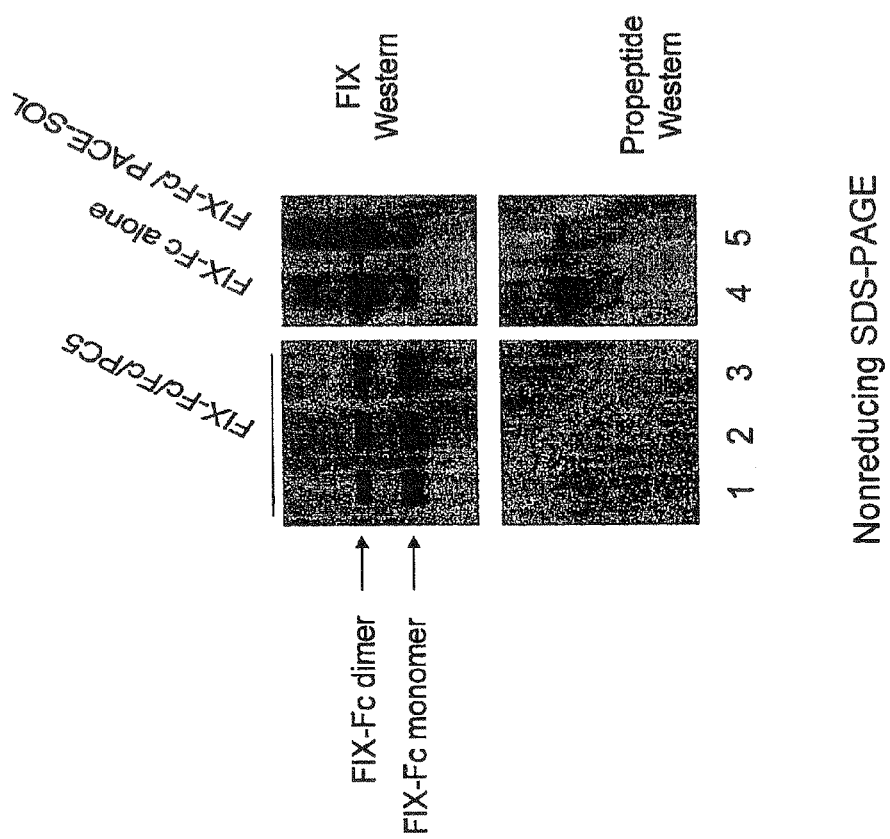
Fig 6: CHO stable (cont.)

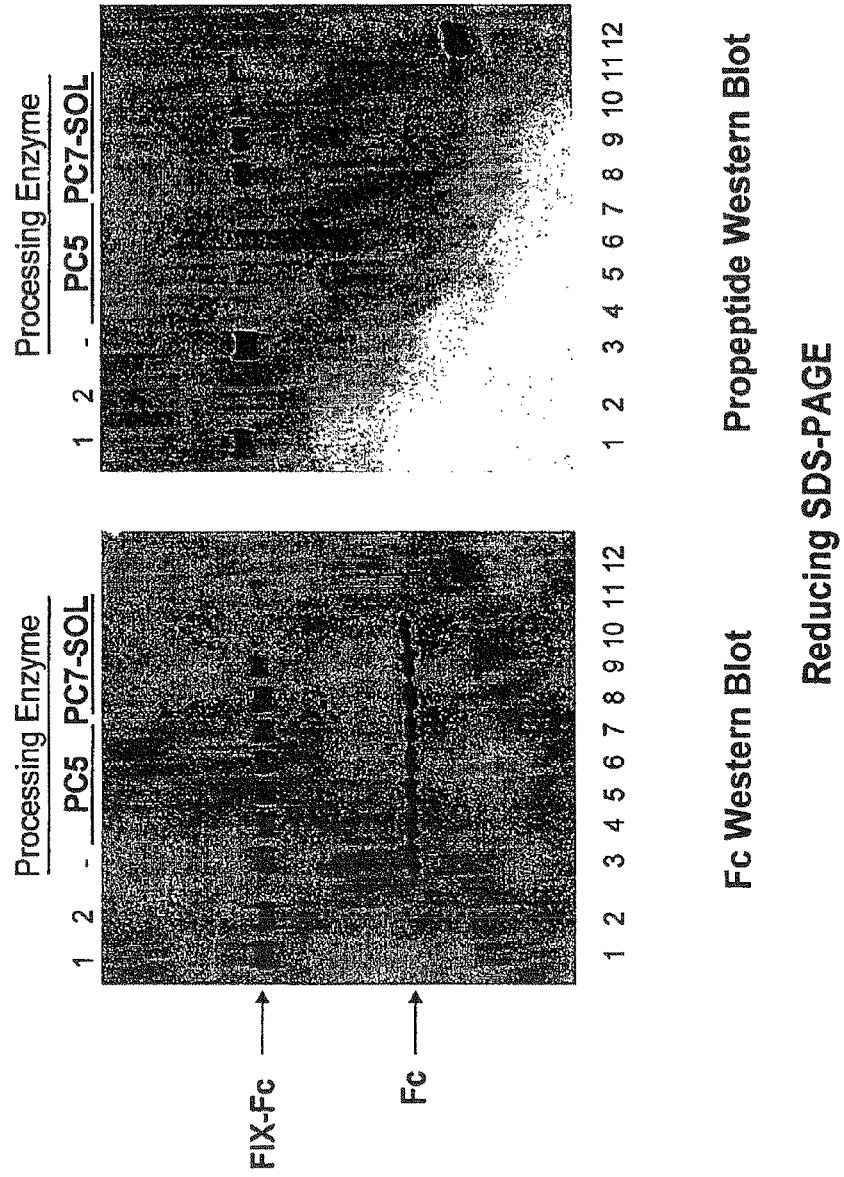
Fig 7: HEK transient
Lane 1 = CHO FIX-Fc/ no processing enzyme
Lane 2 = CHO FIX-Fc/PACE -SOL

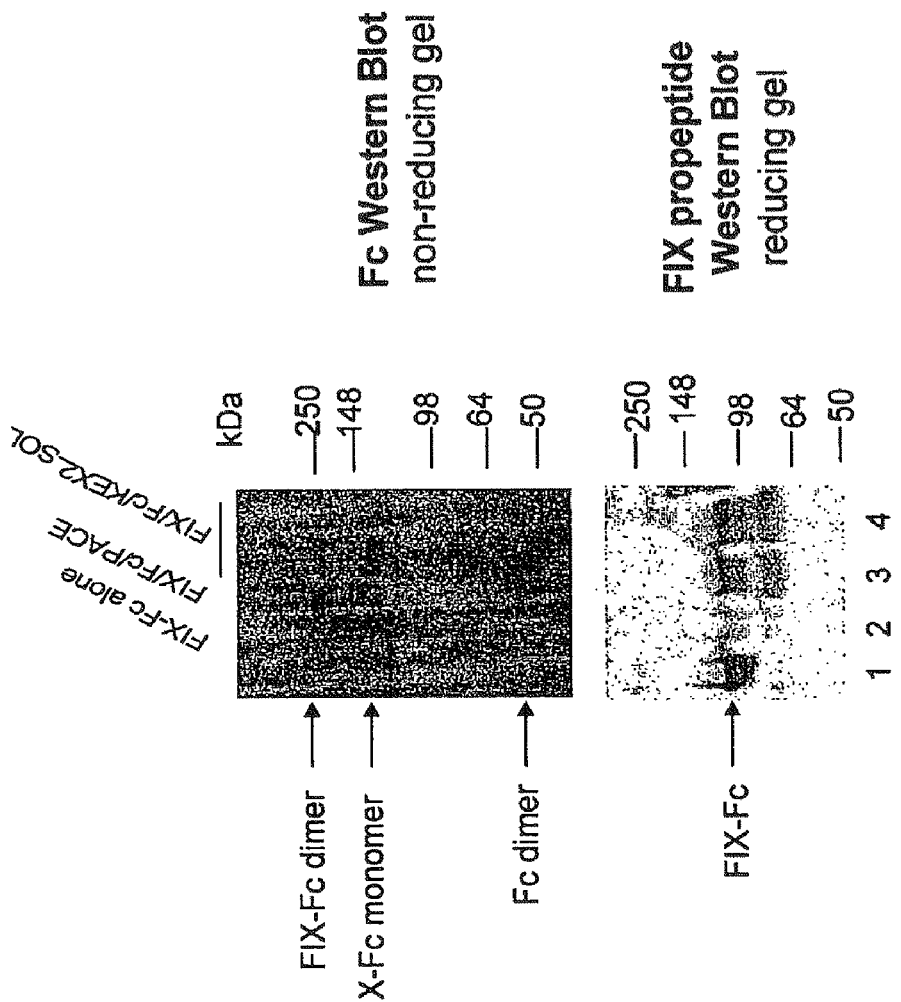
Fig 8: HEK transient (cont.)

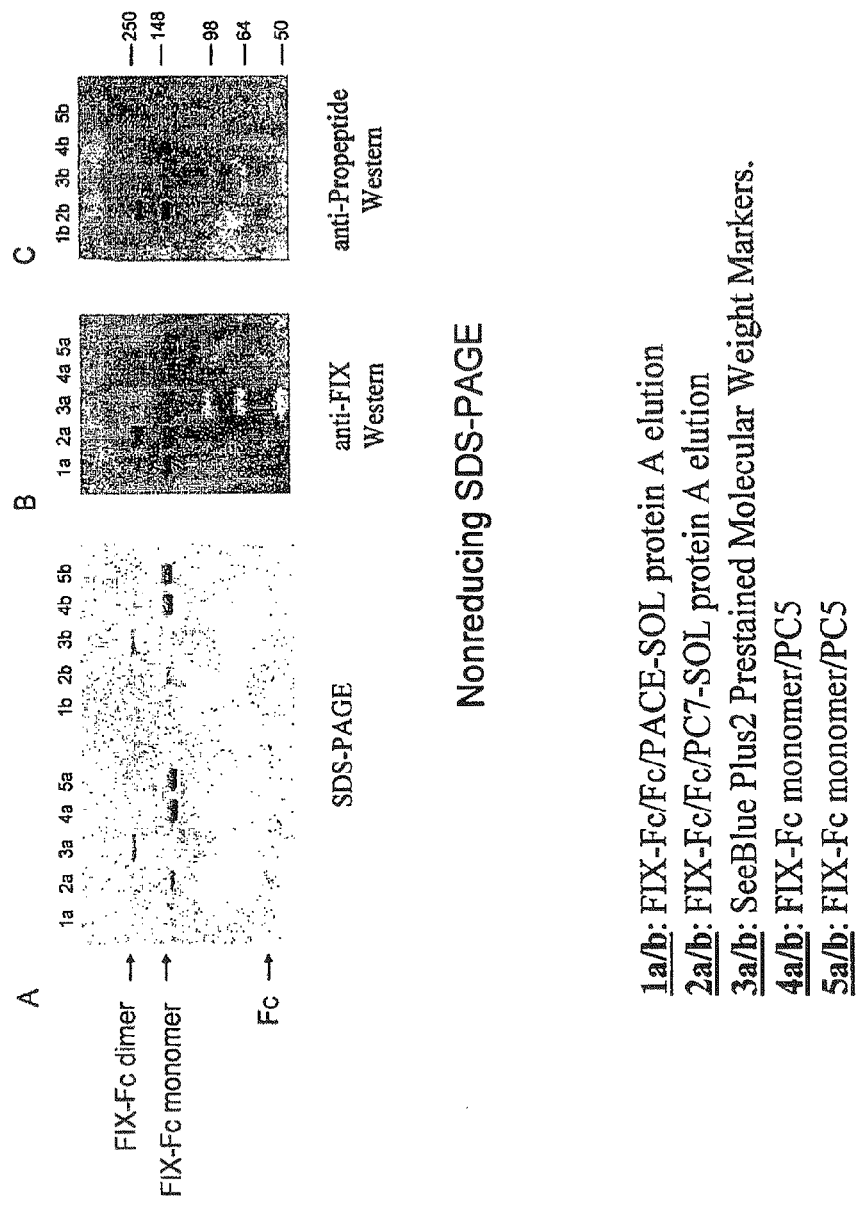
Fig 9: HEK stable

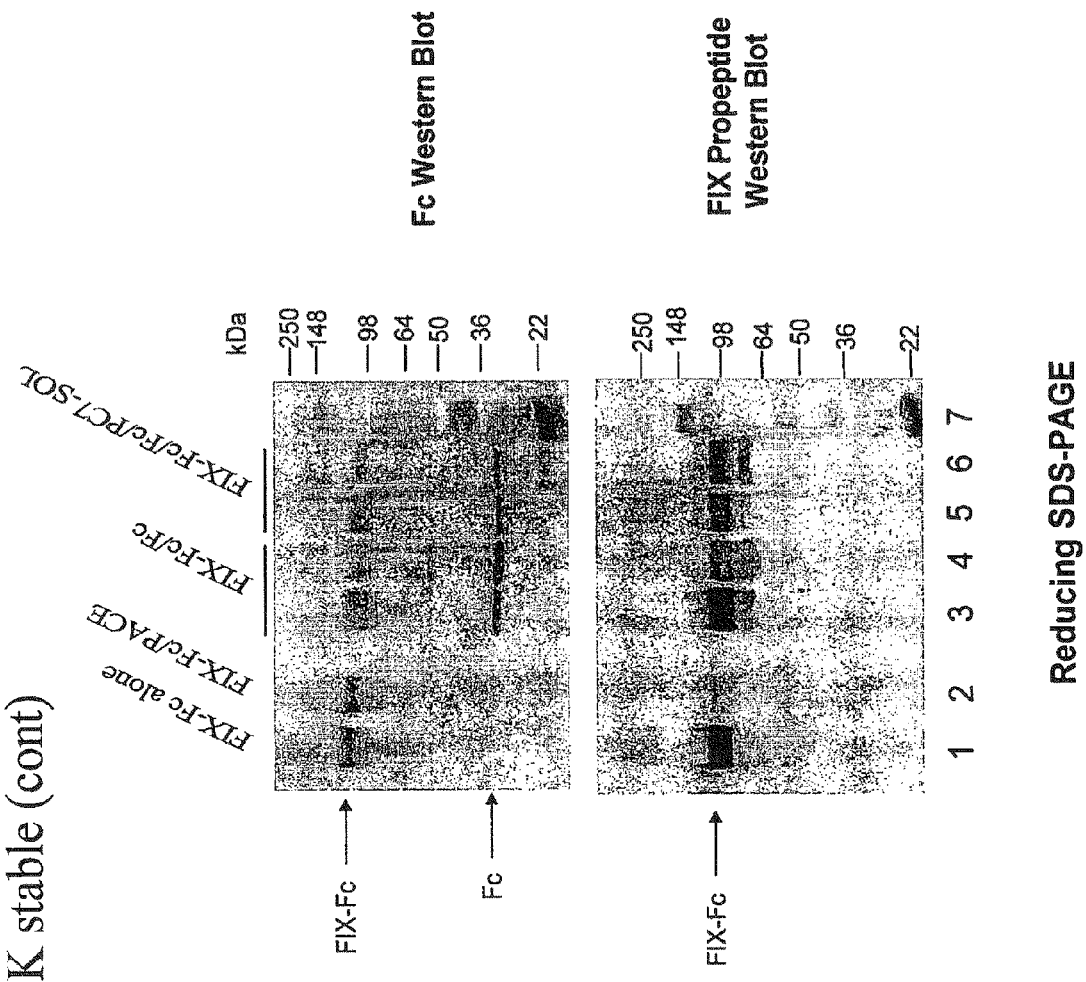
Fig 10: HEK stable (cont)

PC5 AS A FACTOR IX PROPEPTIDE PROCESSING ENZYME

RELATED APPLICATION

This application is a Divisional of U.S. application Ser. No. 12/489,391, filed Jun. 22, 2009 and issued Sep. 14, 2010 as U.S. Pat. No. 7,795,400, which is a Divisional of U.S. application Ser. No. 11/728,045, filed Mar. 23, 2007 and issued Jul. 28, 2009 as U.S. Pat. No. 7,566,565, which claims the benefit of U.S. Provisional Application No. 60/785,421, filed Mar. 24, 2006, the entire content of which is incorporated herein by reference.

BACKGROUND OF THE INVENTION

Factor IX (FIX) is a single-chain, 55 kDa zymogen of a serine protease encoded on the X chromosome in humans that is an important component of the intrinsic pathway of the blood coagulation cascade. Deficiency of functional FIX causes hemophilia B, also known as Christmas disease. Hemophilia B is reported to occur in 1 in 100,000 male births and, when untreated, is associated with severe and chronic morbidity resulting from uncontrolled bleeding into muscles, joints, and body cavities following injury. Until recently, treatments for FIX deficiency have included administration of natural FIX prepared from plasma derived from blood donor pools. Such treatments carry attendant risks of infection with blood-borne viruses including human immunodeficiency virus (HIV) and hepatitis C virus (HCV), as well as unwanted thrombosis and embolism. More recently, a preparation of recombinant FIX (BeneFIX®, Wyeth) became commercially available.

Certain posttranslational modifications are required for normal FIX activity. Fix is expressed as a precursor polypeptide that requires posttranslational processing to yield mature FIX. In particular, the precursor polypeptide of FIX requires vitamin K-dependent gamma carboxylation of certain glutamic acid residues in the so-called gamma-carboxyglutamate (Gla) domain and cleavage of propeptide (see FIG. 1). The propeptide is an 18-amino acid residue sequence N-terminal to the Gla domain. The propeptide binds vitamin K-dependent gamma carboxylase and then, in vivo, is cleaved from the precursor polypeptide of FIX by an endogenous protease, most likely PACE (paired basic amino acid cleaving enzyme), also known as furin and PCSK3. Without the vitamin K-dependent gamma carboxylation, the Gla domain is unable to bind calcium to assume the correct conformation necessary to anchor the protein to negatively charged phospholipid surfaces, thereby rendering Factor IX nonfunctional. Inhibition of vitamin K-dependent carboxylation by vitamin K antagonists such as warfarin is a common form of anticoagulant therapy. Even if it is carboxylated, the Gla domain also depends on cleavage of the propeptide for proper function, since retained propeptide interferes with conformational changes of the Gla domain necessary for optimal binding to calcium and phospholipid. Thus required post-translational modifications of the precursor polypeptide of FIX include both gamma carboxylation of certain glutamic acid residues by vitamin K-dependent gamma carboxylase and cleavage of the FIX propeptide, most likely by PACE, to yield mature FIX.

Mature FIX must be activated by activated Factor XI to yield Factor IXa. In the intrinsic pathway, FIX associates with a complex with activated Factor VIII, Factor X, calcium, and phospholipid, wherein FIX is activated by Factor XIa, and then Factor IXa in turn activates Factor X in concert with activated Factor VIII. Alternatively, Factors IX and X can both be activated by Factor VIIa complexed with lipidated Tissue Factor, which has been generated via the extrinsic pathway. Factor Xa then participates in the final common pathway whereby prothrombin is converted to thrombin, which in turn converts fibrinogen to fibrin.

Until now, in vitro post-translational processing of the precursor polypeptide of FIX, consistent with what was known about in vivo processing, has relied on PACE to effect cleavage of FIX propeptide. PACE is a member of a family of at least a half dozen mammalian subtilisin/Kex2p-like serine proteases known as proprotein convertases (PCs). PACE was found using sequence homology to KEX2, an enzyme in the yeast *Saccharomyces cerevisiae* and the first to be identified as an endoprotease involved in precursor processing. Subsequently other PC family members have been identified and found to have varying degrees of sequence identity and different substrate specificities.

EP 0246709 describes partial cDNA and amino acid sequences of furin (i.e., PACE).

Complete cDNA and amino acid sequences of human furin (i.e., PACE) were published in 1990. Van den Ouweland A M et al. (1990) *Nucleic Acids Res.* 18:664; Erratum in: *Nucleic Acids Res.* 18:1332 (1990).

U.S. Pat. No. 5,460,950, issued to Barr et al., describes recombinant PACE and the coexpression of PACE with a substrate precursor polypeptide of a heterologous protein to improve expression of active, mature heterologous protein. In one embodiment the precursor polypeptide is a precursor polypeptide of FIX.

U.S. Pat. No. 5,935,815, issued to van de Ven et al., likewise describes recombinant human furin (i.e., PACE) and the coexpression of furin with a substrate precursor polypeptide of a heterologous protein to improve expression of active, mature heterologous protein. Possible substrate precursors disclosed in this patent include a precursor of Factor IX.

Other family members in the mammalian subtilisin/Kex2p-like proprotein convertase (PC) family in addition to PACE are reported to include PC1/PC3, PC2, PC4, PC5/6 (hereinafter referred to simply as PC5), PACE4, and LPC/PC7/PC8/SPC7. While these various members share certain conserved overall structural features, they differ in their tissue distribution, subcellular localization, cleavage specificities, and preferred substrates. For a review, see Nakayama K (1997) *Biochem J.* 327:625-35. Similar to PACE, these proprotein convertases generally include, beginning from the amino terminus, a signal peptide, a propeptide (that may be autocatalytically cleaved), a subtilisin-like catalytic domain characterized by Asp, His, Ser, and Asn/Asp residues, and a Homo B domain that is also essential for catalytic activity and characterized by an Arg-Gly-Asp (RGD) sequence. PACE, PACE4, and PC5 also include a Cys-rich domain, the function of which is unknown. In addition, PC5 has isoforms with and without a transmembrane domain; these different isoforms are known as PC5B and PC5A, respectively. Comparison between the amino acid sequence of the catalytic domain of PACE and the amino acid sequences of the catalytic domains of other members of this family of proprotein convertases reveals the following degrees of identity: 70 percent for PC4; 65 percent for PACE4 and PC5; 61 percent for PC1/PC3; 54 percent for PC2; and 51 percent for LPC/PC7/PC8/SPC7. Nakayama K (1997) *Biochem J.* 327:625-35.

PACE and PACE4 have been reported to have partially overlapping but distinct substrates. In particular, PACE4, in striking contrast to PACE, has been reported to be incapable of processing the precursor polypeptide of FIX. Wasley L C et al. (1993) *J Biol. Chem.* 268:8458-65; Rehemtulla A et al. (1993) *Biochemistry.* 32:11586-90.

U.S. Pat. No. 5,840,529, issued to Seidah et al., discloses nucleotide and amino acid sequences for human PC7 and the notable ability of PC7, as compared to other PC family members, to cleave HIV gp160 to gp120 and gp41.

Nucleotide and amino acid sequences of rodent PC5 were first described as PC5 by Lusson J et al. (1993) *Proc Natl Acad Sci USA* 90:6691-5 and as PC6 by Nakagawa T et al. (1993) *J Biochem* (Tokyo) 113:132-5.

U.S. Pat. No. 6,380,171, issued to Day et al., discloses nucleotide and amino acid sequences for human PC5A, the isoform without the transmembrane domain, as well as methods for reducing restenosis by using antisense nucleic acids to inhibit PC5 activity.

SUMMARY OF THE INVENTION

The invention is based in part on the discovery by the inventors that PC5 is effective for processing propeptide from the precursor polypeptide of FIX. This discovery was unexpected because, as described in detail below, closely related PC family members are completely or substantially incapable of processing propeptide from the precursor polypeptide of FIX. The invention relates to methods and compositions useful for preparing mature Factor IX, using PC5 to process the precursor polypeptide of FIX. The methods and compositions relate to FIX per se as well as to FIX-containing polypeptides and conjugates.

In one aspect the invention is a eukaryotic cell including a first expression vector encoding a proprotein of Factor IX (proFIX), or a fusion protein thereof, and a second expression vector encoding a functional PC5.

In one embodiment according to this and other aspects of the invention, the functional PC5 includes an amino acid sequence provided by SEQ ID NO:1, corresponding to PC5A, an isoform of PC5 without a transmembrane domain.

In one embodiment according to this and other aspects of the invention, the functional PC5 comprises an amino acid sequence corresponding to PC5B, an isoform of PC5 with a transmembrane domain.

In one embodiment according to this and other aspects of the invention, the first expression vector encodes proFIX.

In one embodiment according to this and other aspects of the invention, the fusion protein is a proFIX-FcRn binding partner fusion protein.

In one embodiment according to this and other aspects of the invention, the proFIX-FcRn binding partner fusion protein comprises a linker connecting proFIX to FcRn binding partner.

In one embodiment according to this and other aspects of the invention, the proFIX-FcRn binding partner fusion protein is a proFIX-Fc fusion protein.

In one embodiment according to this and other aspects of the invention, the proFIX-Fc fusion protein comprises a human Fc gamma.

In one embodiment according to this and other aspects of the invention, the proFIX-FcRn binding partner fusion protein comprises a linker connecting proFIX to Fc.

In one embodiment according to this and other aspects of the invention, the proFIX-Fc fusion protein is a proFIX-Fc homodimer (also referred to herein simply as "dimer").

In one embodiment according to this and other aspects of the invention, the proFIX-Fc fusion protein is a proFIX-Fc monomer-dimer hybrid (also referred to herein simply as "monomer").

In one embodiment according to this and other aspects of the invention, the fusion protein is a proFIX-albumin fusion protein.

In one embodiment according to this and other aspects of the invention, the proFIX-albumin fusion protein includes a linker connecting proFIX to albumin.

In one embodiment according to this and other aspects of the invention, the fusion protein is a proFIX-transferrin fusion protein.

In one embodiment according to this and other aspects of the invention, the proFIX-transferrin fusion protein includes a linker connecting proFIX to transferrin.

In one embodiment according to this and other aspects of the invention, the linker is GGGGSGGGGSGGGGSGGGGSGGGGSGGGGS (SEQ ID NO:16).

In one embodiment the eukaryotic cell is a mammalian cell.

In one embodiment the eukaryotic cell is a HEK 293 cell.
In one embodiment the eukaryotic cell is a CHO cell.
In one embodiment the eukaryotic cell is a BHK cell.

In one embodiment the expression vector encoding the proFIX or the fusion protein thereof, and the expression vector encoding the functional PC5, are a single expression vector.

The invention in one aspect is an expression vector including a first polynucleotide sequence encoding a proprotein of Factor IX (proFIX), or a fusion protein thereof, operably linked to an expression control sequence permitting expression of the proFIX or the fusion protein thereof, and a second polynucleotide sequence encoding a functional PC5, operably linked to an expression control sequence permitting expression of the functional PC5.

In one aspect the invention is a method for producing a mature Factor IX-containing polypeptide from a proprotein of Factor IX (proFIX), or a fusion protein thereof. The method according to this aspect of the invention includes the steps of culturing a eukaryotic cell including a first expression vector encoding a proprotein of Factor IX (proFIX), or a fusion protein thereof, and a second expression vector encoding a functional PC5, under conditions that allow expression of both the proFIX or the fusion protein thereof and the functional PC5, and processing of the proFIX or the fusion protein thereof by the functional PC5. In one embodiment the mature Factor IX-containing polypeptide is a FIX-Fc monomer-dimer hybrid. Also provided is a FIX-Fc monomer-dimer hybrid produced according to the method of this aspect of the invention.

In one aspect the invention is a method for increasing yield of a mature Factor IX-containing polypeptide from a proprotein of Factor IX (proFIX), or a fusion protein thereof. The method according to this aspect of the invention includes the steps of culturing a eukaryotic cell including a first expression vector encoding a proprotein of Factor IX (proFIX), or a fusion protein thereof, and a second expression vector encoding a functional PC5, under conditions that allow (a) expression of both the proFIX or the fusion protein thereof and the functional PC5, and (b) processing of the proFIX or the fusion protein thereof by the functional PC5, wherein yield of mature Factor IX-containing polypeptide is increased compared to yield of mature Factor IX-containing polypeptide produced under similar conditions without the processing by the functional PC5.

In one aspect the invention is a method for producing a mature Factor IX-containing polypeptide from a proprotein of Factor IX (proFIX), or a conjugate thereof. The method according to this aspect of the invention includes the step of contacting the proFIX or the conjugate thereof with an effective amount of functional PC5.

In one embodiment the proFIX or the conjugate thereof is proFIX.

In one embodiment the mature Factor IX-containing polypeptide is a FIX-Fc monomer-dimer hybrid. Also provided is a FIX-Fc monomer-dimer hybrid produced according to the method of this aspect of the invention.

In one embodiment the proFIX or the conjugate thereof is a PEGylated proFIX.

In one embodiment the proFIX or the conjugate thereof is a proFIX-FcRn binding partner fusion protein.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF THE DRAWINGS

The figures are illustrative only and are not required for enablement of the invention disclosed herein.

FIG. 4 shows FIX and FIX propeptide Western blots (reducing SDS-PAGE) of protein A immunoprecipitations of FIX-Fc from transiently transfected Chinese hamster ovary (CHO) cells, alone or with PACE-SOL, PC7-SOL, PC5, or KEX2-SOL.

FIG. 5 shows FIX and FIX propeptide Western blots and the corresponding SDS-PAGE gel (all under non-reducing conditions) of protein A purified proteins from CHO cells stably transfected with FIX-Fc, Fc, and either PACE-SOL or PC7-SOL. MWM, molecular weight marker.

FIG. 6 shows FIX and FIX propeptide Western blots (all under non-reducing conditions) of protein A immunoprecipitations from CHO cells stably transfected with FIX-Fc, Fc, and PC5 (lanes 1-3), or CHO cells stably transfected with FIX-Fc either alone (lane 4) or with PACE-SOL (lane 5).

FIG. 7 shows FIX and FIX propeptide Western blots of protein A immunoprecipitations from HEK 293 cells transiently transfected with FIX-Fc and Fc, either without processing enzyme (lanes 3, "–") or with PC5 (lanes 4-7) or PC7-SOL (lanes 8-11). Purified FIX-Fc from CHO cells transfected with (lanes 2) or without (lanes 1) PACE-SOL were used as controls. Lanes 12, molecular weight markers.

FIG. 8 shows FIX (non-reducing) and FIX propeptide (reducing) Western blots of protein A immunoprecipitations of FIX-Fc dimer, monomer-dimer hybrid (monomer), and Fc from transiently transfected HEK 293 cells, with KEX2-SOL (lanes 3 and 4). Purified FIX-Fc homodimer from CHO cells transfected with (lane 2) or without PACE (lane 1) were used as controls.

FIG. 9 shows FIX and FIX propeptide Western blots and the corresponding SDS-PAGE gel (all under non-reducing conditions) of purified FIX-Fc monomer-dimer hybrid (monomer) from HEK 293 cells stably transfected with FIX-Fc, Fc and PC5. Purified FIX-Fc homodimer from CHO cells transfected with either PACE-SOL or PC7-SOL were used as controls.

FIG. 10 shows FIX and FIX propeptide Western blots (reducing conditions) of protein A immunoprecipitations of FIX-Fc dimer, monomer-dimer hybrid (monomer), and Fc from stably transfected HEK 293 cells, alone (lanes 3 and 4) or with PC7-SOL (lanes 5 and 6). Purified FIX-Fc homodimer from CHO cells transfected with (lane 2) or without (lane 1) PACE-SOL were used as controls. Lane 7, molecular weight standards.

DETAILED DESCRIPTION OF THE INVENTION

Figure 1:
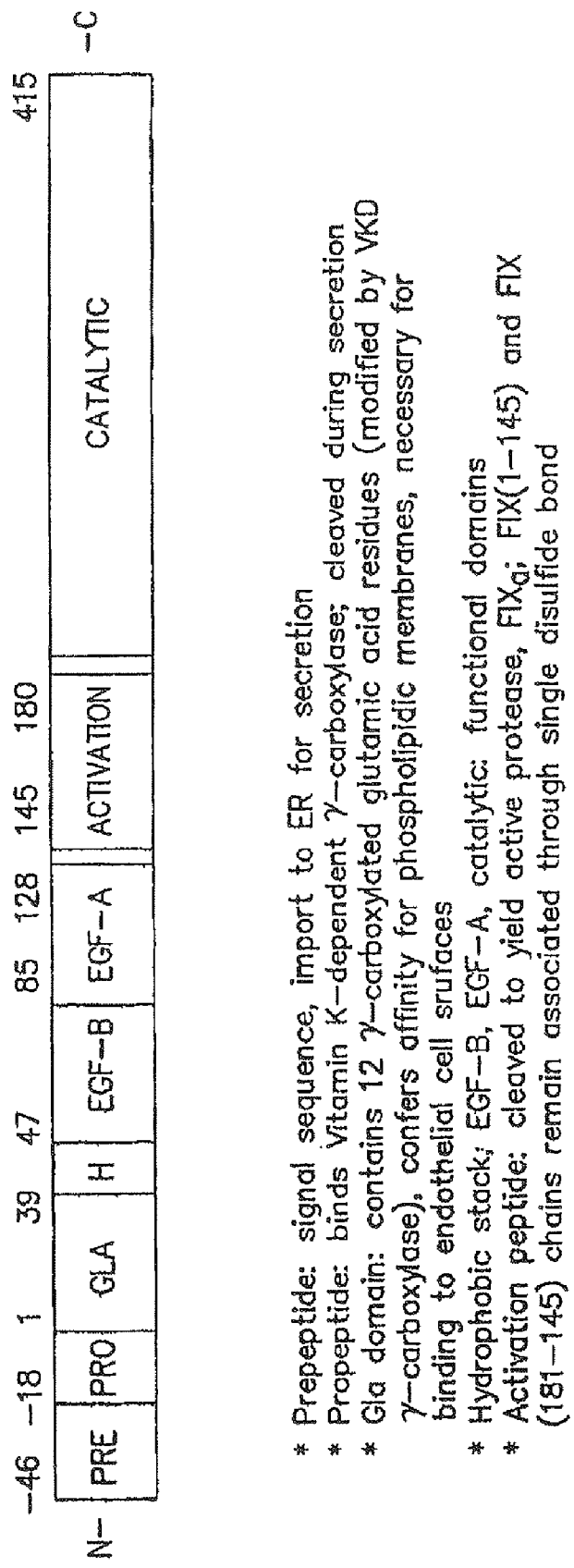
FIG. 1 is a schematic drawing of prepro Factor IX, including the following domains: prepeptide (PRE), propeptide (PRO), Gla domain (GLA), H domain (H), EGF-B and EGF-A domains, activation peptide, and catalytic domain. Mature Factor IX lacks the prepeptide and propeptide domains. Mature, activated Factor IX (Factor IXa) further lacks the activation peptide, and the catalytic domain remains associated with the EGF-A domain through a disulfide linkage.

The invention relates at least in part to compositions and methods related to PC5 useful for preparation of FIX and conjugates of FIX, including FIX fusion proteins. In certain particular embodiments the PC5 is PC5A and the FIX fusion protein is a FIX-Fc monomer-dimer hybrid, discussed below.

The invention in one aspect relates to a eukaryotic cell that includes a first expression vector encoding a proprotein of Factor IX and a second expression vector encoding a functional PC5 polypeptide. As used herein, a functional PC5 polypeptide refers to an enzymatically active polypeptide comprising at least a homo B domain and a subtilisin-like catalytic domain of a proprotein convertase PC5. In one embodiment a functional PC5 polypeptide refers to an enzymatically active polypeptide comprising at least a homo B domain and a subtilisin-like catalytic domain of a human proprotein convertase PC5. In one embodiment a functional PC5 polypeptide refers to an enzymatically active polypeptide comprising at least a homo B domain and a subtilisin-like catalytic domain of a proprotein convertase PC5, wherein the functional PC5 is PC5A. As mentioned above, the PC5A isomer lacks a transmembrane domain. In contrast, a PC5B isomer includes a C-terminal transmembrane domain. In one embodiment a functional PC5 polypeptide refers to art enzymatically active polypeptide comprising at least a homo B domain and a subtilisin-like catalytic domain of a proprotein convertase PC5, wherein the functional PC5 is human PC5A.

An amino acid sequence for human PC5A is provided as GenBank accession no. NP_006191 (reproduced as SEQ ID NO:1), the entire contents of which are incorporated herein.

SEQ ID NO: 1

```
MGWGSRCCCP GRLDLLCVLA LLGGCLLPVC RTRVYTNHWA VKIAGGFPEA NRIASKYGFI  60
NIGQIGALKD YYHFYHSRTI KRSVISSRGT HSFISMEPKV EWIQQQVVKK RTKRDYDFSR 120
AQSTYFNDPK WPSMWYMHCS DNTHPCQSDM NIEGAWKRGY TGKNIVVTIL DDGIERTHPD 180
LMQNYDALAS CDVNGNDLDP MPRYDASNEN KHGTRCAGEV AAAANNSHCT VGIAFNAKIG 240
GVRMLDGDVT DMVEAKSVSF NPQHVHIYSA SWGPDDDGKT VDGPAPLTRQ AFENGVRMGR 300
RGLGSVFVWA SGNGGRSKDH CSCDGYTNSI YTISISSTAE SGKKPWYLEE CSSTLATTYS 360
SGESYDKKII TTDLRQRCTD NHTGTSASAP MAAGIIALAL EANPFLTWRD VQHVIVRTSR 420
AGHLNANDWK TNAAGFKVSH LYGFGLMDAE AMVMEAEKWT TVPRQHVCVE STDRQIKTIR 480
PNSAVRSIYK ASGCSDNPNR HVNYLEHVVV RITITHPRRG DLAIYLTSPS GTRSQLLANR 540
LFDHSMEGFK NWEFMTIHCW GERAAGDWVL EVYDTPSQLR NFKTPGKLKE WSLVLYGTSV 600
QPYSPTNEFP KVERFRYSRV EDPTDDYGTE DYAGPCDPEC SEVGCDGPGP DHCNDCLHYY 660
YKLKNNTRIC VSSCPPGHYH ADKKRCRKCA PNCESCFGSH GDQCMSCKYG YFLNEETNSC 720
VTHCPDGSYQ DTKKNLCRKC SENCKTCTEF HNCTECRDGL SLQGSRCSVS CEDGRYFNGQ 780
DCQPCHRFCA TCAGAGADGC INCTEGYFME DGRCVQSCSI SYYFDHSSEN GYKSCKKCDI 840
SCLTCNGPGF KNCTSCPSGY LLDLGMCQMG AICKDATEES WAEGGFCMLV KKNNLCQRKV 900
LQQLCCKTCT FQG                                                   913
```

Referring to SEQ ID NO:1, the PC5 signal peptide spans amino acid residues 1-32, the PC5 propeptide spans amino acid residues 33-114, and the mature PC5 protein (beginning with the subtilisin-like catalytic domain) spans amino acid residues 115-913. In one embodiment a functional PC5 polypeptide refers to a polypeptide having an amino acid sequence provided as SEQ ID NO:1. In one embodiment a functional PC5 polypeptide refers to a polypeptide having an amino acid sequence provided as amino acid residues 33-913 of SEQ ID NO: 1. In one embodiment a functional PC5 polypeptide refers to a polypeptide having an amino acid sequence provided as amino acid residues 115-913 of SEQ ID NO:1.

Owing to the degeneracy of the genetic code, a human PC5A polypeptide can be encoded by any suitable nucleotide sequence. In one embodiment a nucleotide sequence for human PC5A is provided as nucleotides 478-3216 of GenBank accession no. NM_006200 (reproduced as SEQ ID NO:2), the entire contents of which is incorporated herein by reference. This sequence encodes SEQ ID NO:1 above.

SEQ ID NO: 2

```
atgggctggg ggagccgctg ctgctgcccg ggacgtttgg
acctgctgtg cgtgctggcg ctgctcgggg gctgcctgct
ccccgtgtgt cggacgcgcg tctacaccaa ccactgggca
gtcaaaatcg ccggggggctt cccggaggcc aaccgtatcg
ccagcaagta cggattcatc aacataggac agatagggggc
cctgaaggac tactaccact tctaccatag caggacgatt
aaaaggtcag ttatctcgag cagagggacc cacagtttca
tttcaatgga accaaaggtg gaatggatcc aacagcaagt
ggtaaaaaag cggacaaaga gggattatga cttcagtcgt
gcccagtcta cctatttcaa tgatcccaag tggcccagca
tgtggtatat gcactgcagt gacaatacac atccctgcca
gtctgacatg aatatcgaag gagcctggaa gagaggctac
acgggaaaga acattgtggt cactatcctg gatgacggaa
ttgagagaac ccatccagat ctgatgcaaa actacgatgc
tctggcaagt tgcgacgtga atgggaatga cttggaccca
atgcctcgtt atgatgcaag caacgagaac aagcatggga
ctcgctgtgc tggagaagtg gcagccgctg caaacaattc
gcactgcaca gtcggaattg ctttcaacgc caagatcgga
ggagtgcgaa tgctggacgg agatgtcacg gacatggttg
aagcaaaatc agttagcttc aaccccagc acgtgcacat
ttacagcgcc agctggggcc cggatgatga tggcaagact
gtggacggac cagccccct cacccggcaa gcctttgaaa
acggcgttag aatggggcgg agaggcctcg gctctgtgtt
```

```
tgtttgggca tctggaaatg gtggaaggag caaagaccac tgctcctgtg atggctacac caacagcatc tacaccatct ccatcagcag cactgcagaa agcggaaaga aaccttggta cctggaagag tgttcatcca cgctggccac aacctacagc agcggggagt cctacgataa gaaaatcatc actacagatc tgaggcagcg ttgcacggac aaccacactg ggacgtcagc ctcagccccc atggctgcag gcatcattgc gctggccctg gaagccaatc cgtttctgac ctggagagac gtacagcatg ttattgtcag gacttcccgt gcgggacatt tgaacgctaa tgactggaaa accaatgctg ctggttttaa ggtgagccat ctttatggat ttggactgat ggacgcagaa gccatggtga tggaggcaga gaagtggacc accgttcccc ggcagcacgt gtgtgtggag agcacagacc gacaaatcaa gacaatccgc cctaacagtg cagtgcgctc catctacaaa gcttcaggct gctcggataa ccccaaccgc catgtcaact acctggagca cgtcgttgtg cgcatcacca tcacccaccc caggagagga gacctggcca tctacctgac ctcgccctct ggaactaggt ctcagctttt ggccaacagg ctatttgatc actccatgga aggattcaaa aactgggagt tcatgaccat tcattgctgg ggagaaagag ctgctggtga ctgggtcctt gaagtttatg atactccctc tcagctaagg aactttaaga ctccaggtaa attgaaagaa tggtctttgg tcctctacgg cacctccgtg cagccatatt caccaaccaa tgaatttccg aaagtggaac ggttccgcta tagccgagtt gaagacccca cagacgacta tggcacagag gattatgcag gtccctgcga ccctgagtgc agtgaggttg gctgtgacgg gccaggacca gaccactgca atgactgttt gcactactac tacaagctga aaaacaatac caggatctgt gtctccagct gccccctgg ccactaccac gccgacaaga agcgctgcag gaagtgtgcc cccaactgtg agtcctgctt tgggagccat ggtgaccaat gcatgtcctg caaatatgga tactttctga atgaagaaac caacagctgt gttactcact gccctgatgg gtcatatcag gataccaaga aaaatctttg ccggaaatgc agtgaaaact gcaagacatg tactgaattc cataactgta cagaatgtag ggatgggtta agcctgcagg gatcccggtg ctctgtctcc tgtgaagatg gacggtattt caacggccag gactgccagc cctgccaccg cttctgcgcc acttgtgctg gggcaggagc tgatgggtgc attaactgca cagagggcta cttcatggag gatgggagat gcgtgcagag ctgtagtatc agctattact ttgaccactc ttcagagaat ggatacaaat cctgcaaaaa atgtgatatc agttgtttga cgtgcaatgg cccaggattc aagaactgta
```

```
caagctgccc tagtgggtat ctcttagact taggaatgtg tcaaatggga gccatttgca aggatgcaac ggaagagtcc tgggcggaag gaggcttctg tatgcttgtg aaaaagaaca atctgtgcca acggaaggtt cttcaacaac tttgctgcaa aacatgtaca tttcaaggc
```

The nucleotide sequence encoding the PC5 polypeptide can contain substitutions that do not affect the amino acid sequence. In one embodiment, the nucleotide at position 876 of GenBank accession no. NM_006200 can be replaced by thymidine (T) instead of cytidine (C), but preserve the amino acid Ser 133 (corresponding to amino acid numbering in GenBank accession no. NP_006191). In one embodiment the nucleotide at position 1950 of GenBank accession no. NM_006200 can be replaced by cytidine (C) instead of thymidine (T), but preserve the amino acid Ala 491. Note that this nucleotide change at position 1950 eliminates a HindIII restriction site. In one embodiment the nucleotide at position 1962 of GenBank accession no. NM_006200 can be replaced by adenine (A) instead of guanosine (G), but preserve the amino acid Ser 496. In one embodiment the nucleotide sequence encoding PC5 is as provided below in Example 3. In further embodiments any combination of the aforementioned substitutions can be present. In yet further additional embodiments similar types of substitutions are also contemplated by the invention and are within the skill of the skilled artisan to make and use in the practice of the invention.

The PC5 sequence can also contain other non-coding changes at the nucleotide level that can be found in the SNP database. For example, in various embodiments Leu 16 can have an adenine (A) instead of a guanosine (G) at codon position 3; Cys 30 can have a cytosine (C) instead of a thymidine (T) at codon position 3; Thr 385 can have an adenine (A) instead of a guanosine (G) at codon position 3; Ser 495 can have an adenine (A) instead of a guanosine (G) at codon position 3; Pro 623 can have a thymidine (T) instead of a cytosine (C) at codon position 3; Cys 767 can have a thymidine (T) instead of a cytosine (C) at codon position 3; and any combination thereof. These examples are not intended to be limiting in any way.

As used herein, a proprotein of Factor IX (proFIX) refers to any Factor IX polypeptide that includes at least a Factor IX propeptide, a Gla domain, and a Factor IX catalytic domain. The Factor IX propeptide is positioned N-terminal adjacent to the Gla domain. In one embodiment the proprotein of Factor IX further includes a prepeptide (signal sequence) N-terminal to the propeptide. In one embodiment the proprotein of Factor IX is a proprotein of a human Factor IX. A human Factor IX proprotein in one embodiment has an amino acid sequence provided as GenBank accession no. NP_000124, reproduced below as SEQ ID NO:3. In this sequence amino acid residues 1-28 represent a prepeptide (signal sequence); amino acid residues 29-46 represent a propeptide; amino acid residues 47-86 represent a Gla domain containing twelve glutamic acid residues; amino acid residues 191-226 represent an activation peptide; and amino acid residues 227-461 represent a catalytic domain. The activation peptide is cleaved by Factor XIa to yield a heavy chain and a light chain which are covalently associated by one or more disulfide bonds. It should be noted that in one embodiment the threonine at amino acid 194 in SEQ ID NO:3 can be replaced by an alanine.

```
                                                      SEQ ID NO: 3
MQRVNMIMAE  SPGLITICLL  GYLLSAECTV  FLDHENANKI  LNRPKRYNSG  KLEEFVQGNL   60

ERECMEEKCS  FEEAREVFEN  TERTTEFWKQ  YVDGDQCESN  PCLNGGSCKD  DINSYECWCP  120

FGFEGKNCEL  DVTCNIKNGR  CEQFCKNSAD  NKVVCSCTEG  YRLAENQKSC  EPAVPFPCGR  180

VSVSQTSKLT  RAETVFPDVD  YVNSTEAETI  LDNITQSTQS  FNDFTRVVGG  EDAKPGQFPW  240

QVVLNGKVDA  FCGGSIVNEK  WIVTAAHCVE  TGVKITVVAG  EHNIEETEHT  EQKRNVIRII  300

PHHNYNAAIN  KYNHDIALLE  LDEPLVLNSY  VTPICIADKE  YTNIFLKFGS  GYVSGWGRVF  360

HKGRSALVLQ  YLRVPLVDRA  TCLRSTKFTI  YNNMFCAGFH  EGGRDSCQGD  SGGPHVTEVE  420

GTSFLTGIIS  WGEECAMKGK  YGIYTKVSRY  VNWIKEKTKL  T                      461
```

Owing to the degeneracy of the genetic code, a proprotein of human Factor IX can be encoded by any suitable nucleotide sequence. In one embodiment a nucleotide sequence encoding a proprotein of human Factor IX is provided as nucleotides 30-1412 of GenBank accession no. NM_000133, reproduced below as SEQ ID NO:4. This sequence encodes SEQ ID NO:3 above.

```
                                       SEQ ID NO: 4
atgcagcgcg  tgaacatgat  catggcagaa  tcaccaggcc tcatcaccat  ctgccttta   ggatatctac  tcagtgctga atgtacagtt  tttcttgatc  atgaaaacgc  caacaaaatt ctgaatcggc  caaagaggta  taattcaggt  aaattggaag agtttgttca  agggaacctt  gagagagaat  gtatggaaga aaagtgtagt  tttgaagaag  cacgagaagt  ttttgaaaac actgaaagaa  caactgaatt  ttggaagcag  tatgttgatg gagatcagtg  tgagtccaat  ccatgtttaa  atggcggcag ttgcaaggat  gacattaatt  cctatgaatg  ttggtgtccc tttggatttg  aaggaaagaa  ctgtgaatta  gatgtaacat gtaacattaa  gaatggcaga  tgcgagcagt  tttgtaaaaa tagtgctgat  aacaaggtgg  tttgctcctg  tactgaggga tatcgacttg  cagaaaacca  gaagtcctgt  gaaccagcag tgccatttcc  atgtggaaga  gtttctgttt  cacaaacttc taagctcacc  cgtgctgaga  ctgttttttcc  tgatgtggac tatgtaaatt  ctactgaagc  tgaaaccatt  ttggataaca tcactcaaag  cacccaatca  tttaatgact  tcactcgggt tgttggtgga  gaagatgcca  aaccaggtca  attcccttgg caggttgttt  tgaatggtaa  agttgatgca  ttctgtggag gctctatcgt  taatgaaaaa  tggattgtaa  ctgctgccca ctgtgttgaa  actggtgtta  aaattacagt  tgtcgcaggt gaacataata  ttgaggagac  agaacataca  gagcaaaagc gaaatgtgat  tcgaattatt  cctcaccaca  actacaatgc agctattaat  aagtacaacc  atgacattgc  ccttctggaa ctggacgaac  ccttagtgct  aaacagctac  gttaccctta tttgcattgc  tgacaaggaa  tacacgaaca  tcttcctcaa
```

-continued

```
atttggatct  ggctatgtaa  gtggctgggg  aagagtcttc cacaaaggga  gatcagcttt  agttcttcag  taccttagag ttccacttgt  tgaccgagcc  acatgtcttc  gatctacaaa gttcaccatc  tataacaaca  tgttctgtgc  tggcttccat gaaggaggta  gagattcatg  tcaaggagat  agtggggac cccatgttac  tgaagtggaa  gggaccagtt  tcttaactgg aattattagc  tggggtgaag  agtgtgcaat  gaaaggcaaa tatggaatat  ataccaaggt  atcccggtat  gtcaactgga ttaaggaaaa  aacaaagctc  act
```

As used herein, polypeptide refers to a polymer of amino acids and does not refer to a specific length of the polymer; thus, peptides, oligopeptides, and proteins are included within the definition of polypeptide. In one embodiment a polypeptide is a single-chain polypeptide. As used herein, a protein can be a single-chain polypeptide or it can include more than one single-chain polypeptide. Also as used herein, the term polypeptide can include polypeptides that have one or more post-expression modifications, for example, glycosylation, acetylation, phosphorylation, pegylation, addition of a lipid moiety, or the addition of any organic or inorganic molecule. Amino acids specifically include but are not limited to common so-called naturally occurring amino acids. These include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. Included within the definition of polypeptide are, for example, polypeptides containing one or more analogs of an amino acid (including, for example, unnatural amino acids) and polypeptides with substituted linkages, as well as other modifications known in the art, both naturally occurring and non-naturally occurring. In one embodiment a polypeptide is a fusion protein.

Various changes may be made in the amino acid sequences of the polypeptides and proteins or components thereof of the invention, or corresponding DNA sequences encoding such polypeptides and proteins, without appreciable loss of their biological activity, function, or utility. Derivatives, analogs, or mutants resulting from such changes and the use of such derivatives are within the scope of the present invention.

As will be appreciated by those of skill in the art, substitutes for an amino acid may be selected from other members of a class to which the amino acid belongs (see, e.g., Table 1). Furthermore, various amino acids are commonly substituted with neutral amino acids, e.g., alanine, leucine, isoleucine, valine, proline, phenylalanine, tryptophan, and methionine. See, e.g., MacLennan D H et al., *Acta Physiol Scand Suppl.* 643:55-67 (1988); Sasaki N et al., *Adv Biophys.* 35:1-24 (1998).

TABLE 1

| Original Residue | Exemplary Substitutions | Typical Substitution |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Lys |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4-Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

A fusion protein, as used herein, refers to a recombinant fusion protein encompassing at least two heterologous polypeptides. A recombinant fusion protein refers to a protein encoded by a single nucleotide sequence derived from at least two heterologous nucleotide sequences covalently linked to one another such that coding sequence from each component nucleotide sequence is translated in its proper reading frame. General methods for making recombinant DNA constructs are well known in the art. As disclosed below, a fusion protein is a type of a conjugate as used herein. Fusion proteins in one embodiment can optionally be modified to include one or more carbohydrate or other non-proteinaceous moieties.

As described in greater detail below, a fusion protein can optionally include a linker moiety between any of the component amino acid sequences. The optional linker moiety can but need not include one or more amino acids. In one embodiment the optional linker moiety is a peptide at least two amino acid residues long.

Fusion proteins of the invention generally include proFIX fusion proteins. In one embodiment the proFIX fusion protein is a proFIX-albumin fusion protein. A proFIX-albumin fusion protein as used herein refers to a fusion protein that includes a proFIX polypeptide covalently bonded to albumin. The proFIX polypeptide can be fused to either the N-terminal end of an albumin polypeptide or to the C-terminal end of an albumin polypeptide, provided the proFIX component of the proFIX-albumin fusion protein can be processed by enzymatically active PC5 to yield a mature FIX-containing polypeptide, as described herein. In one embodiment the proFIX polypeptide is a human proFIX polypeptide and the albumin polypeptide is a human albumin polypeptide.

In another embodiment the proFIX fusion protein is a proFIX-transferrin fusion protein. A proFIX-transferrin fusion protein as used herein refers to a fusion protein that includes a proFIX polypeptide covalently bonded to transferrin. The proFIX polypeptide can be fused to either the N-terminal end of an transferrin polypeptide or to the C-terminal end of an transferrin polypeptide, provided the proFIX component of the proFIX-transferrin fusion protein can be processed by enzymatically active PC5 to yield a mature FIX-containing polypeptide, as described herein. In one embodiment the proFIX polypeptide is a human proFIX polypeptide and the transferrin polypeptide is a human transferrin polypeptide.

Figure 2:
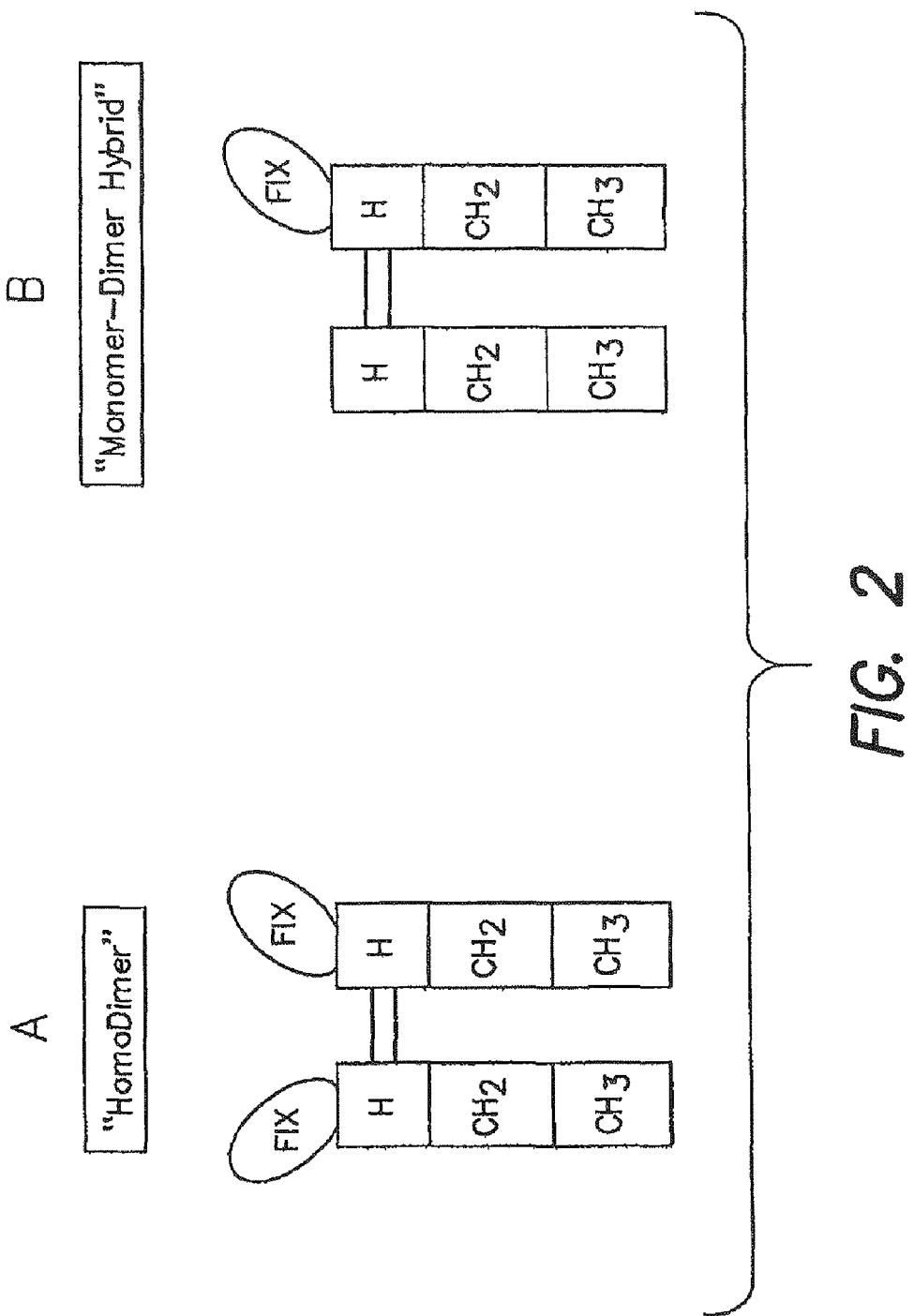
FIG. 2A is a schematic drawing of the structure of a FIX-Fc homodimer.
FIG. 2B is a schematic drawing of the structure of a FIX-Fc monomer-dimer hybrid.
Figure 3:
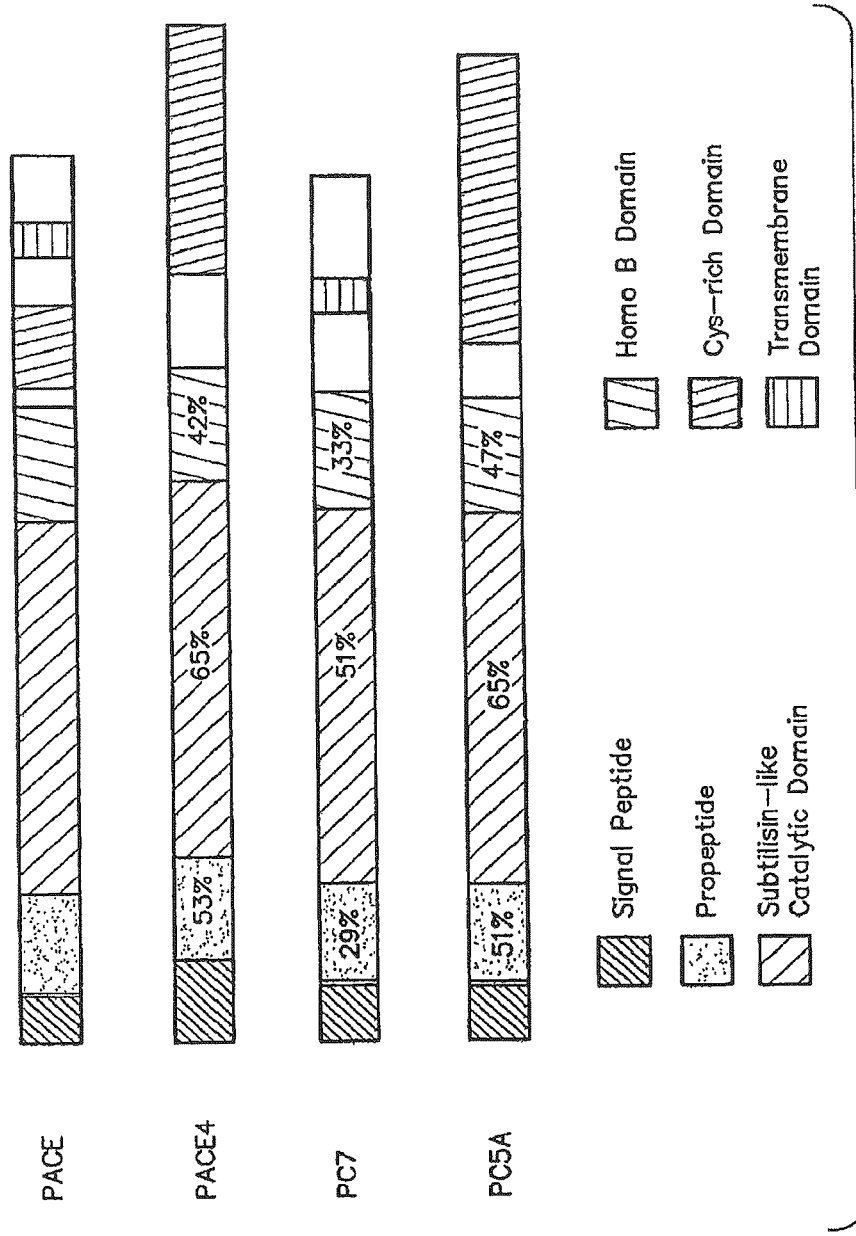
FIG. 3 is a schematic drawing of PACE, PACE4, PC7, and PC5A (top to bottom, respectively), showing the following domains: signal peptide, propeptide, subtilisin-like catalytic domain, homo B domain, Cys-rich domain, and (PACE and PC7 only) transmembrane domain. Shown percentages indicate percent amino acid identity with PACE within each corresponding domain.

Featured proFIX fusion proteins of the invention include proFIX fusion proteins that can be specifically bound by a neonatal Fc receptor (FcRn). These featured proFIX fusion proteins include a proFIX-FcRn binding partner fusion protein, a proFIX-Fc fusion protein, a proFIX-Fc homodimer, and a proFIX-Fc monomer-dimer hybrid (see, e.g., FIG. 2).

As used herein, FcRn or, equivalently, FcRn receptor, refers to neonatal Fc receptor. FcRn was first described as an enterocyte receptor for IgG in neonatal rats and mice. This receptor binds to the Fc portion of immunoglobulin G (IgG) and transports IgG by transcytosis in a luminal to serosal direction, i.e., from gut lumen to interstitium, in a process believed to be responsible for delivery of maternal IgG to the neonate. FcRn-mediated transport of IgG is believed to underlie passive acquisition of IgG during the newborn suckling period. It was subsequently discovered that FcRn is widely expressed on multiple types of human epithelia, not only in newborns but also in adults.

The FcRn has been the basis for systemic delivery of a number of molecules provided as conjugates with FcRn binding partners. See U.S. Pat. Nos. 6,030,613, 6,086,875, and 6,485,726, and published international patent application WO 03/077834. The FcRn now is well characterized. The FcRn has been isolated for several mammalian species, including humans. Sequences of the human, rat, and mouse FcRn molecules can be found, for example, in Story C M et al. (1994) *J Exp Med.* 180:2377-81. The FcRn binds IgG (but not other immunoglobulin classes such as IgA, IgD, IgM and IgE) at a relatively lower pH, actively transports the IgG transcellularly in a luminal to serosal direction, and then releases the IgG at a relatively higher pH found in the interstitial fluids. As will be recognized by those of ordinary skill in the art, FcRn can be isolated by cloning or by affinity purification using, for example, monoclonal antibodies. Such isolated FcRn then can be used to identify and isolate FcRn binding partners.

As used herein, an FcRn binding partner means any entity that can be specifically bound by an FcRn. The FcRn binding partner in certain embodiments can include but is not limited to whole IgG, an Fc fragment of IgG, and other fragments of IgG that include the complete binding region for the FcRn. The region of the Fc portion of IgG that binds to the FcRn has been described based upon X-ray crystallography (Burmeister W P et al., *Nature* 372:379-83 (1994)). The major contact area of Fc with the FcRn is near the junction of the $C_H2$ and $C_H3$ domains. Following the numbering convention for amino acids based on Kabat at al. (Sequences of Proteins of Immunological Interest, U.S. Department of Public Health, Bethesda, Md., 1991), potential contacts are residues 248, 250-257, 272, 285, 288, 290-291, 308-311 and 314 in $C_H2$ and 385-387, 428 and 433-436 in $C_H3$. These sites are distinct from those identified by subclass comparison or by site-directed mutagenesis as important for Fc binding to leukocyte FcγRI and FcγRII. The foregoing Fc-FcRn contacts are all within a single Ig heavy chain. It has been noted previously that two FcRn can bind a single (homodimeric) Fc molecule. The crystallographic data suggest that in such a complex, each FcRn molecule binds a single polypeptide of the Fc homodimer FcRn binding partner. Thus in one embodiment a fragment of IgG that includes the complete binding region for the FcRn includes at least the major contact area of Fc with the FcRn near the junction of the $C_H2$ and $C_H3$ domains.

In one embodiment an FcRn binding partner is an FcRn binding partner other than a whole IgG. In one embodiment an FcRn binding partner is an FcRn binding partner other than a whole human IgG.

In one embodiment an FcRn binding partner is an Fc fragment of IgG. Except as specified otherwise herein, an Fc fragment of IgG is a homodimer of IgG heavy chain polypeptide fragments (i.e., Fc polypeptides) which, when associated, together constitute a fragment of whole IgG that includes the hinge, $C_H2$, and $C_H3$ domains of IgG. An Fc fragment of IgG corresponds to a proteolytic fragment of IgG containing only the disulfide-linked carboxyl terminal regions of the two heavy chains of IgG. Fc fragments of IgG mediate effector functions by binding to certain Fc receptors and C1q complement protein, and they are to be distinguished from antigen-binding Fab fragments of IgG. In one embodiment an FcRn binding partner is an Fc fragment of a human IgG, i.e., a human Fc gamma. In a particular embodiment an FcRn binding partner is an Fc fragment of a human IgG1 (i.e., Fcγ1). In one embodiment each polypeptide of an Fc fragment (i.e., each Fc polypeptide) of a human IgG has an amino acid sequence as provided by SEQ ID NO:5, corresponding to Kabat amino acid residue numbers 221-447.

sites while preserving the amino acid sequence. In one embodiment, the codons for A231, P232, and E233 are modified from GCA, CCT, GAA to GCT, CCG, GAA in order to incorporate a BspEI restriction site without altering the expressed amino acid sequence. In another embodiment, the codons for G236, G237, and P238 are modified from GGG, GGA, CCG to GGC, GGA, CCG in order to incorporate a RsrII restriction site while preserving the amino acid sequence.

An Fc polypeptide of IgG can be modified according to well recognized procedures such as site-directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues (Kabat numbering convention) in human IgG1 Fc (Fcγ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F,

```
                                                        SEQS ID NO: 5
DKTHTCPPCP APELLGGPSV FLFPPKPKDT LMISRTPEVT CVVVDVSHED PEVKFNWYVD 60

GVEVHNAKTK PREEQYNSTY RVVSVLTVLH QDWLNGKEYK CKVSNKALPA PIEKTISKAK120

GQPREPQVYT LPPSRDELTK NQVSLTCLVK GFYPSDIAVE WESNGQPENN YKTTPPVLDS180

DGSFFLYSKL TVDKSRWQQG NVFSCSVMHE ALHNHYTQKS LSLSPGK                227
```

In one embodiment a nucleic acid encoding a Fc polypeptide from human IgG1 has a sequence provided by GenBank accession no. Y14735 (SEQ ID NO:62):

```
                               SEQ ID NO: 62
gacaaaactc acacatgccc accgtgccca gcacctgaac tcctgggggg accgtcagtc ttcctcttcc ccccaaaacc caaggacacc ctcatgatct cccggacccc tgaggtcaca tgcgtggtgg tggacgtgag ccacgaagac cctgaggtca agttcaactg gtacgtggac ggcgtggagg tgcataatgc caagacaaag ccgcgggagg agcagtacaa cagcacgtac cgtgtggtca gcgtcctcac cgtcctgcac caggactggc tgaatggcaa ggagtacaag tgcaaggtct ccaacaaagc cctcccagcc cccatcgaga aaaccatctc caaagccaaa gggcagcccc gagaaccaca ggtgtacacc ctgcccccat cccgggatga gctgaccaag aaccaggtca gcctgacctg cctggtcaaa ggcttctatc ccagcgacat cgccgtggag tgggagagca atgggcagcc ggagaacaac tacaagacca cgcctcccgt gctggactcc gacggctcct tcttcctcta cagcaagctc accgtggaca agagcaggtg gcagcagggg aacgtcttct catgctccgt gatgcatgag gctctgcaca accactacac gcagaagagc ctctccctgt ctccgggtaa a
```

The nucleotide sequence of the Fc polypeptide can be modified to incorporate or eliminate restriction endonuclease N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild-type proline substituted by alanine at position number 238. As an example, one specific embodiment, incorporates the N297A mutation, removing a highly conserved N-glycosylation site. In addition to alanine other amino acids may be substituted for the wild-type amino acids at the positions specified above. Mutations may be introduced singly into Fc giving rise to more than one hundred FcRn binding partners distinct from native Fc. Additionally, combinations of two, three, or more of these individual mutations may be introduced together, giving rise to hundreds more FcRn binding partners. Moreover, one of the polynucleotides of a dimeric Fc fragment or other dimeric FcRn binding partner may include a mutation while the other does not, or both may be mutated but with different mutations. Any of the mutations described herein, including N297A, may be used to modify Fc.

Certain of the above mutations may confer new functionality upon the FcRn binding partner. For example, one embodiment incorporates N297A, removing a highly conserved N-glycosylation site. The potential effect of this mutation is to reduce immunogenicity, thereby enhancing circulating half-life of the FcRn binding partner, and to render the FcRn binding partner incapable of binding to other Fc receptors including FcγRI, FcγRIIA, FcγRIIB, and FcγRIIIA, without compromising affinity for FcRn. Routledge E G et al. (1995) *Transplantation* 60:847-53; Friend P J et al. (1999) *Transplantation* 68:1632-7; Shields R L et al. (1995) *J Biol Chem* 276:6591-604. As a further example of new functionality arising from mutations described above, affinity for FcRn may be increased beyond that of wild-type in some instances. This increased affinity may reflect an increased "on" rate, a decreased "off" rate, or both an increased "on" rate and a decreased "off" rate. Mutations reported to impart an increased affinity for FcRn include T256A, T307A, E380A, and N434A. Shields et al. (2001) *J Biol Chem* 276: 6591.

Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 (ELLG; SEQ ID NO:6) to the corresponding sequence from IgG2 (PVA, with one amino acid deletion). It has been reported that FcγRI, FcγRII, and FcγRIII, which mediate various effector functions, will not bind to IgG1 when such mutations have been introduced. Ward E S et al. (1995) *Ther Immunol* 2:77-94; Armour K L et al. (1999) *Eur J Immunol* 29:2613-24.

As used herein, a proFIX-FcRn binding partner fusion protein refers to a fusion protein that includes a proFIX polypeptide covalently linked to an FcRn binding partner polypeptide. The proFIX polypeptide component is capable of being processed by PC5 to yield a mature form of FIX that in turn is capable of being activated by Factor XIa to yield an activated FIXa polypeptide. The FcRn binding partner polypeptide component can be any suitable polypeptide that can be specifically bound by FcRn. In certain embodiments the FcRn binding partner polypeptide is an Fc polypeptide of IgG or an Fc polypeptide of a human IgG. The linkage between the proFIX polypeptide component and the FcRn binding partner polypeptide component can be direct or it can be indirect via a linker.

As used herein, a proFIX-Fc fusion protein refers to a fusion protein that includes a proFIX polypeptide covalently linked to an Fc polypeptide. The proFIX polypeptide component is capable of being processed by PC5 to yield a mature form of FIX that in turn is capable of being activated by Factor XIa to yield an activated FIXa polypeptide. The Fc polypeptide component can be any suitable Fc polypeptide that can be specifically bound by FcRn. In certain embodiments the Fc polypeptide is an Fc polypeptide of IgG or an Fc polypeptide of a human IgG. The linkage between the proFIX polypeptide component and the Fc polypeptide component can be direct or it can be indirect via a linker.

Fusion proteins of the invention can include various dimeric structures formed through dimerization of identical or nonidentical polypeptides. Thus dimeric fusion proteins of the invention can include homodimers and heterodimers. In one embodiment, the fusion protein of the invention comprises a first polypeptide chain comprising at least a first domain, said first domain having at least one specific binding partner, and a second polypeptide chain comprising at least a second domain, wherein said second domain is a specific binding partner of said first domain. The fusion protein thus comprises a polypeptide capable of dimerizing with another polypeptide due to the interaction of the first domain and the second domain. Methods of dimerizing antibodies using heterologous domains are known in the art. See, e.g., U.S. Pat. Nos. 5,807,706 and 5,910,573; Kostelny et al. (1992) *J Immunol* 148:1547.

Dimerization can occur by formation of a covalent bond, or alternatively a non-covalent bond, e.g., hydrophobic interaction, Van der Waals forces, interdigitation of amphiphilic peptides such as, but not limited to, alpha helices, charge-charge interactions of amino acids bearing opposite charges, such as, but not limited to, lysine and aspartic acid, arginine and glutamic acid. In one embodiment, the dimerization involves a helix bundle comprising a helix, a turn, and another helix. In another embodiment, the dimerization involves a leucine zipper comprising a peptide having several repeating amino acids in which every seventh amino acid is a leucine residue. In one embodiment, the specific binding partners are Fos and Jun. See Branden et al. (1991) Introduction to Protein Structure, Garland Publishing, New York.

In another embodiment, dimerization is mediated by a chemical linkage (see, e.g., Brennan et al. (1985) *Science* 229:81). In this embodiment, intact immunoglobulins, or fusion proteins comprised of at least a portion of an immunoglobulin constant region, are cleaved to generate heavy chain fragments. These fragments are reduced in the presence of a dithiol complexing agent such as sodium arsenite to stabilize vicinal dithiols and prevent intermolecular disulfide formation. The fragments so generated are then converted to thionitrobenzoate (TNB) derivatives. One of the TNB derivatives is then reconverted to the heavy chain fragment thiol by reduction with a reducing agent such as mercaptoethylamine and is then mixed with an equimolar amount of the other TNB derivative to form a dimer.

As used herein, a proFIX-Fc homodimer refers to a covalently or noncovalently linked dimer formed between two identical proFIX-Fc polypeptides. In one embodiment the two polypeptides are covalently linked to one another so as to form a duplex structure in which the two polypeptides are co-aligned from N-terminus to C-terminus. In one embodiment the two polypeptides are covalently linked to one another through one or more disulfide bridges formed between the hinge domain region of one Fc polypeptide and the hinge domain region of the other Fc polypeptide, so as to form a duplex structure in which the Fc polypeptides are co-aligned from N-terminus to C-terminus. A diagram illustrating the structure of one embodiment of a proFIX-Fc homodimer is provided in FIG. 2A.

As used herein, a proFIX-Fc monomer-dimer hybrid refers to a heterodimeric protein that includes a first polypeptide chain and a second polypeptide chain, wherein the first polypeptide chain includes a proFIX polypeptide and at least a portion of an immunoglobulin constant chain capable of binding specifically to an FcRn, and wherein the second polypeptide chain includes at least a portion of an immunoglobulin constant chain capable of binding specifically to an FcRn but which second polypeptide chain does not include a proFIX polypeptide. Thus in this aspect of the invention the protein is monomeric with respect to proFIX and dimeric with respect to Fc (hence the term "monomer-dimer hybrid"). However, it should be appreciated that, while a proFIX-Fc monomer-dimer hybrid is heterodimeric since the two chains are distinct, these molecules may also be referred to as "monomer" for short since there is only one biologically active proFIX compared to traditional homodimeric Fc fusion proteins. Reference is made to US 2005/0032174, the entire content of which is incorporated herein by reference. In one embodiment the portion of an immunoglobulin constant chain capable of binding specifically to an FcRn includes, in each instance, an IgG Fc fragment domain. In one embodiment the portion of an immunoglobulin constant chain capable of binding specifically to an FcRn is, in each instance, an IgG Fc fragment domain. In one embodiment the portion of an immunoglobulin constant chain capable of binding specifically to an FcRn includes, in each instance, a human IgG Fc fragment domain. In one embodiment the portion of an immunoglobulin constant chain capable of binding specifically to an FcRn is, in each instance, a human IgG Fc fragment domain. In one embodiment the portion of an immunoglobulin constant chain capable of binding specifically to an FcRn in the first polypeptide chain is identical to the portion of an immunoglobulin constant chain capable of binding specifically to an FcRn in the second polypeptide chain. In one embodiment the portion of an immunoglobulin constant chain capable of binding specifically to an FcRn in the first polypeptide chain is not identical to the portion of an immunoglobulin constant chain capable of binding specifically to an FcRn in the second polypeptide chain. A diagram illustrating the structure of one embodiment of a proFIX-Fc monomer-dimer hybrid is provided in FIG. 2B.

The fusion proteins and conjugates of the invention can optionally comprise at least one linker molecule. A linker generally can be comprised of any organic molecule. In one embodiment, the linker is polyethylene glycol (PEG). In another embodiment, the linker is comprised of amino acids. An amino acid linker can comprise 1-5 amino acids, 1-10 amino acids, 1-20 amino acids, 10-50 amino acids, 50-100 amino acids, 100-200 amino acids. An amino acid linker in one embodiment can be encoded by a nucleic acid sequence incorporated into a nucleic acid molecule encoding a fusion protein. An amino acid linker in one embodiment can be generated as an isolated synthetic peptide, i.e., a peptide produced using known chemical synthesis techniques (e.g., solid phase synthesis) performed outside of a cell. Any of the amino acid linkers described herein may be used in a fusion protein of the invention, e.g., a proFIX-Fc monomer-dimer hybrid.

In one embodiment, an amino acid linker is the eight amino acid linker EFAGAAAV (SEQ ID NO:7), wherein E represents glutamic acid, F represents phenylalanine, A represents alanine, G represents glycine, and V represents valine. In one embodiment the linker is encoded by a nucleic acid sequence that is incorporated into a nucleic acid molecule encoding a fusion protein.

An amino acid linker in certain embodiments can include the sequence $G_n$ (SEQ ID NO:8), $(GA)_n$ (SEQ ID NO:9), $(GUS)_n$ (SEQ ID NO:10), $(GGGGS)_n$ (SEQ ID NO:11), or any combination thereof, wherein in each instance G represent glycine, A represents alanine, S represents serine, and n may be an integer from 1-10, i.e., 1, 2, 3, 4, 5, 6, 7, 8, 9, 10. Examples of linkers include, but are not limited to, GGG, SGGSGGS (SEQ ID NO:12), GGSGGSGGSGGSGGG (SEQ ID NO:13), GGSGGSGGGGSGGGGS (SEQ ID NO:14), GGSGGSGGSGGSGGS (SEQ ID NO:15). In one embodiment the linker is GGGGSGGGGSGGGGSGGGGSGGGGSGGGGS (SEQ ID NO:16). In one embodiment the linker is encoded by a nucleic acid sequence that is incorporated into a nucleic acid molecule encoding a fusion protein. The linker does not eliminate or diminish the biological activity of the fusion protein. Optionally, the linker enhances the biological activity of the fusion protein, e.g., by further diminishing the effects of steric hindrance and making the FIX component and/or other component more accessible.

The linker may also incorporate a moiety capable of being cleaved either chemically (e.g., hydrolysis of an ester bond), enzymatically (e.g., incorporation of a protease cleavage sequence) or photolytically (e.g., a chromophore such as 3-amino-3-(2-nitrophenyl) proprionic acid (ANP)) in order to release the biologically active molecule from the Fc protein.

The chemistry of cross-linking and effective reagents for such purposes are well known in the art. The nature of the crosslinking reagent used to conjugate various components is not restricted by the invention. Any crosslinking agent may be used provided that a) the activity of the FIX is retained, and b) binding by the FcRn of the FcRn binding partner component of the conjugate is not adversely affected.

An example of an effective one-step crosslinking of Fc and a compound is oxidation of Fc with sodium periodate in sodium phosphate buffer for 30 minutes at room temperature, followed by overnight incubation at 4° C. with the compound to be conjugated. Conjugation also may be performed by derivatizing both the compound and Fc fragments with sulfosuccinimidyl 6-[3-(2-pyridyldithio)propionamide]hexanoate (sulfo-LC-SPDP, Pierce) for 18 hours at room temperature. Conjugates also may be prepared by derivatizing Fc fragments and the desired compound to be delivered with different crosslinking reagents that will subsequently form a covalent linkage. An example of this reaction is derivatization of Fc fragments with sulfosuccinimidyl 4-(N-maleimidomethyl)cyclo-hexane-1-carboxylate (Sulfo-SMCC, Pierce) and the compound to be conjugated to Fc is thiolated with N-succinimidyl S-acetylthioacetate (SATA). The derivatized components are purified free of crosslinker and combined at room temperature for one hour to allow crosslinking. Other crosslinking reagents comprising aldehyde, imide, cyano, halogen, carboxyl, activated carboxyl, anhydride, and maleimide functional groups are known to persons of ordinary skill in the art and also may be used for conjugation of compounds to Fc fragments.

The choice of cross-linking reagent will, of course, depend on the nature of the components desired to be conjugated. The crosslinking reagents described above are effective for protein-protein conjugations. If a carbohydrate or carbohydrate-containing moiety is to be conjugated to a polypeptide, then heterobifunctional crosslinking reagents such as ABH, M2C2H, MPBH and PDPH are useful for conjugation (Pierce Chemical Co., Rockford, Ill.). Another method of conjugating proteins and carbohydrates is disclosed by Brumeanu et al. (*Genetic Engineering News*, Oct. 1, 1995, p. 16). If a lipid or a lipid-containing moiety is to be conjugated to a polypeptide, then crosslinkers such as SPDP, SMPB, and derivatives thereof may be used (Pierce Chemical Co., Rockford, Ill.).

In all of the above crosslinking reactions it is important to purify the derivatized compounds free of crosslinking reagent. It is important also to purify the final conjugate substantially free of unconjugated reactants. Purification may be achieved by affinity, gel filtration or ion exchange chromatography based on the properties of either component of the conjugate. A particularly preferred method is an initial affinity purification step using protein A-Sepharose to retain Fc and Fc-containing conjugates, followed by gel filtration or ion exchange chromatography based on the mass, size or charge of the Fc conjugate. The initial step of this purification scheme ensures that the conjugate will bind to FcRn which is an essential requirement of the invention.

It has been discovered according to the invention that PC5 can be used to process a FIX precursor polypeptide to yield a mature FIX polypeptide. In one embodiment both the PC5 and the FIX precursor polypeptide are expressed within a cell, where the PC5 processes the FIX precursor polypeptide. In another embodiment an isolated PC5 can be used to process an isolated FIX precursor polypeptide.

When the PC5 and the FIX precursor polypeptide are to be coexpressed within a cell, in one embodiment the cell naturally expresses PC5 and contains an expression vector encoding a proprotein of Factor IX (proFIX), or a fusion protein thereof.

When the PC5 and the FIX precursor polypeptide are to be coexpressed within a cell, in one embodiment the cell contains an expression vector encoding a proprotein of Factor IX (proFIX), or a fusion protein thereof, and the cell is modified by homologous recombination to include a nucleic acid expression control sequence that causes overexpression of an endogenous PC5 gene. In this embodiment an exogenous, more potent promoter is exchanged for the endogenous PC5 promoter, resulting in overexpression of endogenous PC5. See, e.g., U.S. Pat. Nos. 5,641,670, 5,733,761, and 5,272,071; WO 91/06666; WO 91/06667; and WO 90/11354, all of which are incorporated by reference in their entirety.

When the PC5 and the FIX precursor polypeptide are to be coexpressed within a cell, in one embodiment the cell contains an expression vector encoding a proprotein of Factor IX (proFIX), or a fusion protein thereof, and an expression vector encoding a functional PC5 polypeptide. The expression vector encoding a proprotein of Factor IX (proFIX), or a fusion protein thereof, and the expression vector encoding a functional PC5 polypeptide can be separate expression vectors or can be combined in a single expression vector.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the invention will include a polynucleotide encoding a polypeptide of the invention, e.g., PC5 and proFIX. As used herein, a polynucleotide refers to any covalently linked polymer of two or more nucleotides. A nucleotide is a molecule composed of a sugar (e.g., ribose or deoxyribose) linked to a phosphate group and a nucleobase, i.e., either a purine or a pyrimidine. Purines include but are not limited to adenine and guanine. Pyrimidines include but are not limited to cytosine, thymine, and uracil. In one embodiment a polynucleotide is a polymer of deoxyribonucleotides, i.e., a DNA molecule. In one embodiment a polynucleotide is a polymer of ribonucleotides, i.e., an RNA molecule. A polynucleotide in one embodiment is a nucleic acid molecule that encodes a polypeptide, i.e., the polynucleotide is a coding sequence. In one embodiment a nucleic acid molecule that encodes a polypeptide is a genomic DNA molecule that encodes the polypeptide. In one embodiment a nucleic acid molecule that encodes a polypeptide is a complementary DNA (cDNA) molecule that encodes the polypeptide. In one embodiment a polynucleotide is a recombinant DNA molecule that encodes a polypeptide.

In certain embodiments a coding sequence is operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired protein or polypeptide.

A gene expression control sequence as used herein is any regulatory nucleotide sequence, such as a promoter sequence or promoter-enhancer combination, which facilitates the efficient transcription and translation of the coding nucleic acid to which it is operably linked. The gene expression control sequence may, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression control sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined coding nucleic acid. The gene expression sequences optionally include enhancer sequences or upstream activator sequences as desired.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, Calif.). Other plasmids are well-known to those of ordinary skill in the art. Additionally, plasmids may be custom designed using standard molecular biology techniques to remove and/or add specific fragments of DNA.

In one insect expression system that may be used to produce the proteins of the invention, *Autographa californica* nuclear polyhedrosis virus (AcNPV) is used as a vector to express the foreign genes. The virus grows in *Spodoptera frugiperda* cells. A coding sequence may be cloned into nonessential regions (for example, the polyhedron gene) of the virus and placed under control of an ACNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (see, e.g., Smith et al. (1983) *J Virol* 46:584; U.S. Pat. No. 4,215,051). Further examples of this expression system may be found in Ausubel et al., eds. (1989) Current Protocols in Molecular Biology, Vol. 2, Greene Publish. Assoc. & Wiley Interscience.

Another system which can be used to express the proteins of the invention is the glutamine synthetase gene expression system, also referred to as the "GS expression system" (Lonza Biologics PLC, Berkshire UK). This expression system is described in detail in U.S. Pat. No. 5,981,216.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. See, e.g., Logan & Shenk (1984) *Proc Natl Acad Sci USA* 81:3655). Alternatively, the vaccinia 7.5 K promoter may be used. See, e.g., Mackett et al. (1982) *Proc Natl Acad Sci USA* 79:7415; Mackett et al. (1984) *J Virol* 49:857; Panicali et al. (1982) *Proc Natl Acad Sci USA* 79:4927.

To increase efficiency of production, the polynucleotides can be designed to encode multiple units of the protein of the invention separated by enzymatic cleavage sites. The resulting polypeptide can be cleaved (e.g., by treatment with the appropriate enzyme) in order to recover the polypeptide units. This can increase the yield of polypeptides driven by a single promoter. When used in appropriate viral expression systems, the translation of each polypeptide encoded by the mRNA is directed internally in the transcript; e.g., by an internal ribosome entry site, IRES. Thus, the polycistronic construct directs the transcription of a single, large polycistronic mRNA which, in turn, directs the translation of multiple, individual polypeptides. This approach eliminates the production and enzymatic processing of polyproteins and may significantly increase yield of polypeptide driven by a single promoter.

Vectors used in transformation will usually contain a selectable marker used to identify transformants. In bacterial systems, this can include an antibiotic resistance gene such as ampicillin or kanamycin. Selectable markers for use in cultured mammalian cells include genes that confer resistance to drugs, such as neomycin, hygromycin, and methotrexate. The selectable marker may be an amplifiable selectable marker. One amplifiable selectable marker is the dihydrofolate reductase (DHFR) gene. Simonsen C C et al. (1983) *Proc Natl Acad Sci USA* 80:2495-9. Selectable markers are reviewed by Thilly (1986) Mammalian Cell Technology, Butterworth Publishers, Stoneham, Mass., and the choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, U.S. Pat. No. 4,713,339).

The expression vectors can encode for tags that permit for easy purification of the recombinantly produced protein. Examples include, but are not limited to vector pUR278 (Ruther et al. (1983) *EMBO J.* 2:1791) in which coding sequences for the protein to be expressed may be ligated into the vector in frame with the lac z coding region so that a tagged fusion protein is produced; pGEX vectors may be used to express proteins of the invention with a glutathione S-transferase (GST) tag. These proteins are usually soluble and can easily be purified from cells by adsorption to glutathione-agarose beads followed by elution in the presence of free glutathione. The vectors include cleavage sites (thrombin or Factor Xa protease or PreScission Protease™ (Pharmacia, Peapack, N.J.)) for easy removal of the tag after purification.

The expression vector or vectors are then transfected or co-transfected into a suitable target cell, which will express the polypeptides. Transfection techniques known in the art include, but are not limited to, calcium phosphate precipitation (Wigler et al. (1978) *Cell* 14:725), electroporation (Neumann et al. (1982) *EMBO J.* 1:841), and liposome-based reagents. A variety of host-expression vector systems may be utilized to express the proteins described herein including both prokaryotic or eukaryotic cells. These include, but are not limited to, microorganisms such as bacteria (e.g., *E. coli*) transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems, including mammalian cells (e.g., HEK 293, CHO, Cos, HeLa, and BHK cells).

In one embodiment the host cell is a eukaryotic cell. As used herein, a eukaryotic cell refers to any animal or plant cell having a definitive nucleus. Eukaryotic cells of animals include cells of vertebrates, e.g., mammals, and cells of invertebrates, e.g., insects. Eukaryotic cells of plants specifically can include, without limitation, yeast cells. A eukaryotic cell is distinct from a prokaryotic cell, e.g., bacteria.

In certain embodiments the eukaryotic cell is a mammalian cell. A mammalian cell is any cell derived from a mammal. Mammalian cells specifically include but are not limited to mammalian cell lines. In one embodiment the mammalian cell is a human cell. In one embodiment the mammalian cell is a HEK 293 cell, which is a human embryonic kidney cell line. HEK 293 cells are available as CRL-1533 from American Type Culture Collection, Manassas, Va., and as 293-H cells, Catalog No. 11631-017 or 293-F cells, Catalog No. 11625-019 from Invitrogen (Carlsbad, Calif.). In one embodiment the mammalian cell is a PER.C6® cell, which is a human cell line derived from retina. PER.C6® cells are available from Crucell (Leiden, The Netherlands). In one embodiment the mammalian cell is a Chinese hamster ovary (CHO) cell. CHO cells are available from American Type Culture Collection, Manassas, Va. (e.g., CHO-K1; CCL-61). In one embodiment the mammalian cell is a baby hamster kidney (BHK) cell. BHK cells are available from American Type Culture Collection, Manassas, Va. (e.g., CRL-1632).

In one embodiment a plasmid including a proFIX-Fc fusion coding sequence and a selectable marker, e.g., zeocin resistance, is transfected into HEK 293 cells, for production of FIX-Fc homodimer.

In one embodiment a first plasmid including a proFIX-Fc fusion coding sequence and a first selectable marker, e.g., a zeocin resistance gene, and a second plasmid including an Fc coding sequence and a second selectable marker, e.g., a neomycin resistance gene, are cotransfected into HEK 293 cells, for production of FIX-Fc monomer-dimer hybrid. The first and second plasmids can be introduced in equal amounts (i.e., 1:1 ratio), or they can be introduced in unequal amounts.

In one embodiment a first plasmid including a proFIX-Fc fusion coding sequence and a first selectable marker, e.g., a zeocin resistance gene, and a second plasmid including an Fc coding sequence and a second selectable marker, e.g., a neomycin resistance gene, and a third plasmid including a PC5 coding sequence and a third selectable marker, e.g., a hygromycin resistance gene, are cotransfected into HEK 293 cells, for production of FIX-Fc monomer-dimer hybrid. The first and second plasmids can be introduced in equal amounts (i.e., 1:1 molar ratio), or they can be introduced in unequal amounts.

In one embodiment a first plasmid, including a proFIX-Fc fusion coding sequence, an Fc coding sequence, and a first selectable marker, e.g., a zeocin resistance gene, and a second plasmid including a PC5 coding sequence and a second selectable marker, e.g., a hygromycin resistance gene, are cotransfected into HEK 293 cells, for production of FIX-Fc monomer-dimer hybrid. The promoters for the proFIX-Fc fusion coding sequence and the Fc coding sequence can be different or they can be the same.

In one embodiment a first plasmid, including a proFIX-Fc fusion coding sequence, an Fc coding sequence, and a first selectable marker, e.g., a zeocin resistance gene, and a second plasmid including an Fc coding sequence and a second selectable marker, e.g., a neomycin resistance gene, and a third plasmid including a PC5 coding sequence and a third selectable marker, e.g., a hygromycin resistance gene, are cotransfected into HEK 293 cells, for production of FIX-Fc monomer-dimer hybrid. The promoters for the proFIX-Fc fusion coding sequence and the Fc coding sequence in the first plasmid can be different or they can be the same. The first and second plasmids can be introduced in equal amounts (i.e., 1:1 molar ratio), or they can be introduced in unequal amounts.

In one embodiment, a truncated form of the FIX intron I (GenBank accession no. NC_000023) is included within the coding sequence of FIX. This has previously been shown to increase the level of FIX expression due to functional splicing sequences to present in the precursor mRNA. Kurachi S et al. (1995) *J Biol Chem.* 270:5276-81.

In one embodiment transfected cells are stably transfected. These cells can be selected and maintained as a stable cell line, using conventional techniques known to those of skill in the art.

Host cells containing DNA constructs of the protein are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals, and growth factors. Optionally the media can contain one or more selection factors. Optionally the media can contain bovine calf serum or fetal calf serum (FCS). In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g., MEM, DMEM, DMEM/F12). In one embodiment the medium is CD293 (Invitrogen, Carlsbad, Calif.). In one embodiment, the medium is CD17 (Invitrogen, Carlsbad, Calif.). Selection of a medium appropriate for the particular cell line used is within the level of ordinary skill in the art.

In one aspect the invention provides a method for producing a mature Factor IX-containing polypeptide from a pro-protein of Factor IX, or a fusion protein thereof.

As used herein, a mature Factor IX-containing polypeptide refers to a polypeptide that includes a mature form of Factor IX. In one embodiment a mature Factor IX-containing polypeptide refers to a polypeptide that is a mature form of Factor IX. A mature form of Factor IX includes at least a γ-carboxylated Gla domain and a catalytic domain, and excludes both a prepeptide and a propeptide, as described herein. The mature form of Factor IX can but need not necessarily be an activated form of Factor IX. For example, in one embodiment a mature form of Factor IX is represented by amino acid residues 47-461 of SEQ ID NO:3. In one embodiment at least ten of the twelve glutamic acid residues in the Gla domain are gamma carboxylated. When only ten of the twelve glutamic acid residues in the Gla domain are gamma carboxylated, in one embodiment the ten carboxylated glutamic residues are the first ten glutamic acid residues in the Gla domain (e.g., Glu53, Glu54, Glu61, Glu63, Glu66, Glu67, Glu72, Glu73, Glu76, and Glu79 in SEQ ID NO:3). In one embodiment at least eleven of the twelve glutamic acid residues in the Gla domain are gamma carboxylated. In one embodiment all of the glutamic acid residues in the Gla domain are gamma carboxylated.

In one embodiment according to this aspect of the invention, a mature Factor IX-containing polypeptide refers to a polypeptide that is a mature form of Factor IX.

In one embodiment according to this aspect of the invention, the mature Factor IX-containing polypeptide is a FIX-Fc monomer-dimer hybrid, such as is disclosed in co-owned U.S. patent application Ser. No. 10/841,250, published as US 2005/0032174, the entire content of which is incorporated herein by reference. In this embodiment the proproprotein fusion protein corresponds to a proFIX-Fc monomer-dimer hybrid.

Also provided is a mature FIX-Fc monomer-dimer hybrid produced according to the method of this aspect of the invention.

The method for producing mature Factor IX-containing polypeptide entails culturing cells containing a first expression vector encoding a proprotein of Factor IX, or a fusion protein thereof, and a second expression vector encoding a functional PC5 polypeptide, as described above. The cells are cultured under conditions that allow expression of both the proFIX or the fusion protein thereof and the functional PC5 polypeptide.

As used herein, culturing refers to maintaining living cells in vitro for at least a definite time. Maintaining can but need not include an increase in population of living cells. For example, cells maintained in culture can be static in population but still viable and capable of producing a desired product, e.g., a recombinant protein or recombinant fusion protein. Suitable conditions for culturing eukaryotic cells are well known in the art and include appropriate selection of culture media, media supplements, temperature, pH, oxygen saturation, and the like. For commercial purposes culturing can include the use of any of various types of scale-up systems including shaker flasks, roller bottles, hollow fiber bioreactors, stirred-tank bioreactors, airlift bioreactors, Wave bioreactors, and others.

The cell culture conditions are also selected to allow processing of the proFIX or fusion protein thereof by the functional PC5 polypeptide. Conditions that allow processing of the proFIX or fusion protein thereof by the functional PC5 polypeptide specifically may include the presence of a source of vitamin K. For example, in one embodiment stably transfected HEK 293 cells are cultured in CD293 media (Invitrogen, Carlsbad, Calif.) supplemented with 4 mM glutamine and 10 μg/L vitamin $K_3$.

As used herein, processing by functional PC5 refers to cleavage of propeptide from proFIX. In other words, processing by functional PC5 refers to the PC5-mediated conversion of a proFIX-containing polypeptide to a mature Factor IX-containing polypeptide.

The invention in one aspect relates to a method for increasing yield of a mature Factor IX-containing polypeptide from a proprotein of Factor IX, or a fusion protein thereof. As used herein with respect to mature Factor IX-containing polypeptide, increasing yield refers to inducing a measurable increase in amount or activity of a mature Factor IX-containing polypeptide, obtained with PC5 and under specified conditions, as compared to a reference amount or activity of the mature Factor IX-containing polypeptide, obtained without PC5 and under the specified conditions. In one embodiment the measurable increase is at least 5 percent. In one embodiment the measurable increase is at least 10 percent. In additional individual embodiments the measurable increase is at least 20 percent, at least 30 percent, at least 40 percent, at least 50 percent, at least 60 percent, at least 70 percent, at least 80 percent, at least 90 percent, or at least 100 percent.

The invention in one aspect relates to a method for producing a mature Factor IX-containing polypeptide from a proprotein of Factor IX, or a fusion protein thereof. As used herein, producing a mature Factor IX-containing polypeptide from a proprotein of Factor IX, or a conjugate thereof, refers to processing the proFIX or the conjugate thereof with PC5 to yield a mature Factor IX-containing polypeptide.

As used herein, a conjugate refers to any two or more entities bound to one another by any physicochemical means, including, but not limited to, hydrophobic interaction, covalent interaction, hydrogen bond interaction, ionic interaction, and any combination thereof. Thus in one embodiment a conjugate of the invention refers to any two or more entities bound to one another by covalent interaction. For example, in one embodiment a conjugate is a fusion protein. In one embodiment a conjugate of the invention refers to any two or more entities bound to one another by noncovalent interaction.

The method according to this aspect of the invention involves contacting the proFIX or the conjugate thereof with an effective amount of functional PC5 polypeptide. Contacting refers to bringing the various entities into intimate physical contact, e.g., so as to permit PC5 to process the proFIX or the conjugate thereof. An effective amount, as used herein, refers to an amount that is sufficient to achieve a desired biological effect, e.g., processing of the proFIX or the conjugate thereof by PC5.

In one embodiment the method according to this aspect of the invention can be practiced using an isolated proprotein of Factor IX, or a conjugate thereof, and an isolated PC5 polypeptide. For example, an isolated proprotein of Factor IX derived from one source can be contacted with an isolated PC5 polypeptide derived from another source, under conditions that allow processing of the proFIX or fusion protein thereof by the functional PC5 polypeptide. Conditions that allow processing of the proFIX or fusion protein thereof by the functional PC5 polypeptide include the presence of a source of vitamin K, gamma carboxylase, and additional components and conditions suitable for gamma carboxylase enzymatic activity.

In one embodiment according to this aspect of the invention, the mature Factor IX-containing polypeptide is a FIX-Fc monomer-dimer hybrid, such as is disclosed in co-owned U.S. patent application Ser. No. 10/841,250, published as US 2005/0032174, the entire content of which is incorporated herein by reference. In this embodiment the proFIX conjugate corresponds to a proFIX-Fc monomer-dimer hybrid.

Also provided is a mature FIX-Fc monomer-dimer hybrid produced according to the method of this aspect of the invention.

As used herein, PEGylated proFIX refers to a conjugate formed between proFIX and at least one polyethylene glycol (PEG) molecule. PEG is commercially available in a large variety of molecular weights and average molecular weight ranges. Typical examples of PEG average molecular weight ranges include, but are not limited to, 200, 300, 400, 600, 1000, 1300-1600, 1450, 2000, 3000, 3000-3750, 3350, 3000-7000, 3500-4500, 5000-7000, 7000-9000, 8000, 10000, 8500-11500, 16000-24000, 35000, and 40000. These average molecular weights are provided merely as examples and are not meant to be limiting in any way.

In one embodiment, the peptide of the invention may be PEGylated to include mono- or poly- (e.g., 2-4) PEG moieties. PEGylation may be carried out by any of the PEGylation reactions known in the art. Methods for preparing a PEGylated protein product will generally include (a) reacting a polypeptide with polyethylene glycol (such as a reactive ester or aldehyde derivative of PEG) under conditions whereby the peptide of the invention becomes attached to one or more PEG groups; and (b) obtaining the reaction product(s). In general, the optimal reaction conditions for the reactions will be determined case by case based on known parameters and the desired result.

There are a number of PEG attachment methods available to those skilled in the art, for example, EP 0 401 384; Malik F et al. (1992) *Exp Hematol.* 20:1028-35; Francis (1992) *Focus on Growth Factors* 3(2):4-10; EP 0 154 316; EP 0 401 384; WO 92/16221; and WO 95/34326.

The step of PEGylation as described for the proteins of the invention may be carried out via an acylation reaction or an alkylation reaction with a reactive polyethylene glycol molecule. Thus, protein products according to the present invention include PEGylated proteins wherein the PEG group(s) is (are) attached via acyl or alkyl groups. Such products may be mono-PEGylated or poly-PEGylated (for example, those containing 2-6 or 2-5 PEG groups). The PEG groups are generally attached to the protein at the α- or ε-amino groups of amino acids, but it is also contemplated that the PEG groups can be attached to any amino group attached to the protein that is sufficiently reactive to become attached to a PEG group under suitable reaction conditions.

PEGylation by acylation generally involves reacting an active ester derivative of polyethylene glycol with a peptide of the invention. For acylation reactions, the polymer(s) selected typically have a single reactive ester group. Any known or subsequently discovered reactive PEG molecule may be used to carry out the PEGylation reaction. An example of a suitable activated PEG ester is PEG esterified to N-hydroxysuccinimide (NHS). As used herein, acylation is contemplated to include, without limitation, the following types of linkages between the therapeutic protein and a polymer such as PEG: amide, carbamate, urethane, and the like. See, for example, Charnow S M et al. (1994) *Bioconjug Chem.* 5:133-40. Reaction conditions may be selected from any of those known in the PEGylation art or those subsequently developed, but should avoid conditions such as temperature, solvent, and pH that would inactivate the polypeptide to be modified.

PEGylation by acylation will generally result in a poly-PEGylated protein. The connecting linkage may be an amide. The resulting product may be substantially only (e.g., >95%) mono-, di- or tri-PEGylated. However, some species with higher degrees of PEGylation may be formed in amounts depending on the specific reaction conditions used. If desired, more purified PEGylated species may be separated from the mixture (particularly unreacted species) by standard purification techniques, including among others, dialysis, salting-out, ultrafiltration, ion-exchange chromatography, gel filtration chromatography and electrophoresis.

PEGylation by alkylation generally involves reacting a terminal aldehyde derivative of PEG with a polypeptide in the presence of a reducing agent. For the reductive alkylation reaction, the polymer(s) selected should have a single reactive aldehyde group. An exemplary reactive PEG aldehyde is polyethylene glycol propionaldehyde, which is water stable, or mono C1-C10 alkoxy or aryloxy derivatives thereof. See, for example, U.S. Pat. No. 5,252,714.

Recombinantly produced FIX can be isolated from cells, culture media, and other products, for use in vitro and in vivo, including clinical use.

When proteins are produced according to the methods of the invention, they can occur in a mixture of molecules such as other proteins or protein fragments. For example, the FIX-Fc monomer-dimer hybrids generally are expressed in a mixture of products which also include FIX-Fc dimers and Fc dimers. The invention thus can involve methods of isolating any of the proteins described supra from a mixture containing the proteins. In particular, in one embodiment the invention can involve methods for isolating a proFIX-Fc monomer-dimer hybrid from a mixture of proteins including the monomer-dimer hybrid, a dimer, and at least a portion of an immunoglobulin constant region, e.g., an Fc fragment. In one embodiment the invention can involve methods for isolating a proFIX-Fc homodimer from a mixture of proteins including the monomer-dimer hybrid, a dimer, and at least a portion of an immunoglobulin constant region, e.g., an Fc.

In one embodiment protein product is secreted into the media. Media is separated from the cells, concentrated, filtered, and then passed over two or three affinity columns: a protein A column and one or two anion exchange columns.

In a typical example cells are separated from medium by centrifugation in disposable bottles. The separated medium is then filtered through 0.8/0.2 μM PALL AcroPak filters, and concentrated 5-7 fold with a Millipore ProFlux M12 tangential flow filtration system, Pellicon 2 cassettes, 10 K, B10-A, 0.5 m². Retentate is filtered using 0.8/0.2 μm PALL AcroPak filter into sterile plastic bags.

Protein A column (MabSelect, Amersham) is equilibrated with PBS, pH 7.4. The column is loaded with 10-15 mg protein/mL of resin at a flow rate of 150-200 cm/hour and washed with PBS followed 3-5 column volumes of PBS plus 0.9 M NaCl. Prior to elution the conductivity is lowered with PBS. The column is then eluted with 25 mM sodium citrate/150 mM NaCl, pH 3.4, and fractions are neutralized with 2M Tris to a final pH of 7. Resulting eluate contains all Fc-containing species.

Eluate from the Protein A column are loaded onto a DEAE column (Fractogel, EMD) and the column is equilibrated with 25 mM Tris/150 mM NaCl, pH 7.5. After washing the loaded and equilibrated column with 3-5 column volumes of 25 mM Tris/350 mM ammonium acetate, pH 7.5, the column is eluted with 25 mM Tris/600 mM ammonium acetate, pH 7.5. The eluate contains FIX-Fc monomer-dimer hybrid, free of FIX-Fc dimer and Fc fragments.

Although the purity of FIX-Fc monomer-dimer hybrid is already about 98 percent following DEAE chromatography, as a further step to enrich clotting activity of the isolated FIX-Fc monomer-dimer hybrid, a second ion exchange chromatography step can be used. Eluate from the previous step is diluted 1:4 with 25 mM Tris/150 mM NaCl, pH 7.5, and loaded onto a Q Sepharose FF column (Amersham) at 7-10 mg/ml. After washing the column with equilibration buffer, the column is eluted with 7 mM CaCl$_2$/150 mM NaCl/25 mM Tris, pH 7.5. Eluted FIX-Fc monomer-dimer hybrid is collected until the UV signal falls to about 20 percent of the maximum absorbance at 280 nm. Less active FIX-Fc monomer-dimer hybrid can be stripped off the column with higher concentration of either CaCl$_2$ (e.g., 10 mM) or ammonium acetate (e.g. 600 mM). Alternative and additional methods of purification and enrichment are known in the field, e.g., U.S. Pat. Nos. 4,981,952 and 5,714,583.

Using peptide mapping, it is possible to show propeptide is completely processed from FIX-Fc monomer-dimer hybrid by PC5. Tryptic digest (LysC, ArgC) of FIX-Fc monomer-dimer hybrid generates a marker for propeptide (propeptide indicator peptide, "PIP") if FIX propeptide is not fully processed. The FIX propeptide has an amino acid sequence TVFLDHENANKILNRPKR (SEQ ID NO:17), of which the sequence TVFLDHENANK (SEQ ID NO:18) represents the propeptide indicator peptide (PIP). PIP is present in FIX-Fc monomer-dimer hybrid transfected without processing enzyme (PC5), and it is absent in FIX-Fc monomer-dimer hybrid transfected with processing enzyme (PC5). PIP is also present in FIX-Fc monomer-dimer hybrid transfected with PC7, and absent in FIX alone transfected with PACE. In contrast, a reference peptide ("K23" corresponding to amino acid residues 395-400 of SEQ ID NO:3), having the sequence YGIYTK (SEQ ID NO:19), is present in FIX-Fc monomer-dimer hybrid transfected either with or without processing enzyme (PC5).

The activity of mature, activated FIX and FIX-containing polypeptides of the invention can be measured using a standard activated partial thromboplastin time (aPTT) assay. This assay is widely used as a clinical assay for Factor IX clotting activity. To perform the assay, a test sample is preincubated in FIX-deficient plasma with phospholipids and an activator such as ellagic acid or silica, and then clot formation is induced by addition of CaCl$_2$. The time to clot formation is measured, e.g., with an MLA Electra 1600 clinical instrument, and compared to a World Health Organization (WHO) Factor IX standard.

A particular advantage of FIX-Fc fusion proteins and conjugates over FIX alone is their extended half-life in vivo. The extended half-life permits a radically reduced dosing requirement compared to FIX alone. For example, in one experiment HEK 293-derived FIX-Fc monomer-dimer hybrid was found to have a terminal half-life of 30.0 hours following intravenous injection into normal rats. By comparison, the terminal half-life of BeneFIX® was found to be 5 hours following intravenous injection into normal rats. In a separate set of experiments in normal dogs, the terminal half-lives of FIX-Fc monomer-dimer hybrid and BeneFIX® were found to be 36 hours and 12-14 hours, respectively, following intravenous administration. Surprisingly, the half-life of FIX-Fc dimer in this set of experiments in dogs was found to be 22 hours. In all these experiments, pharmacokinetic measurements were performed using enzyme-linked immunosorbent assay (ELISA) specific for FIX.

In addition to the ELISA-based results showing extended in vivo half-life of FIX-Fc monomer-dimer hybrid, functional activity of FIX-Fc monomer-dimer hybrid was also shown to be extended by measuring aPTT in FIX-deficient mice. Following a single intravenous dose of FIX-Fc monomer-dimer hybrid (217 IU/kg body weight), the aPTT activity in plasma was shown to decay with a half-life of 47 hours in FIX-deficient mice.

The invention relates in part to a method of treating a subject having a hemostatic disorder comprising administering a therapeutically effective amount of at least one FIX polypeptide produced according to one or more methods of the invention. In particular, the fusion proteins and conjugates of the invention can be used to treat or prevent a hemostatic disorder associated with FIX deficiency, by promoting the formation of a fibrin clot. A hemostatic disorder that may be treated by administration of the fusion protein or conjugate of the invention includes, but is not limited to, hemophilia B.

A FIX protein or conjugate of the invention can be used prophylactically to treat a subject with a hemostatic disorder. Alternatively or in addition, a FIX fusion protein or conjugate of the invention of the invention can be used to treat an acute bleeding episode in a subject with a hemostatic disorder. In one embodiment, the hemostatic disorder is the result of an inherited deficiency in Factor IX. In another embodiment the hemostatic disorder can be an acquired disorder. The acquired disorder can result from an underlying secondary disease or condition. The secondary disease or condition can be, for example and without limitation, liver disease, disseminated intravascular coagulation (DIC), sepsis or infection, a cancer, an autoimmune disease, pregnancy, advanced age, or from medication to treat an underlying secondary disorder (e.g., cancer chemotherapy).

The FIX proteins and FIX conjugates of the invention can be administered via any suitable route of administration, including intravenously, subcutaneously, intramuscularly, or via any mucosal surface, e.g., orally, sublingually, buccally, sublingually, nasally, rectally, vaginally or via pulmonary route. The FIX proteins and conjugates of the invention can optionally be implanted within or linked to a biopolymer solid support that allows for the slow release of the FIX protein or conjugate to the desired site.

FIX-FcRn binding partner fusion proteins and other FcRn binding partner-containing conjugates in particular are well suited for delivery to any epithelial surface that expresses FcRn. Such epithelial surfaces include but are not limited to oral, gastric, intestinal, intrabiliary, intranasal, and pulmonary including in particular large airways.

The dose of the FIX protein or conjugate of the invention will vary depending on the subject and upon the particular route of administration used. Dosages can range from 0.1 to 100,000 µg/kg body weight. In one embodiment, the dosing range is 0.1-2,000 µg/kg. The protein or conjugate can be administered continuously or at specific timed intervals. In vitro assays may be employed to determine optimal dose ranges and/or schedules for administration. Additionally, effective doses may be extrapolated from dose-response curves obtained from animal models.

For clinical use the FIX proteins and conjugates of the invention can be formulated with any suitable pharmaceutical carrier. Examples of suitable pharmaceutical carriers are described in Remington's Pharmaceutical Sciences by E. W. Martin. Examples of excipients can include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl- or propyl-p-hydroxybenzoates or sorbic acid). The preparations optionally can also include flavoring, coloring, and sweetening agents. Alternatively, the composition can be presented as a dry (e.g., lyophilized) product for constitution with water or another suitable vehicle.

For buccal and sublingual administration the composition may take the form of tablets, lozenges, or fast-dissolving films according to conventional protocols.

For administration by inhalation, the compounds for use according to the present invention are conveniently delivered in the form of an aerosol spray from a pressurized pack or nebulizer (e.g., in PBS), with a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can be formulated for parenteral administration (e.g., intravenous or intramuscular) by bolus injection or infusion. Formulations for injection or infusion can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form (e.g., lyophilized) for constitution with a suitable vehicle, e.g., pyrogen-free water.

The pharmaceutical composition can also be formulated for rectal administration as a suppository or retention enema, e.g., containing conventional suppository bases such as cocoa butter or other glycerides.

The FIX protein or conjugate of the invention can be used to treat a subject with a hemostatic disease or condition in combination with at least one other known agent to treat said disease or condition. In one embodiment, the invention relates to a method of treating a subject with a hemostatic disorder comprising administering a therapeutically effective amount of at least one FIX protein or conjugate of the invention, in combination with a source of at least one other clotting factor or agent that promotes hemostasis. Said source in one embodiment is a preparation of plasma, e.g., fresh frozen plasma. Said other clotting factor or agent that promotes hemostasis can be any therapeutic with demonstrated clotting activity. As an example, but not as a limitation, the clotting factor or hemostatic agent can include Factor V, Factor VII, Factor VIII, Factor IX, Factor X, Factor XI, Factor XII, Factor XII, prothrombin, fibrinogen, or activated forms of any of the preceding. The clotting factor of hemostatic agent can also include anti-fibrinolytic drugs, e.g., epsilon-amino-caproic acid, tranexamic acid.

The present invention is further illustrated by the following Examples, which in no way should be construed as further limiting.

EXAMPLES

Example 1

Cloning of Fc-Expressing Constructs

The coding sequence for the constant region of IgG1 (EU # 221-447; the Fc region) was obtained by polymerase chain reaction (PCR) amplification from a leukocyte cDNA library (Clontech, Calif.) using the following oligonucleotide primers:

```
rcFc-F:
                                        (SEQ ID NO: 20)
5'- GCTGCGGTCGACAAAACTCACACATGCCCACCGTGCCCAGCTC-

CGGAACTCCTGGGCGGACCGTCAGTC -3' rcFc-R:
                                        (SEQ ID NO: 21)
5'- ATTGGAATTCTCATTTACCCGGAGACAGGGAGAGGC- 3'
```

The forward primer rcFc-F adds three amino acids (AAV) and a SaiI cloning site before the beginning of the Fc region, and also incorporates a BspEI restriction site at amino acids 231-233 and an RsrII restriction site at amino acids 236-238 using the degeneracy of the genetic code to preserve the correct amino acid sequence (EU numbering). The reverse primer rcFc-R adds an EcoRI cloning site after the stop codon of the Fc. A 25 µl PCR reaction was carried out with 25 pmol of each primer using Expand™ High Fidelity System (Boehringer Mannheim, Indianapolis, Ind.) according to the manufacturer's standard protocol in a MJ Thermocycler using the following cycles: 94° C. 2 minutes; 30 cycles of (94° C. 30 seconds, 58° C. 30 seconds, 72° C. 45 seconds); 72° C. 10 minutes. The expected sized band (~696 bp) was gel purified with a Gel Extraction kit (Qiagen, Valencia, Calif.), and cloned into pGEM T-Easy (Promega, Madison, Wis.) to produce an intermediate plasmid pSYN-Fc-001 (pGEM T-Easy/Fc).

The mouse Igκ signal sequence was added to the Fc CDS using the following primers:

```
re-Igκ sig seq-F:
                                        (SEQ ID NO: 22)
5'- TTTAAGCTTGCCGCCACCATGGAGACAGACACACTCCTGCTA-

TGGGTACTGCTGCTCTGGGTTCCAGGTTCCACTGGTGACAAAACTC-

ACACATGCCCACCG -3'

Fc-noXma-GS-R:
                                        (SEQ ID NO: 23)
5'- GGTCAGCTCATCGCGGGATGGG -3'

Fc-noXma-GS-F:
                                        (SEQ ID NO: 24)
5'- CCCATCCCGCGATGAGCTGACC -3'
```

The rc-Igκ signal sequence-F (rc-Igκ sig seq-F) primer adds a HindIII restriction site to the 5' end of the molecule, followed by a Kozak sequence (GCCGCCACC; SEQ ID NO:25) followed by the signal sequence from the mouse Igκ light chain, directly abutted to the beginning of the Fc sequence (EU# 221). The Fc-noXma-GS-F and Fc-noXma-GS-R primers remove the internal XmaI site from the Fc coding sequence, using the degeneracy of the genetic code to preserve the correct amino acid sequence. Two 25 µl PCR reactions were carried out with 25 pmol of either rc-Igκ signal sequence-F and Fc-noXma-GS-R or Fc-noXma-GS-F and rcFc-R using Expand™ High Fidelity System (Boehringer Mannheim, Indianapolis, Ind.) according to the manufacturer's standard protocol in a MJ Thermocycler. The first reaction was carried out with 500 ng of leukocyte cDNA library (BD Biosciences Clontech, Palo Alto, Calif.) as a template using the following cycles: 94° C. 2 minutes; 30 cycles of (94° C. 30 seconds, 55° C. 30 seconds, 72° C. 45 seconds); 72° C. 10 minutes. The second reaction was carried out with 500 ng of pSYN-Fc-001 (above) as a template using the following cycles: 94° C. 2 minutes; 16 cycles of (94° C. 30 seconds, 58° C. 30 seconds, 72° C. 45 seconds); 72° C. 10 minutes. The expected sized bands (~495 and 299 bp, respectively) were gel purified with a Gel Extraction kit (Qiagen, Valencia, Calif.), then combined in a PCR reaction with 25 pmol of rc-Igκ signal sequence-F and rcFc-R primers and run as before, annealing at 58° C. and continuing for 16 cycles. The expected sized band (~772 bp) was gel purified with a Gel Extraction kit (Qiagen, Valencia, Calif.) and cloned into pGEM T-Easy (Promega, Madison, Wis.) to produce an intermediate plasmid pSYN-Fc-007 (pGEM T-Easy/Igκ sig seq-Fc). The entire Igκ signal sequence-Fc cassette was then subcloned using the HindIII and EcoRI sites into pcDNA3.1 (Invitrogen, Carlsbad, Calif.) mammalian expression vector to generate pSYN-Fc-015 (pcDNA3/Igκ sig seq-Fc).

The nucleic acid sequence for the insert in pSYN-Fc-015 is provided as SEQ ID NO:63, in which the signal sequence (first 60 nucleotides) is shown in italics.

restriction endonuclease sites while preserving the coding sequence. Specifically, the codons for A231, P232, and E233 (EU numbering) were modified from GCA CCT GAA in the nucleotide sequence for the Fc region of IgG1 in Genbank accession no. Y14735 to GCT CCG GAA at nucleotides 93 and 96 in order to incorporate a BspEI restriction site while preserving the amino acid code. Also, the codons for G236, G237, and P238 (EU numbering) were modified from GGG GGA CCG to GGC GGA CCG at nucleotide 108 in order to incorporate a RsrII restriction site while preserving the amino acid code. Additionally, there was a noncoding difference at Leu 234 from CTC to CTG at nucleotide 102, a noncoding difference at R465 from CGG to CGC at nucleotide 465, and a noncoding difference at L640 from CTG to TTG at nucleotide 592.

The amino acid sequence for the translated product encoded by SEQ ID NO:63 is provided as SEQ ID NO:64, where the signal peptide (first 20 residues) is shown in italics.

```
                                                              SEQ ID NO: 64
     METDTLLLWV  LLLWVPGSTG  DKTHTCPPCP  APELLGGPSV  FLEPPKPKDT  LMISRTPEVT    60

CVVVDVSHED  PEVKFNWYVD  GVEVHNAKTK  PREEQYNSTY  RVVSVLTVLH  QDWLNGKEYK   120

CKVSNKALPA  PIEKTISKAK  GQPREPQVYT  LPPSRDELTK  NQVSLTCLVK  GFYPSDIAVE   180

WESNGQPENN  YKTTPPVLDS  DGSFFLYSKL  TVDKSRWQQG  NVFSCSVMHE  ALHNHYTQKS   240

LSLSPGK                                                                 247
```

Example 2

Cloning of FIX-Fc-Expressing Constructs

The following primers were used to generate the various FIX-Fc expression constructs (regions that annealed to the initial template are indicated in bold).

```
SEQ ID NO: 63
atggagacag acacactcct gctatgggta ctgctgctct
gggttccagg ttccactggt gacaaaactc acacatgccc
accgtgccca gctccggaac tgctgggcgg accgtcagtc
ttcctcttcc ccccaaaacc caaggacacc ctcatgatct
cccggacccc tgaggtcaca tgcgtggtgg tggacgtgag
ccacgaagac cctgaggtca agttcaactg gtacgtggac
ggcgtggagg tgcataatgc caagacaaag ccgcgggagg
agcagtacaa cagcacgtac cgtgtggtca gcgtcctcac
cgtcctgcac caggactggc tgaatggcaa ggagtacaag
tgcaaggtct ccaacaaagc cctcccagcc cccatcgaga
aaaccatctc caaagccaaa gggcagcccc gagaaccaca
ggtgtacacc ctgcccccat cccgcgatga gctgaccaag
aaccaggtca gcctgacctg cctggtcaaa ggcttctatc
ccagcgacat cgccgtggag tgggagagca atgggcagcc
ggagaacaac tacaagacca cgcctcccgt gttggactcc
gacggctcct tcttcctcta cagcaagctc accgtggaca
agagcaggtg gcagcagggg aacgtcttct catgctccgt
gatgcatgag gctctgcaca accactacac gcagaagagc
ctctccctgt ctccgggtaa a
```

For secretion of the Fc region, a heterologous signal peptide was used, specifically the mouse Igκ light chain signal sequence, as found in GenBank accession no. AB050084, *Mus musculus* VL2C mRNA for anti-A/dT antibody. In the Fc region, the nucleotide sequence was modified to incorporate

```
NatFIX-F:
                                      (SEQ ID NO: 26)
5'- TTACTGCAGAAGGTTATGCAGCGCGTGAACATG -3'

F9-R-ZTM:
                                      (SEQ ID NO: 27)
5'- AGTGAGCTTTGTTTTTTCCTTAATCC -3'

FIXaddXba-F:
                                      (SEQ ID NO: 28)
5'- CAAGGGAATCTAGAGAGAGAATGTATGGAAGAAAA-
GTG -3'

FIXaddXba-R:
                                      (SEQ ID NO: 29)
5'- ACATTCTCTCTCTAGATTCCCTTGAACAAACTCTTCC -3' pEDF1-F:
                                      (SEQ ID NO: 30)
5'- ATGACATCCACTTTGCCTTTCTCT -3' fcclv-R:
                                      (SEQ ID NO: 31)
5'- ATAGAAGCCTTTGACCAGGC -3'

FIX-Fc delta-F:
                                      (SEQ ID NO: 32)
5'- AAAAACAAAGCTCACTGACAAAACTCACACATG-
CCCACC -3'

FIX-Fc delta-R:
```

-continued

```
                                      (SEQ ID NO: 33)
5'- GTGTGAGTTTTGTCAGTGAGCTTTGTTTTTTCCTT-

AATCCAG -3'

IgkFc-NotI-F:
                                      (SEQ ID NO: 34)
5'- ATGCGGCCGCGCCGCCACCATGGAGACAGACACACTC -3'

Fc-Xho-R:
                                      (SEQ ID NO: 35)
5'- ATCTCGAGTCATTTACCCGGAGACAG -3'

FIXa5:
                                      (SEQ ID NO: 36)
5'-GTCAAAGCTTCGCGACGTACGGCCGCCACCATGCAGCGCGTG-

AACATGATC -3'

FIXa3:
                                      (SEQ ID NO: 37)
5'- CTGTGATGTTCCCACAGTACTTACCAACCTGCGTG -3'

FIXb5:
                                      (SEQ ID NO: 38)
5'- AGTACTGTGGGAACATCACAG -3'

FIXb3:
                                      (SEQ ID NO: 39)
5'- TGACTCTAGATTCCCTTGAACAAACTCTTCCAA -3'
```

Construction of FIX-Fc Expression Plasmids

Construction of the FIX-Fc expression plasmids began with reverse transcriptase-polymerase chain reaction (RT-PCR) of the FIX coding sequence, followed by the generation of a number of different intermediate plasmids used for expression during the early phases of research before the final three plasmids were created: pSYN-FIX-021, pSYN-FIX-027, and pSYN-FIX-030. The final FIX-Fc constructs were all made such that the FIX coding region was directly fused to the Fc coding sequence, with no intervening linker.

The native Factor IX (FIX) sequence (GenBank accession no. NM_000133) was obtained by RT-PCR from human adult liver mRNA using the primers NatFIX-F and F9-R-ZTM with the Invitrogen Superscript RT-PCR with Platinum Taq kit according to the manufacturer's standard protocol. The cycle used was 30 min at 50° C. for the reverse transcription, followed by denaturing at 94° C. for 2 min and 35 cycles of (94° C. 30 sec, 55° C. 30 sec, 72° C. 1 min), followed by 10 min extension at 72° C. and then storage at 4° C. The resulting PCR fragment was subcloned into the vector pGEM-T-Easy to generate pSYN-FIX-001. The entire sequence was then amplified using an extended version of these two primers to add restriction sites (5' BsiWI), Kozak sequence and a linker, and further amplified in three PCR reactions to add the Fc sequence and subcloned to create pSYN-FIX-002, for expressing FIX-Fc N297A in a different vector system (pEE12.4/FIX-Fc N297A). Other sequences outside of the FIX coding sequence were subcloned into pSYN-FIX-002 to create pSYN-FIX-003 (pEE12.4-6.4/FIX-Fc N297A/PACE) and pSYN-FIX-004 (pEE12.4-6.4/FIX-Fc N297A/KEX2), before the FIX sequence was subcloned into a different expression system, pSYN-FIX-011 (pED.dC/FIX-Fc N297A).

The XbaI site was added to the FIX sequence in a manner similar to that in which the XmaI site was removed from Fc, above. Briefly, the internal primers FIXaddXba-F and FIXaddXba-R were used to add the XbaI site while preserving the amino acid sequence. Two 25 µl PCR reactions were carried out with 50 pmol of either pEDFI-F and FIXaddXba-R or FIXaddXba-F and fcc1v-R using Expand™ High Fidelity System according to the manufacturer's standard protocol in a MJ Thermocycler. Both reactions were carried out with 500 ng of pSYN-FIX-011 as a template using the following cycles: 94° C. 2 min; 14 cycles of (94° C. 30 sec, 48° C. 30 sec, 72° C. 2 min); 72° C. 10 min. Bands of the expected sizes (~290 and 1698 bp, respectively) were excised from an agarose gel and DNA purified with a Gel Extraction kit, then combined in a PCR reaction with 50 pmol of pEDFl-F and fcc1v-R primers and run as before, annealing at 48° C. and continuing for 14 cycles. The plasmid pSYN-FIX-011 was used as the template, and the primers pEDfl-F and fcc1v-R external to the PstI (5') and SalI (3') restriction sites were used in the same type of three PCR reactions to generate the identical FIX amino acid sequence while incorporating the XbaI restriction site. The resulting 1965 bp fragment was digested with PstI/SalI, and subcloned back into the same sites in pSYN-FIX-011 to generate pSYN-FIX-013 (pED.dC/FIX-Fc N297A w/XbaI site). The Fc N297A sequence was subsequently cut out and replaced with the wildtype sequence to generate pSYN-FIX-016 (pED.dC/FIX-Fc w/XbaI site).

The sequence for the final FIX-Fc coding region (without any linker) was generated in a similar manner. Briefly, the internal primers FIX-Fc delta-F and FIX-Fc delta-R, which anneal to either the Fc or FIX sequence with a corresponding FIX or Fc overhang, were used to remove the linker region. Two 25 µl PCR reactions were carried out with 10 pmol of either pEDF1-F and FIX-Fc delta-R or FIX-Fc delta-F and rcFc-R using Expand™ High Fidelity Polymerase similar to the manufacturer's standard protocol, substituting in Failsafe™ Buffer E, in 10 µl reactions in the Rapidcycler. Both reactions were carried out with 500 ng of pSYN-FIX-016 (pED.dC/FIX-Fc w/XbaI) as a template using the following cycles: 94° C. 1 min; 14 cycles of (94° C., 0 sec, 52° C., 0 sec, 72° C. 90 sec, slope 6.0); 72° C. 10 min. The expected sized bands (~1496 and 710 bp, respectively) were excised from an agarose gel and DNA purified with the Eppendorf Perfectprep Gel Cleanup Kit®, then combined in a PCR reaction with 10 pmol of pEDF1-F and rcFc-R primers and run as before, annealing at 52° C. and continuing for 14 cycles. The resulting 2200 bp fragment was digested with XbaI/RsrII, and the resulting 1255 bp fragment was subcloned back into the same sites in pSYN-FIX-016 to generate pSYN-FIX-020 (pED.dC/FIX-Δlinker-Fc w/XbaI site).

The FIX-Δlinker-Fc sequence was subsequently cut out and subcloned into the EcoRI/HindIII sites of pcDNA4/myc-His C to generate pSYN-FIX-021 (pcDNA4/FIX-Fc w/XbaI site). Note that although this vector can be used to add the myc and His tags to the protein of interest, this plasmid was constructed in such a way to only produce the untagged FIX-Fc protein.

A nucleotide sequence for FIX-Fc in pSYN-FIX-021, including the prepropeptide, is provided as SEQ ID NO:65.

```
                                        SEQ ID NO: 65
    atgcagcgcg tgaacatgat catggcagaa tcaccaggcc tcatcaccat ctgcctttta ggatatctac tcagtgctga atgtacagtt tttcttgatc atgaaaacgc caacaaaatt ctgaatcggc caaagaggta taattcaggt aaattggaag agtttgttca agggaatcta gagagagaat gtatggaaga aaagtgtagt tttgaagaag cacgagaagt ttttgaaaac actgaaagaa caactgaatt ttggaagcag tatgttgatg gagatcagtg tgagtccaat ccatgtttaa atggcggcag
```

```
ttgcaaggat gacattaatt cctatgaatg ttggtgtccc
tttggatttg aaggaaagaa ctgtgaatta gatgtaacat
gtaacattaa gaatggcaga tgcgagcagt tttgtaaaaa
tagtgctgat aacaaggtgg tttgctcctg tactgaggga
tatcgacttg cagaaaacca gaagtcctgt gaaccagcag
tgccatttcc atgtggaaga gtttctgttt cacaaacttc
taagctcacc cgtgctgaga ctgttttttcc tgatgtggac
tatgtaaatt ctactgaagc tgaaaccatt ttggataaca
tcactcaaag cacccaatca tttaatgact tcactcgggt
tgttggtgga gaagatgcca aaccaggtca attcccttgg
caggttgttt tgaatggtaa agttgatgca ttctgtggag
gctctatcgt taatgaaaaa tggattgtaa ctgctgccca
ctgtgttgaa actggtgtta aaattacagt tgtcgcaggt
gaacataata ttgaggagac agaacataca gagcaaaagc
gaaatgtgat tcgaattatt cctcaccaca actacaatgc
agctattaat aagtacaacc atgacattgc ccttctggaa
ctggacgaac ccttagtgct aaacagctac gttacccta
tttgcattgc tgacaaggaa tacacgaaca tcttcctcaa
atttggatct ggctatgtaa gtggctgggg acatgtcttc
cacaaaggga gatcagcttt agttcttcag taccttagag
ttccacttgt tgaccgagcc acatgtcttc gatctacaaa
gttcaccatc tataacaaca tgttctgtgc tggcttccat
gaaggaggta gagattcatg tcaaggagat agtgggggac
cccatgttac tgaagtggaa gggaccagtt tcttaactgg
aattattagc tggggtgaag agtgtgcaat gaaaggcaaa
tatggaatat ataccaaggt gtcccggtat gtcaactgga
ttaaggaaaa aacaaagctc actgacaaaa ctcacacatg
cccaccgtgc ccagctccgg aactcctggg cggaccgtca
gtcttcctct tccccccaaa acccaaggac accctcatga
tctcccggac ccctgaggtc acatgcgtgg tggtggacgt
gagccacgaa gaccctgagg tcaagttcaa ctggtacgtg
gacggcgtgg aggtgcataa tgccaagaca aagccgcggg
aggagcagta caacagcacg taccgtgtgg tcagcgtcct
caccgtcctg caccaggact ggctgaatgg caaggagtac
aagtgcaagg tctccaacaa agccctccca gcccccatcg
agaaaaccat ctccaaagcc aaagggcagc cccgagaacc
acaggtgtac accctgcccc catcccggga tgagctgacc
aagaaccagg tcagcctgac ctgcctggtc aaaggcttct
atcccagcga catcgccgtg gagtgggaga gcaatgggca
gccggagaac aactacaaga ccacgcctcc cgtgttggac
tccgacggct ccttcttcct ctacagcaag ctcaccgtgg
acaagagcag gtggcagcag gggaacgtct tctcatgctc
cgtgatgcat gaggctctgc acaaccacta cacgcagaag
agcctctccc tgtctccggg taaa
```

The nucleotide sequence in the Factor IX portion was modified from what is present in GenBank to incorporate an XbaI site without changing the amino acid code. Specifically, the coding sequence in the N59, L60, and E61 region was changed from AAC CTT GAG to AAT CTA GAG at nucleotides 177 and 180, which adds an XbaI restriction site. There is also a non-coding change at V447 from GTA to GTG at nucleotide 1341. In the Fc region, the nucleotide sequence was modified to incorporate restriction endonuclease sites while preserving the coding sequence. Specifically, the codons in the region for A472, P473, and E474 (Fc EU numbering 231-233) were modified from GCA CCT GAA in the nucleotide sequence for the Fc region of IgG1 in GenBank accession no. Y14735 to OCT CCG GAA at nucleotides 1416 and 1419 in order to incorporate a BspEI restriction site while preserving the amino acid code. Also, the codons in the region for G477, G478, and P479 (Fc EU numbering 236-238) were modified from GGG QUA CCG to GGC GGA CCG at nucleotide 1431 in order to incorporate a RsrII restriction site while preserving the amino acid code. Finally, there is a noncoding difference at L640 from CTG to TTG.

The FIX-Fc amino acid sequence encoded by SEQ ID NO:65 is provided as SEQ ID NO:66, wherein the signal sequence (28 residues) is shown in italics and the propeptide (18 residues) is shown in bold.

```
                                                     SEQ ID NO: 66
MQRVNMIMAE SPGLITICLL GYLLSAECTV FLDHENANKI LNRPKRYNSG KLEEFVQGNL     60

ERECMEEKCS FEEAREVFEN TERTTEFWKQ YVDGDQCESN PCLNGGSCKD DINSYECWCP    120

FGFEGKNCEL DVTCNIKNGR CEQFCKNSAD NKVVCSCTEG YRLAENQKSC EPAVPFPCGR    180

VSVSQTSKLT RAETVFPDVD YVNSTEAETI LDNITQSTQS FNDFTRVVGG EDAKPGQFPW    240

QVVLNGKVDA FCGGSIVNEK WIVTAAHCVE TGVKITVVAG EHNIEETEHT EQKRNVIRII    300

PHHNYNAAIN KYNHDIALLE LDEPLVLNSY VTPICIADKE YTNIFLKFGS GYVSGWGRVF    360

HKGRSALVLQ YLRVPLVDRA TCLRSTKFTI YNNMFCAGFH EGGRDSCQGD SGGPHVTEVE    420

GTSFLTGIIS WGEECAMKGK YGIYTKVSRY VNWIKEKTKL TDKTHTCPPC PAPELLGGPS    480

VFLFPPKPKD TLMISRTPEV TCVVVDVSHE DPEVKFNWYV DGVEVHNAKT KPREEQYNST    540
```

```
YRVVSVLTVL  HQDWLNGKEY  KCKVSNKALP  APIEKTISKA  KGQPREPQVY  TLPPSRDELT      600

KNQVSLTCLV  KGFYPSDIAV  EWESNGQPEN  NYKTTPPVLD  SDGSFFLYSK  LTVDKSRWQQ      660

GNVFSCSVMH  EALHNHYTQK  SLSLSPGK                                            688
```

Construction of a Single Plasmid for the Coexpression of FIX-Fc and Fc

For construction of the single plasmid for the expression of FIX-Fc and Fc, different restriction sites were added to the mouse Igκ signal peptide-Fc coding sequence using the primers IgκFc-NotI-F and Fc-Xho-R. The template for this PCR reaction was pSYN-Fc-011 (pGEM T-Easy/Igκ signal sequence –Fc without BspEI, RsrII sites). A 10 µl PCR reaction was set up with 100 ng template and 50 pmol of each primer using Expand™ High Fidelity polymerase supplemented with Failsafe™ buffer E in the Rapid Cycler. The PCR reaction was carried out using the following cycles: 94° C. for 1 min; 15 cycles of (94° C. for 0 min, 48° C. for 0 min and 72° C. for 1 min) followed by a final extension of 72° C. for 10 min. The PCR product was run on an agarose gel, and the expected fragment of ~700 bp was excised and DNA purified using a QIAquick gel extraction kit. The PCR product was cloned into pCR2.1-Topo. The mouse Igκ signal peptide-Fc coding sequence was then cloned into pBudCE4.1 using the NotI/XhoI restriction sites.

The nucleotide sequence for the Fc region in pBudCE4.1 (as well as in pSYN-FIX-027 and pSYN-FIX-030, below) is provided as SEQ ID NO:67.

```
                                                  SEQ ID NO: 67
    atggagacag  acacactcct  gctatgggta  ctgctgctct gggttccagg  ttccactggt  gacaaaactc  acacatgccc accgtgccca  gcacctgaac  tcctgggagg  accgtcagtc ttcctcttcc  ccccaaaacc  caaggacacc  ctcatgatct cccggacccc  tgaggtcaca  tgcgtggtgg  tggacgtgag ccacgaagac  cctgaggtca  agttcaactg  gtacgtggac ggcgtggagg  tgcataatgc  caagacaaag  ccgcgggagg agcagtacaa  cagcacgtac  cgtgtggtca  gcgtcctcac cgtcctgcac  caggactggc  tgaatggcaa  ggagtacaag tgcaaggtct  ccaacaaagc  cctcccagcc  cccatcgaga aaaccatctc  caaagccaaa  gggcagcccc  gagaaccaca ggtgtacacc  ctgccccat  cccgcgatga  gctgaccaag aaccaggtca  gcctgacctg  cctggtcaaa  ggcttctatc ccagcgacat  cgccgtggag  tgggagagca  atgggcagcc ggagaacaac  tacaagacca  cgcctcccgt  gttggactcc gacggctcct  tcttcctcta  cagcaagctc  accgtggaca agagcaggtg  gcagcagggg  aacgtcttct  catgctccgt gatgcatgag  gctctgcaca  accactacac  gcagaagagc ctctccctgt  ctccgggtaa  a
```

The same mouse Igκ signal sequence used in pSYN-Fc-015 was utilized for this construct. In the Fc region, the nucleotide sequence was modified to incorporate a restriction endonuclease site while preserving the coding sequence. In the Fc region there are three noncoding differences compared to the sequence or the Fc region of IgG1 in GenBank accession no. Y14735: G236 (EU numbering) was modified from GGG to GGA at nucleotide 108, R465 (EU numbering) was modified from CGG to CGC at nucleotide 465, and a non-coding difference at L640 (EU numbering) was modified from from CTG to TTG at nucleotide 592.

The resulting amino acid sequence is identical to that of pSYN-Fc-015 (SEQ ID NO:64).

FIX-Fc was then cloned into pBudCE4.1 that contained the IgκFc sequence. FIX-Fc was excised from pSYN-FIX-020 (above) using the enzymes HindIII and EcoRI and was cloned into the same sites in pBudCE4.1/IgκFc. The final plasmid containing FIX-Fc downstream of the CMV promoter and IgκFc downstream of the EF1α promoter in pBudCE4.1 was named pSYN-FIX-027.

Construction of a Single Plasmid for the Coexpression of FIX-Fc (with a Truncated FIX Intron I) and Fc An additional FIX-Fc-expression construct was generated which included a truncated form of the FIX intron I (GenBank accession no. NC_000023), which had previously been shown to increase the level of FIX expression due to functional splicing sequences present in the precursor mRNA. Kurachi S et al. (1995) *J Biol Chem.* 270:5276-81. The truncated portion of the FIX intron I was obtained by PCR initially in two pieces that were then assembled together in a third PCR reaction as follows. Two 50 µl PCR reactions were carried out with 45 and 90 pmol of either the primers FIXa5 and FIXa3 or FIXb5 and FIXb3 using Expand™ High Fidelity Polymerase according to the manufacturer's standard protocol in the MJ Thermocycler. Both reactions were carried out with human genomic DNA as a template using the following cycles: 94° C. 3 min; 16 cycles of (94° C. 30 sec, 58° C. 30 sec, 72° C. 90 sec); 72° C. 13.5 min. The 141 and 157 bp sequences of the 5' and 3' end region, respectively, of FIX intron I were obtained and joined by PCR in a second set of PCR reactions that were carried out as before, using a mixture of these products as the new templates and the primers FIXa5 and FIXb3. This fragment was initially cloned into the intermediate vector pCR2.1 TOPO to generate pSYN-FIX-028 (pcR2.1/FIX mini intron1). The HindIII/XbaI fragment containing the FIX mini intron within the context of the FIX CDS ("minigene") was then subcloned into pSYN-FIX-027 to generate pSYN-FIX-030 (pBUD/FIX-Fc mini intron 1/Fc).

A nucleotide sequence for FIX-Fc in pSYN-FIX-030, including the intron, is provided as SEQ ID NO:68. This nucleotide sequence matches that of the pSYN-FIX-021 construct (see SEQ ID NO:65), apart from the insertion in pSYN-FIX-030 of the 299 bp truncated intron approximately between the signal peptide coding sequence and the propeptide coding sequence.

```
                                                  SEQ ID NO: 68
    atgcagcgcg  tgaacatgat  catggcagaa  tcaccaggcc tcatcaccat  ctgccttta  ggatatctac  tcagtgctga
```

```
atgtacaggt ttgtttcctt ttttaaaata cattgagtat
gcttgccttt tagatataga aatatctgat gctgtcttct
tcactaaatt ttgattacat gatttgacag caatattgaa
gagtctaaca gccagcacgc aggttggtaa gtactgtggg
aacatcacag attttggctc catgccctaa agagaaattg
gctttcagat tatttggatt aaaaacaaag actttcttaa
gagatgtaaa attttcatga tgttttcttt tttgctaaaa
ctaaagaatt attcttttac atttcagttt ttcttgatca
tgaaaacgcc aacaaaattc tgaatcggcc aaagaggtat
aattcaggta aattggaaga gtttgttcaa gggaatctag
agagagaatg tatggaagaa aagtgtagtt ttgaagaagc
acgagaagtt tttgaaaaca ctgaaagaac aactgaattt
tggaagcagt atgttgatgg agatcagtgt gagtccaatc
catgtttaaa tggcggcagt tgcaaggatg acattaattc
ctatgaatgt tggtgtccct ttggatttga aggaaagaac
tgtgaattag atgtaacatg taacattaag aatggcagat
gcgagcagtt ttgtaaaaat agtgctgata acaaggtggt
ttgctcctgt actgagggat atcgacttgc agaaaaccag
aagtcctgtg aaccagcagt gccatttcca tgtggaagag
tttctgtttc acaaacttct aagctcaccc gtgctgagac
tgttttttcct gatgtggact atgtaaattc tactgaagct
gaaaccattt tggataacat cactcaaagc acccaatcat
ttaatgactt cactcgggtt gttggtggag aagatgccaa
accaggtcaa ttcccttggc aggttgtttt gaatggtaaa
gttgatgcat tctgtggagg ctctatcgtt aatgaaaaat
ggattgtaac tgctgcccac tgtgttgaaa ctggtgttaa
aattacagtt gtcgcaggtg aacataatat tgaggagaca
gaacatacag agcaaaagcg aaatgtgatt cgaattattc
ctcaccacaa ctacaatgca gctattaata agtacaacca
tgacattgcc cttctggaac tggacgaacc cttagtgcta
aacagctacg ttacacctat ttgcattgct gacaaggaat
acacgaacat cttcctcaaa tttggatctg gctatgtaag
tggctgggga agagtcttcc acaaagggag atcagcttta
gttcttcagt accttagagt tccacttgtt gaccgagcca
catgtcttcg atctacaaag ttcaccatct ataacaacat
gttctgtgct ggcttccatg aaggaggtag agattcatgt
caaggagata gtgggggacc ccatgttact gaagtggaag
ggaccagttt cttaactgga attattagct ggggtgaaga
gtgtgcaatg aaaggcaaat atggaatata taccaaggtg
tcccggtatg tcaactggat taaggaaaaa acaaagctca
ctgacaaaac tcacacatgc ccaccgtgcc cagctccgga actcctgggc ggaccgtcag tcttcctctt ccccccaaaa
cccaaggaca ccctcatgat ctcccggacc cctgaggtca
catgcgtggt ggtggacgtg agccacgaag accctgaggt
caagttcaac tggtacgtgg acggcgtgga ggtgcataat
gccaagacaa agccgcggga ggagcagtac aacagcacgt
accgtgtggt cagcgtcctc accgtcctgc accaggactg
gctgaatggc aaggagtaca gtgcaaggt ctccaacaaa
gccctcccag cccccatcga gaaaaccatc tccaaagcca
aagggcagcc ccgagaacca caggtgtaca ccctgccccc
atcccgggat gagctgacca agaaccaggt cagcctgacc
tgcctggtca aaggcttcta tcccagcgac atcgccgtgg
agtgggagag caatgggcag ccggagaaca actacaagac
cacgcctccc gtgttggact ccgacggctc cttcttcctc
tacagcaagc tcaccgtgga caagagcagg tggcagcagg
ggaacgtctt ctcatgctcc gtgatgcatg aggctctgca
caaccactac acgcagaaga gcctctccct gtctccgggt
aaa
```

The resulting FIX-Fc amino acid sequence is identical to that of pSYN-FIX-021 and pSYN-FIX-027.

Example 3

Cloning of PC5

The coding sequence for human PC5 was obtained by RT-PCR. The following primers were used (areas that anneal to the cDNA are indicated in bold):

```
PC5-KpnI-F:
                                    (SEQ ID NO: 40)
5'- ATCTACACCATCTCCATCAGCAGC -3'

PC5 NotI-R:
                                    (SEQ ID NO: 41)
5'- AAGGCGGCCGCTCAGCCTTGAAATGTACATGTTTTGC -3'

PC5-UTR-F:
                                    (SEQ ID NO: 42)
5'- AGCGAGGGAGCAGCGAGG -3'

PC5-HindIII-R:
                                    (SEQ ID NO: 43)
5'- GGTAGTTGACATGGCGGTTGG -3'

PC5-Afl2-F:
                                    (SEQ ID NO: 44)
5'- CAGCGACTTAAGCCACCATGGGCTGGGGAGCCG -3'

PC5-KpnI-R:
                                    (SEQ ID NO: 45)
5'- GTAGGTTGTGGCCAGCGTGG -3'
```

Coding sequence for human PC5 (GenBank accession no. NM_006200) was obtained in two pieces. The 3' ~1750 bp were obtained using the primers PC5-KpnI-F and PC5-NotI-R with the Invitrogen Superscript RT-PCR with Platinum Taq kit according to the manufacturer's standard protocol, from human liver mRNA. The cycle used for the reverse transcription was 30 min at 50° C. followed by denaturing at 94° C. for 2 min and 35 cycles of 94° C. for 15 sec, 54° C. for 30 sec, 72° C. for 3 min, followed by 10 min extension at 72° C. and then storage at 4° C. This produced a fragment from the internal KpnI site in the PC5 coding sequence through the stop codon, with a NotI site added at the 3 end. This fragment was then cloned into pCR2.1 TOPO according to manufacturer's protocol to generate pSYN-PC5-001 (pCR2.1/PC5 (KpnI-NotI)). This fragment was then subcloned into pcDNA3.1/hygro using the KpnI and NotI restriction sites to generate pSYN-PC5-002 (pcDNA3.1/hygro/PC5 (KpnI-NotI)).

The 5' ~1100 bp of PC5 was obtained in two steps. It was first amplified by RT-PCR using the primers PC5-UTR-F and PC5-HindIII-R to amplify a ~1520 bp fragment from human liver mRNA, using similar conditions as above, with an annealing temperature of 57° C. These primers have complete homology to the native PC5 sequence, in the untranslated 5' sequence and sequence 3' from the internal unique HindIII site, respectively. Note that this HindIII site is not present in the final construct due to a silent nucleotide substitution. This DNA fragment was then gel purified and used as a template for a second PCR reaction with PC5-Afl2-F, which adds an AflII cloning site followed by a Kozak sequence to the N-terminal coding sequence at the 5' end, and PC5-KpnI-R, which anneals 3' to the internal unique KpnI site, to generate an ~1100 bp fragment. The reaction was carried out with the Expand™ High Fidelity System according to the manufacturer's standard protocol in a MJ Thermocycler using the following cycles: 94° C. 2 min; 14 cycles of (94° C. 30 sec, 57° C. 30 sec, 72° C. 2 min), followed by 72° C. 10 min. This fragment was then subcloned into pSYN-PC5-002 using the AflII and KpnI restriction sites to generate pSYN-PC5-003 (pcDNA3.1/hygro/PC5).

The nucleotide sequence encoding PC5 in pSYN-PC5-003 has the following sequence (SEQ ID NO: 61):

```
                                          SEQ ID NO: 61
     atgggctggg ggagccgctg ctgctgcccg ggacgtttgg acctgctgtg cgtgctggcg ctgctcgggg gctgcctgct ccccgtgtgt cggacgcgcg tctacaccaa ccactgggca gtcaaaatcg ccgggggctt cccggaggcc aaccgtatcg ccagcaagta cggattcatc aacataggac agatagggc cctgaaggac tactaccact tctaccatag caggacgatt aaaaggtcag ttatctcgag cagagggacc cacagtttca tttcaatgga accaaaggtg gaatggatcc aacagcaagt ggtaaaaaag cggacaaaga gggattatga cttcagtcgt gcccagtcta cctatttcaa tgatcccaag tggcccagta tgtggtatat gcactgcagt gacaatacac atccctgcca gtctgacatg aatatcgaag gagcctggaa gagaggctac acgggaaaga acattgtggt cactatcctg gatgacgaa ttgagagaac ccatccagat ctgatgcaaa actacgatgc tctggcaagt tgcgacgtga atggaatga cttggaccca atgcctcgtt atgatgcaag caacgagaac aagcatggga ctcgctgtgc tggagaagtg gcagccgctg caaacaattc gcactgcaca gtcggaattg cttcaacgc caagatcgga
```
ggagtgcgaa tgctggacgg agatgtcacg gacatggttg aagcaaaatc agttagcttc aaccccagc acgtgcacat ttacagcgcc agctggggcc cggatgatga tggcaagact gtggacggac cagcccccct cacccggcaa gcctttgaaa acggcgttag aatgggggcgg agaggcctcg gctctgtgtt tgtttgggca tctggaaatg gtggaaggag caaagaccac tgctcctgtg atggctacac caacagcatc tacaccatct ccatcagcag cactgcagaa agcggaaaga aaccttggta cctggaagag tgttcatcca cgctggccac aacctacagc agcggggagt cctacgataa gaaaatcatc actacagatc tgaggcagcg ttgcacggac aaccacactg ggacgtcagc ctcagccccc atggctgcag gcatcattgc gctggccctg gaagccaatc cgtttctgac ctggagagac gtacagcatg ttattgtcag gacttcccgt gcgggacatt tgaacgctaa tgactggaaa accaatgctg ctggttttaa ggtgagccat ctttatggat ttggactgat ggacgcagaa gccatggtga tggaggcaga gaagtggacc accgttcccc ggcagcacgt gtgtgtggag agcacagacc gacaaatcaa gacaatccgc cctaacagtg cagtgcgctc catctacaaa gcctcaggct gctcagataa ccccaaccgc catgtcaact acctggagca cgtcgttgtg cgcatcacca tcacccaccc caggagagga gacctggcca tctacctgac ctcgccctct ggaactaggt ctcagctttt ggccaacagg ctatttgatc actccatgga aggattcaaa aactgggagt tcatgaccat tcattgctgg ggagaaagag ctgctggtga ctgggtcctt gaagtttatg atactccctc tcagctaagg aactttaaga ctccaggtaa attgaaagaa tggtctttgg tcctctacgg cacctccgtg cagccatatt caccaaccaa tgaatttccg aaagtggaac ggttccgcta tagccgagtt gaagacccca cagacgacta tggcacagag gattatgcag gtccctgcga ccctgagtgc agtgaggttg gctgtgacgg gccaggacca gaccactgca atgactgttt gcactactac tacaagctga aaacaatac caggatctgt gtctccagct gcccccctgg ccactaccac gccgacaaga agcgctgcag gaagtgtgcc cccaactgtg agtcctgctt tgggagccat ggtgaccaat gcatgtcctg caaatatgga tactttctga atgaagaaac caacagctgt gttactcact gccctgatgg gtcatatcag gataccaaga aaaatctttg ccggaaatgc agtgaaaact gcaagacatg tactgaattc cataactgta cagaatgtag ggatgggtta agcctgcagg gatcccggtg ctctgtctcc tgtgaagatg -continued
```
gacggtattt caacggccag gactgccagc cctgccaccg cttctgcgcc acttgtgctg gggcaggagc tgatgggtgc attaactgca cagagggcta cttcatggag gatgggagat gcgtgcagag ctgtagtatc agctattact ttgaccactc ttcagagaat ggatacaaat cctgcaaaaa atgtgatatc agttgtttga cgtgcaatgg cccaggattc aagaactgta caagctgccc tagtgggtat ctcttagact taggaatgtg tcaaatggga gccatttgca aggatgcaac ggaagagtcc tgggcggaag gaggcttctg tatgcttgtg aaaaagaaca atctgtgcca acggaaggtt cttcaacaac tttgctgcaa aacatgtaca tttcaaggc
```

SEQ ID NO:61 contains substitutions from the GenBank sequence that do not affect the amino acid coding sequence. Specifically, the nucleotide at position 399 (corresponding to position 876 of GenBank accession no. NM_006200) is a T instead of a C, but preserves the amino acid Ser 133 (corresponding to amino acid numbering in GenBank accession no. NP_006191); nucleotide position 1473 (GenBank position 1950) is a C instead of a T, but preserves the amino acid Ala 491; and nucleotide position 1485 (GenBank position 1962) is an A instead of a G, but preserves the amino acid Ser 496. Note that the nucleotide change at position 1473 eliminates a HindIII restriction site.

Example 4

Cloning of PACE-SOL

The coding sequence for human PACE was obtained by RT-PCR. The following primers were used (areas that anneal to the cDNA are indicated in bold):

```
PACE-F1:
                                       (SEQ ID NO: 46)
5'- GGTAAGCTTGCCATGGAGCTGAGGCCCTGGTTGC -3'

PACE-R1:
                                       (SEQ ID NO: 47)
5'- GTTTTCAATCTCTAGGACCCACTCGCC -3'

PACE-F2:
                                       (SEQ ID NO: 48)
5'- GCCAGGCCACATGACTACTCCGC -3'

PACE-R2:
                                       (SEQ ID NO: 49)
5'- GGTGAATTCTCACTCAGGCAGGTGTGAGGGCAGC -3'
```

The primer PACE-F1 adds a HindIII site to the 5' end of the PACE sequence beginning with 3 nucleotides before the start codon, while the primer PACE-R2 adds a stop codon after amino acid 715, which occurs at the end of the extracellular domain of PACE, as well as adding an EcoRI site to the 3' end of the stop codon. The PACE-R1 and PACE-F2 primers anneal on the 3' and 5' sides of an internal BamHI site, respectively. Two RT-PCR reactions were then set up using 25 pmol each of the primer pairs of PACE-F1/R1 or PACE-F2/R2 with 20 ng of adult human liver RNA (Clontech; Palo Alto, Calif.) in a 50 µl RT-PCR reaction using the SuperScript™ One-Step RT-PCR with PLATINUM® Taq system (Invitrogen, Carlsbad, Calif.) according to manufacturer's protocol. The reaction was carried out in a MJ Thermocycler using the following cycles: 50° C. 30 minutes; 94° C. 2 minutes; 30 cycles of (94° C. 30 seconds, 58° C. 30 seconds, 72° C. 2 minutes), followed by 72° C. 10 minutes. These fragments were each ligated into the vector pGEM T-Easy (Promega, Madison, Wis.) and sequenced fully. The F2-R2 fragment was then subcloned into pcDNA6 V5/His (Invitrogen, Carlsbad, Calif.) using the BamHI/EcoRI sites, and then the F1-R1 fragment was cloned into this construct using the HindIII/BamHI sites. The final plasmid, pcDNA6-PACE, produces a soluble form of PACE (amino acids 1-715), as the transmembrane region has been deleted. The sequence of PACE in pcDNA6-PACE is essentially as described in Harrison S et al. (1998) *Semin Hematol* 35(2 Suppl 2):4-10.

Example 5

Cloning of Kex2-SOL

Coding sequence for the yeast endoprotease, KEX2, was obtained by RT-PCR from *Saccharomyces cerevisiae* polyA+ mRNA (BD Clontech, cat # 6999-1) using the following primers (areas that anneal to the cDNA are indicated in bold):

```
KEX2-F:
                                       (SEQ ID NO: 50)
5'- GCGCTAGCCGTACGGCCGCCACCATGAAAGTGAGGAAATA-

TATTACTTTATGC -3'

KEX2-BglII-F:
                                       (SEQ ID NO: 51)
5'- GCTATTGATCACAAAGATCTACATCCTCC -3'

KEX2-BglII-R:
                                       (SEQ ID NO: 52)
5'- GGAGGATGTAGATCTTTGTGATCAATAGC -3'

KEX2-675-R:
                                       (SEQ ID NO: 53)
5'- GCGAATTCCGGTCCGTCATTGCCTAGGGCTCGAGAG-

TTTTTTAGGAGTGTTTGGATCAG -3'
```

These primers were used to obtain coding sequence for KEX2 (amino acids 1-675), the yeast homolog to PACE, in two pieces in a manner similar to that used for PACE-SOL, Example 4 above; similarly, the transmembrane region was removed to generate the soluble form of the protein.

Example 6

Cloning of PC7-SOL

Coding sequence for PC7 was obtained by RT-PCR from human adult liver mRNA using the following primers (areas that anneal to the cDNA are indicated in bold):

```
PC7-BamMut-F:
                                       (SEQ ID NO: 54)
5'- GCATGGACTCCGATCCCAACG -3'

PC7-BamMut-R:
                                       (SEQ ID NO: 55)
5'- CGTTGGGATCGGAGTCCATGC -3'

PC7-F:
                                       (SEQ ID NO: 56)
5'- GGTAAGCTTGCCGCCACCATGCCGAAGGGGAGGCAGAAAG -3'

PC7-SOL-R:
                                       (SEQ ID NO: 57)
5'- TTTGAATTCTCAGTTGGGGGTGATGGTGTAACC -3'
```

-continued

PC7-Xma-F:
(SEQ ID NO: 58)
5'- GGCACCTGAATAACCGACGG -3'

PC7-Xma-R:
(SEQ ID NO: 59)
5'- CGTCACGTTGATGTCCCTGC -3'

These primers were used to obtain coding sequence for PC7 (amino acids 1-663) in three pieces in a manner similar to that used for PACE-SOL, Example 4 above; similarly, the transmembrane region was removed to generate the soluble form of the protein.

Example 7

Generation of Propeptide Antibody

A peptide with the sequence TVFLDHENANKILNRP-KRC (SYN1117; SEQ ID NO:60) corresponding to the 18 amino acid propeptide sequence of FIX, with a Cys residue added at the C terminus for conjugation to Keyhole Limpet Hemocyanin (KLH) was synthesized. This peptide was conjugated to KLH, two New Zealand white rabbits were immunized, and antisera collected.

Peptide SYN 1117 was conjugated to Ultralink® Iodoacetyl Gel (Pierce, Rockford, Ill.) according to manufacturer's protocol. The gel-linked peptide was subsequently packed into a column and the antibody was then affinity purified over the immobilized propeptide column by gravity flow. 10 ml of antisera was filtered through a 0.2 μm sterile syringe filter to remove particulate matter. The antiserum was then applied to the column in 1.5 ml fractions, each of which was allowed to bind the resin for 1 hour. The column was washed with PBS, and the purified antibody eluted in 100 mM glycine, pH 2.8, then neutralized with 1 M Tris, pH 9.0. Antibody-containing fractions (as determined by A280) were pooled and dialyzed into PBS and 0.2% sodium azide was added for storage.

Example 8

Transfection of Lines

HEK 293 Transfections

HEK 293H cells were adapted to adherent culture using serum-containing medium. Suspension cells were transferred to a T75 flask containing Dulbecco's modified Eagle medium (DMEM) (high glucose) supplemented with 10% fetal bovine serum (FBS) and 0.1 mM non-essential amino acids and grown as stationary cultures at 37° C./5% $CO_2$. Adherent HEK 293H cells were subcultured every three to four days. Subculturing was performed by dislodging cells from the bottom of the flask by gently pipetting the medium up and down.

10-$cm^2$ Dishes

10-$cm^2$ dishes were seeded with 2.5×10⁶ cells in 10 ml adherent growth medium one day prior to transfection. Transfections were carried out using calcium phosphate Profection transfection reagent (Promega, Madison, Wis.). Three hours before transfection, medium was replaced with 10 ml fresh growth medium. For each transfection 500 μl of 2×HEPES buffered saline (2×HBS) was added to a sterile tube. In a second sterile tube, 20 μg of DNA (either 9 μg FIX-021/9 μg Fc-015/2 μg PC5-003, or 9 μg FIX-027/9 μg Fc-015/2 μg PC5-003, or 9 μg FIX-030/9 μg Fc-015/2 μg PC5-003) was mixed with 62 μl of 2M $CaCl_2$ and the total volume increased to 500 μl with sterile water. The DNA/$CaCl_2$ mix was added dropwise to the 2×HBS while vortexing. The DNA mixture was incubated for 30 minutes at room temperature and then vortexed again briefly before adding dropwise to the cells. Cells were incubated with the DNA mixture for 16 hours at 37° C./5% $CO_2$ before removing the transfection solution, washing the cells with Hanks balanced salt solution (HBSS) and then adding 10 ml fresh growth medium to the cells.

48 to 72 hours after transfection, cells were removed from 10-$cm^2$ dishes by pipetting up and down and were each split into 10-$cm^2$ dishes in 5 ml fresh growth medium or split into 96-well plates with 100 μl growth medium per well. 24 hours after plating, selection was initiated by adding an equal volume of growth medium containing the appropriate antibiotic to give the final concentrations of hygromycin at 200 μg/ml or Zeocin, Geneticin, and Hygromycin at 25, 75, and 25 μg/ml. Once colonies of antibiotic-resistant cells began to form, cells were isolated from 10-$cm^2$ dishes with cloning rings or expanded from 96-well plates to 24-well plates, then to T25 flasks and T75 flasks before adapting the cell lines back to serum-free suspension culture. As cells were transferred from 96-well plates and 10-$cm^2$ dishes to 24-well plates, the antibiotic concentration was decreased by one half and cells were then maintained in this reduced antibiotic medium.

6-Well Dishes 6-well dishes were seeded with 5×10⁵ cells in 2 ml adherent growth medium one day prior to transfection. Transfections were carried out using calcium phosphate Profection transfection reagent (Promega, Madison, Wis.). Three hours before transfection, medium was replaced with 2 ml fresh growth medium. For each transfection 83 μl of 2×HBS was added to a sterile tube. In a second sterile tube, 4 μg of DNA (3.6 μg FIX-027/0.4 μg PC5-003) was mixed with 10 μl of 2M $CaCl_2$ and the total volume increased to 83 μl with sterile water. The DNA/$CaCl_2$ mix was added dropwise to the 2×HBS while vortexing. The DNA mixture was incubated for 30 minutes at room temperature and then vortexed again briefly before adding dropwise to the cells. Cells were incubated with the DNA mixture for 16 hours at 37° C./5% $CO_2$ before removing the transfection solution, washing the cells with HBSS and then adding 2 ml fresh growth medium to the cells.

40 to 72 hours after transfection, cells were removed from 6-well plates by pipetting up and down and transferring cells to T75 flasks. 24 hours after plating, selection was initiated by adding an equal volume of growth medium containing hygromycin at a final concentration of 200 μg/ml. Once a pool of stably selected cells was generated, cells were counted and diluted to 1 cell/well in 96-well plates. As clonal cell lines became confluent, cells were expanded from 96-well plates to 24-well plates, T25 and T75 flasks and were then adapted back to serum-free suspension culture as described above.

All other HEK transfections were carried out in a similar manner, substituting in Kex2-SOL or PC7-SOL expressing plasmids for PC5. For these transfections, Lipofectamine™ 2000 (Invitrogen, Carlsbad, Calif.) transfection reagent was used according to manufacturer's protocol instead of calcium phosphate.

CHO transfections were carried out in a similar manner, utilizing similar FIX-Fc expressing plasmids with the same processing enzyme expression plasmids. In some cases, SuperFect (Qiagen, Valencia, Calif.) transfection reagent was used according to manufacturer's protocol in place of calcium phosphate.

Example 9

Analysis of Transient and Stable Cell Lines

Western Blotting

For analysis of all transient transfections, CHO stable transfections of FIX-Fc with PC5, and HEK 293 stable transfections of FIX-Fc with PC7, conditioned media from the cells was subject to protein A immunoprecipitation. Briefly, cell culture supernatant was mixed with approximately 40 μl of protein A-Sepharose 50% slurry and incubated at 4° C. with rocking for 1 hour, then centrifuged to pellet the protein A beads. Beads were resuspended in 1 ml of PBS or similar buffer, spun down, and buffer aspirated, and the process repeated 1-2 times. The beads were then resuspended with either reduced or non-reduced sodium dodecylsulfate-polyacrylamide gel electrophoresis (SDS-PAGE) loading dye, heated from 30 sec to 5 min, spun down, and the eluted protein in the dye was loaded on SDS-PAGE gels and run according to standard protocols. Gels were transferred to nitrocellulose membranes and Western blots performed as described below.

For analysis of all other stable transfections, protein was first purified before being analyzed in Western blots. CHO produced FIX-Fc that was transfected alone, with PACE, or PC7 was purified over protein A, eluted, run on SDS-PAGE, transferred to nitrocellulose, and Western blots performed. HEK produced FIX-Fc with PC5 was subjected to three-column purification (see below) and analyzed in a similar manner.

Fc Western Blot

The antibody used for Fc Western blotting experiments was a goat anti-human IgG (Fc specific)-horseradish peroxidase conjugate (Pierce ImmunoPure® antibody, catalog # 31416). This antibody was diluted 1:10,000 in PBS-T (PBS with 0.1% Tween-20) and incubated with the membrane for 1 hour at room temperature with gentle rocking. After three 10 minute washes in PBS-T of approximately 20 ml each, chemiluminescent detection was performed.

FIX Western Blot

For FIX Western blotting experiments, a goat anti-human FIX-horseradish peroxidase conjugate (Enzyme Research Laboratories, catalog #FIX-EIA-130D) was used. The antibody was diluted 1:1000 in PBS-T and incubated with the membrane for 1 hour at room temperature with gentle rocking. After three 10 minute washes of approximately 20 ml each, the membrane was ready for chemiluminescent detection.

FIX Propeptide Western Blot

For the propeptide Western blot, rabbit anti-FIX propeptide antibody (see Example 7) was diluted 1:10,000 in PBS-T and incubated with the membrane for 1 hour at room temperature with gentle rocking. The membrane was subsequently placed into three 10-minute washes of approximately 20 ml each. The secondary (detection) antibody was a goat anti-rabbit IgG-horseradish peroxidase conjugate (Southern Biotechnology Associates, catalog #4010-05) diluted 1:20,000 in PBS-T. The secondary antibody was incubated with the membrane for 30 minutes to 1 hr at room temperature, and then washed three times in approximately 20 ml of PBS-T buffer for 15 minutes each in preparation for chemiluminescent detection.

Chemiluminescent Detection

Detection of all immunoblots was performed using the ECL Plus Western Blotting Detection System (Amersham Biosciences catalog #RPN2132) according to the manufacturer's instructions. Visualization of the signal was performed on a Storm 840 Phosphorimager (Molecular Devices).

Example 10

Summary of Propeptide Processing Experiments

Western Blotting

Transient transfections in CHO cells initially indicated that while FIX-Fc transfected alone retained the propeptide, cotransfection of FIX-Fc with either PC5, PACE-SOL, PC7-SOL, or KEX2-SOL was sufficient to completely remove the propeptide. As shown in FIG. 4, FIX (top panels) and FIX propeptide (bottom panels) Western blots of transient transfections in CHO cells initially indicated that FIX-Fc transfected alone retained the propeptide (bands present on both FIX and propeptide Western blots, lanes 1 and 5). In contrast, Western blots of transient transfections in CHO cells initially indicated that cotransfection of FIX-Fc with PC5 (lane 4), PACE-SOL (lanes 2 and 6), PC7-SOL (lanes 3 and 7), or KEX2-SOL (lane 8) was sufficient to completely remove the propeptide (bands present in FIX but not propeptide Western blots). Note, however, that cotransfection with KEX2-SOL (lane 8) resulted in an additional, smaller FIX-containing band (top panel), likely due to cryptic cleavage by this more promiscuous enzyme (Rockwell et al. (2002) *Chem. Rev.* 102: 4525-48) at an additional site in FIX.

FIG. 5 demonstrates that in stably transfected CHO cell lines, PACE-SOL is capable of fully processing the propeptide, while PC7-SOL is not. Comparison was made between Protein A-purified material from a CHO cell line stably expressing FIX-Fc dimer, monomer, and Fc, cotransfected with either PACE-SOL or PC7-SOL. Beginning with the cotransfection with PACE-SOL, lane 1 of the SDS-PAGE gel in panel A identifies all three species, lane 1 of the FIX Western in panel B confirms that the dimer and monomer bands contain FIX, and lane 1 of the propeptide Western in panel C demonstrates (by the absence of bands) that the propeptide is fully processed by PACE. In contrast, with respect to cotransfection with PC7-SOL lane 2 of the SDS-PAGE gel in panel A again identifies all three species, lane 2 of the FIX Western in panel B again confirms that the dimer and monomer bands contain FIX, but lane 2 of the propeptide Western in panel C demonstrates (by presence of bands) that the propeptide is still present in the FIX-Fc dimer and monomer cotransfected with PC7-SOL.

FIG. 6 demonstrates that in stably transfected CHO cell lines, PC5 is capable of fully processing the propeptide. In FIG. 6, lanes 1, 2, and 3 show FIX Western (top panel) and propeptide Western (lower panel) results for protein A pull-downs from cell lines stably expressing FIX-Fc dimer, monomer, and Fc cotransfected with PC5. Lanes 1, 2 and 3 correspond to stable cell lines amplified with 25, 50, and 100 nM methotrexate, respectively. In the FIX Western, FIX-Fc dimer and monomer bands are indicated, and the Fc band does not react. The propeptide Western confirmed that the dimer and monomer bands do not contain propeptide (no significant bands found). In FIG. 6, lanes 4 and 5 show FIX Western (top panel) and propeptide Western (lower panel) results for protein A pulldowns from controls, CHO cell lines transfected with either FIX-Fc alone (lane 4) or FIX-Fc together with PACE-SOL (lane 5). As shown in lane 5, FIX-Fc purified from CHO cell lines transfected with PACE-SOL (lane 5) is fully processed (note presence of strong bands in FIX Western, top panel, but only faint background bands in the propeptide Western, bottom panel). In contrast, lane 4 shows that the propeptide is still present in FIX-Fc purified from CHO cell lines without any cotransfected processing enzyme (note presence of strong bands in both FIX and propeptide Westerns, top and bottom panels, respectively).

In summary, examination of stably transfected CHO cell lines demonstrated that only PACE-SOL (FIG. 5) and PC5 (FIG. 6) were able to completely process the propeptide, while FIX-Fc transfected alone (FIG. 6) or with PC7-SOL (FIG. 5) produced proFIX-Fc.

The ability of these various enzymes to remove the propeptide was also examined in HEK 293 cells. FIG. 7 shows that PC5, but not PC7-SOL, completely removed the propeptide from FIX-Fc derived from transiently transfected HEK 293 cells. For the results shown in FIG. 7, HEK 293-H cells were transiently transfected with FIX-Fc and Fc alone; FIX-Fc, Fc and PC5; or FIX-Fc, Fc, and PC7-SOL. The resulting conditioned media was subject to protein A pulldowns, reducing SDS-PAGE, and Fc Western blotting (left panel) or propeptide Western blotting (right panel). As shown in FIG. 7, FIX-Fc protein derived from transfections without any processing enzyme retained the propeptide (lanes 3, "−"), as did FIX-Fc cotransfected with PC7-SOL (lanes 8-11, from transfections performed in quadruplicate), as can be seen from bands present in both Fc and propeptide Westerns. In contrast, PC5 completely removed the propeptide (lanes 4-7 from transfections performed in quadruplicate), as indicated by bands present only in the Fc, but not the propeptide, Western blots. As controls for these Westerns, FIX-Fc dimer purified from CHO cells transfected alone (lanes 1) or with PACE-SOL (lanes 2) were analyzed. Propeptide was present in FIX-Fc transfected without any processing enzyme (bands in lanes 1 of both Westerns) but absent in FIX-Fc contransfected with PACE-SOL (lanes 2, band present in Fc Western, but only faint background band in Propeptide Western).

FIG. 8 shows that KEX2-SOL was unable to process pro-FIX-Fc derived from HEK 293 cells transiently transfected with FIX-Fc. Conditioned media from HEK 293 cells transiently transfected with FIX-Fc, Fc, and KEX2-SOL was subject to protein A pulldowns and either non-reducing SDS-PAGE and Fc Western blotting (top panel) or reducing SDS-PAGE and propeptide Western blotting (bottom panel). As shown in FIG. 8, FIX-Fc cotransfected with KEX2-SOL is not processed, as can be seen by the presence of propeptide in this material (lanes 3 and 4, bands present on both blots). Lane 3 material has wildtype Fc in all three species (dimer, monomer, and Fc alone), while lane 4 material has N297A Fc. As controls, FIX-Fc dimer purified from CHO cells transfected alone (lane 1) or with PACE-SOL (lane 2) were analyzed, confirming that the propeptide was present in FIX-Fc transfected without any processing enzyme (bands in both Westerns, lane 1) but absent in FIX-Fc contransfected with PACE-SOL (lane 2, band present in Fc Western, but only background band in propeptide Western).

In summary, in transiently transfected HEK 293 cells, only PC5 demonstrated the ability to completely remove the propeptide (FIG. 7), while PC7-SOL (FIG. 7) and KEX2-SOL (FIG. 8) were unable to process proFIX-Fc, similar to FIX-Fc transfected without any processing enzyme (FIG. 7).

The ability of these enzymes to remove the propeptide was also examined in stably transfected HEK 293 cells. FIG. 9 demonstrates that in stably transfected cell lines, PC5 is capable of fully processing the propeptide. Two lots of purified FIX-Fc monomer (see Example 11 for purification process) from a HEK 293-H cell line stably expressing FIX-Fc dimer, monomer, and Fc cotransfected with PC5 were run in duplicate (lanes 4a/b and 5a/b) on an SDS-PAGE gel under non-reducing conditions, then transferred to blots and probed with FIX (FIG. 9B) or propeptide (FIG. 9C) antibodies. The gel was then stained after transfer with Gelcode Blue (Pierce, Rockford, Ill.) (FIG. 9A). Analysis of the figures demonstrates that the propeptide was fully processed by PC5, as indicated by the absence of bands in panel C, propeptide Western, lanes 4b and 5b. As can be seen from panel A, lanes 4a/b and 5a/b were all loaded with equal amounts of protein, confirmed to be FIX-Fc dimer and monomer, as can be seen in panel B, lanes 4a and 5a. As controls, protein A-purified FIX-Fc dimer, monomer, and Fc from CHO cell lines cotransfected with PACE-SOL (lanes 1a/b) or PC7-SOL (lanes 2a/b) were analyzed. These controls confirmed that the propeptide was present in the material cotransfected with PC7 (bands present in panel C, lane 2b, as well as panel B, lane 2a), but not PACE-SOL (bands absent in panel C, lane 2b, but present in panel B, lane 2a).

FIG. 10 demonstrates that, in contrast to PC5, PC7-SOL was incapable of processing the propeptide in stably transfected HEK 293 cell lines. As shown in FIG. 10, media from HEK 293-H cells stably transfected either with FIX-Fc and Fc alone, or with FIX-Fc, Fc, and PC7-SOL were subject to protein A pulldowns and analyzed by reducing SDS-PAGE and Fc Western blotting (top panel) or FIX propeptide Western blotting (bottom panel). The cells were transfected with the N297A version of FIX-Fc and Fc in either equal ratios (lanes 3 and 5) or in a 1:8 ratio (lanes 4 and 6) of FIX-Fc to Fc expression plasmids, respectively, either alone (lanes 3 and 4) or with ⅒ the total DNA of PC7-SOL expression plasmid (lanes 5 and 6). These analyses showed that the FIX-Fc protein retains the propeptide whether stably transfected with (lanes 5 and 6) or without (lanes 3 and 4) PC7-SOL, as can be seen by bands in both the Fc Western blot (top panel) and propeptide Western blot (bottom panel). As controls for these Westerns, FIX-Fc dimer purified from CHO cells transfected alone (lane 1) or with PACE-SOL (lane 2) were analyzed, confirming that the propeptide was present on FIX-Fc transfected without any processing enzyme (bands in both Westerns, lane 1) but absent in FIX-Fc contransfected with PACE-SOL (lane 2, band present in Fc Western, but only faint background band in propeptide Western).

In summary, stable HEK 293 cell lines appeared identical to the transient transfections, in that PC5 was able to completely process the propeptide (FIG. 9) while PC7 was not (FIG. 10).

Table 2 below summarizes the results of the different combinations of processing enzymes and FIX-Fc proteins as assessed by Western blotting.

TABLE 2

| | | Propeptide Processing | | | | |
|---|---|---|---|---|---|---|
| Cell | Transfection | PC5 | Kex2 | PC7 | PACE | PACE 4 |
| CHO | transient | processes FIG. 4 | processes (cryptic cleavage) FIG. 4 | processes FIG. 4 | processes FIG. 4 | |

TABLE 2-continued

Propeptide Processing

| Cell | Transfection | PC5 | Kex2 | PC7 | PACE | PACE 4 |
|------|--------------|-----|------|-----|------|--------|
|      | stable | processes FIG. 6 | not done | does not fully process FIG. 5 | process FIG. 5, 6 | does not fully process* |
| HEK | transient | processes FIG. 7 | does not fully process FIG. 8 | does not fully process FIG. 7 | not done | |
|      | stable | processes FIG. 9 | not done | does not fully process FIG. 10 | not done | |

*Wasley LC et al. (1993) J Biol Chem. 268: 8458-65.

Example 11

Protein Purification

Protein A Chromatography

A 5 cm×6 cm bed height column (117 ml volume, XK 5 column, Amersham) was packed with MabSelect media according to manufacturer's specifications. The column was equilibrated with PBS and then loaded with the concentrated media at 150 cm/h, providing a retention time of 2.4 minutes. Following loading, the column was first washed with 3-4 volumes of PBS, then 3-4 volumes of PBS+0.9 M NaCl. Finally, the conductivity was lowered with 3 volumes of PBS prior to elution. The bound protein eluted with 3-4 volumes of 25 mM Sodium Citrate+150 mM NaCl, pH 3.4. Following elution the column was stripped with 3 M Guanidine HCl. The eluted material was neutralized with 2 M Tris base 8 ml per 100 ml of eluate). The amount of protein eluted was estimated by measuring the triplicate dilutions of the neutralized pool (1 in 10) in PBS. The concentration was determined using the equation mg/ml=(absorbance 280−absorbance 320)/1.34 where 1.34 is the theoretical molar absorbance coefficient based on the number of tryptophans, tyrosines and disulfide bonds in FIX-Fc monomer. Gill et al. (1989) *Analytical Biochem* 182:319.

Anion Exchange Chromatography Using Fractogel DEAE

The neutralized Protein A eluate was diluted 1:1 with 25 mM Tris+150 mM NaCl, pH 7.5, and loaded on a 2.6 cm×7 cm bed height Fractogel DEAE column (37 ml Volume, XK 2.6 column, Amersham). The Fractogel DEAE column was packed according to the manufacturer's specifications, which included 25% bed compression after packing by high flow.

The column was equilibrated with 6 column volumes (CV) of 25 mM Tris+150 mM NaCl, pH 7.5, and loaded at ~230 cm/h. The load was washed with 4 CV of equilibration buffer followed by 4 CV of 25 mM Tris+350 mM Ammonium Acetate, pH 7.5, followed by 3 CV of equilibration buffer.

The FIX-Fc monomer eluted with 25 mM Tris+600 mM Ammonium Acetate, pH 7.5 (~5 CV). The column was then stripped with 5 volumes of 0.1 M Sodium Hydroxide, followed by re-equilibration with 4 CV of 25 mM Tris+150 mM NaCl, pH 7.5.

Pseudoaffinity Chromatography Using Q Sepharose FF

Pseudoaffinity anion exchange chromatography involves $CaCl_2$ in eluting the immobilized FIX-Fc from the column. The addition of $CaCl_2$ is believed to cause a conformational change in the FIX part of the molecule that causes it to elute from the Q Sepharose FF media. Yan S B et al. (1996) *J Mol Recognit.* 9:211-8; Harrison S et al. (1998) *Semin Hematol* 35(2 Suppl 2):4-10.

The DEAE eluate was diluted a total of 4-fold with 25 mM Tris+150 mM NaCl, pH 7.5. A 1.6 cm×11 cm bed height Q Seph FF column (22 ml volume, XK 1.6 column, Amersham) was equilibrated with 25 mM Tris+150 mM NaCl, pH 7.5 (9 CV). The column was then loaded at 200 cm/h and washed with 15 CV of equilibration buffer. To ensure adequate binding of the FIX-Fc active species, the DEAE load of new material is now diluted 1:4 with 25 mM Tris+120 mM NaCl, pH 7.5, which now becomes the column equilibration buffer. The rest of the procedure remains the same.

The most active FIX-Fc monomer species eluted with 25 mM Tris+7 mM $CaCl_2$+150 mM NaCl, pH 7.5 (5 CV). Less active species eluted with 25 mM Tris+10 mM $CaCl_2$+150 mM NaCl, pH 7.5 (5 CV), while least active FIX-Fc material eluted with 25 mM Tris+600 mM Ammonium Acetate, pH 7.5.

The rFIX-Fc peak was collected from the beginning of the elution (UV signal reaches ~100 mAU) to when the UV signal reaches 20% of the maximum peak absorbance at the back end of the elution peak (~30 mL).

The column was then stripped with 0.1 M Sodium Hydroxide (5 CV) and then re-equilibrated with 25 mM Tris+150 mM NaCl, pH 7.5.

Buffer Exchange of Final Protein Preparation

The Q Seph FF elution fractions were buffer exchanged against PBS. The protein was injected in pre-wetted 125 ml Slide-A-lyzers (Pierce) and was dialyzed to against two changes of PBS buffer, each time in excess of 200-fold PBS over protein solution.

Example 12

Analysis of Stable Cell Line and Peptide Mapping

For peptide mapping, tryptic digests were performed and the resulting peptides analyzed by LC/MS to determine the presence of a fragment of the propeptide designated the propeptide indicator peptide, or PIP (TVFLDHENANK; SEQ ID NO:18), that would only be present in the case of incomplete propeptide processing.

Approximately 100-200 µg of protein was dried down with a Speed Vac, then resuspended in 100-200 µl of digestion buffer (50 mM ammonium bicarbonate) using an Eppendorf Thermal Mixer at 30° C., 800 rpm, for 30 min. The sample was then reduced by adding 10 µl reducing agent (10 mM dithiothreitol in digest buffer) for 30 min at 56° C., 800 rpm on the Thermal Mixer. The sample was allowed to cool, then 10 µl of alkylating agent (55 mM iodoacetamide in digest buffer) was added and allowed to incubate for 30 mM at room temperature in the dark. Promega Sequencing Grade Modified Trypsin at 0.1 µg/µl in 50 mM ammonium bicarbonate was then added at 100:1 to 200:1 substrate to enzyme weight ratio, then incubated at 37° C., 800 rpm for 16 hours. The sample was dried down somewhat with a Speed Vac as necessary to reduce volume, and the samples stored at −20° C. until ready for analysis, as described below.

HPLC-UV Analysis—Materials and Equipment:
  Agilent 1100 binary HPLC pump with thermostatted autosampler, Diode Array Detector, and column heater
  Phenomenex Jupiter HPLC Column, 250 mm×2.00 mm, C18, 300 Å, 5 μm dp
  Buffer A: 0.01% (v/v) Trifluoroacetic Acid, 0.05% (v/v) Formic Acid. (in-house HPLC grade water, analytical grade reagents)
  Buffer B: Buffer A in 85% HPLC grade Acetonitrile HPLC-UV-MS Analysis—Materials and Equipment:
  Agilent 1100 binary HPLC pump with thermostatted autosampler, Diode Array Detector, and column heater
  Thermo Finnigan Ion Trap Mass Spectrometer
  Phenomenex Jupiter HPLC Column, 250 mm×2.00 mm, C18, 300 Å, 5 μm dp
  Buffer A: 0.01% (v/v) Trifluoroacetic Acid, 0.05% (v/v) Formic Acid. (in-house HPLC grade water, analytical grade reagents)
  Buffer B: Buffer A in 85% HPLC grade Acetonitrile HPLC-UV Analysis—Procedure:
  Gradient Program:

| Time, min | % Solvent B |
|---|---|
| 0.00 | 5.6 |
| 25.00 | 16.8 |
| 50.00 | 21.3 |
| 71.00 | 29.0 |
| 91.00 | 32.5 |
| 125.00 | 44.7 |
| 130.00 | 100 |
| 140.00 | 100 |
| 140.10 | 5.6 |
| 155.00 | 5.6 |

Flowrate: 0.250 ml/min;
Detection: Diode Array Detector, UV, 214 nm and 280 nm;
Column Temperature: 30° C.

HPLC-UV-MS Analysis—Procedure:
  Gradient Program, Flowrate, Column Temperature, and UV Detection as above.

MS Detection: A Thermo Finnigan LCQ Advantage Ion Trap Mass Spectrometer connected in-line after the Diode Array Detector and operated in the Electrospray Ionization (ESI) mode. Mass spectrometric protocols varied depending on the goal of the analysis, but were usually either "Triple Play" (sequential full scan, zoom scan, and MSMS scan) for identification of peptides or full scan only to produce mass chromatograms.

Example 13

Summary of Propeptide Processing Experiments

Peptide Mapping

Figure 11A:
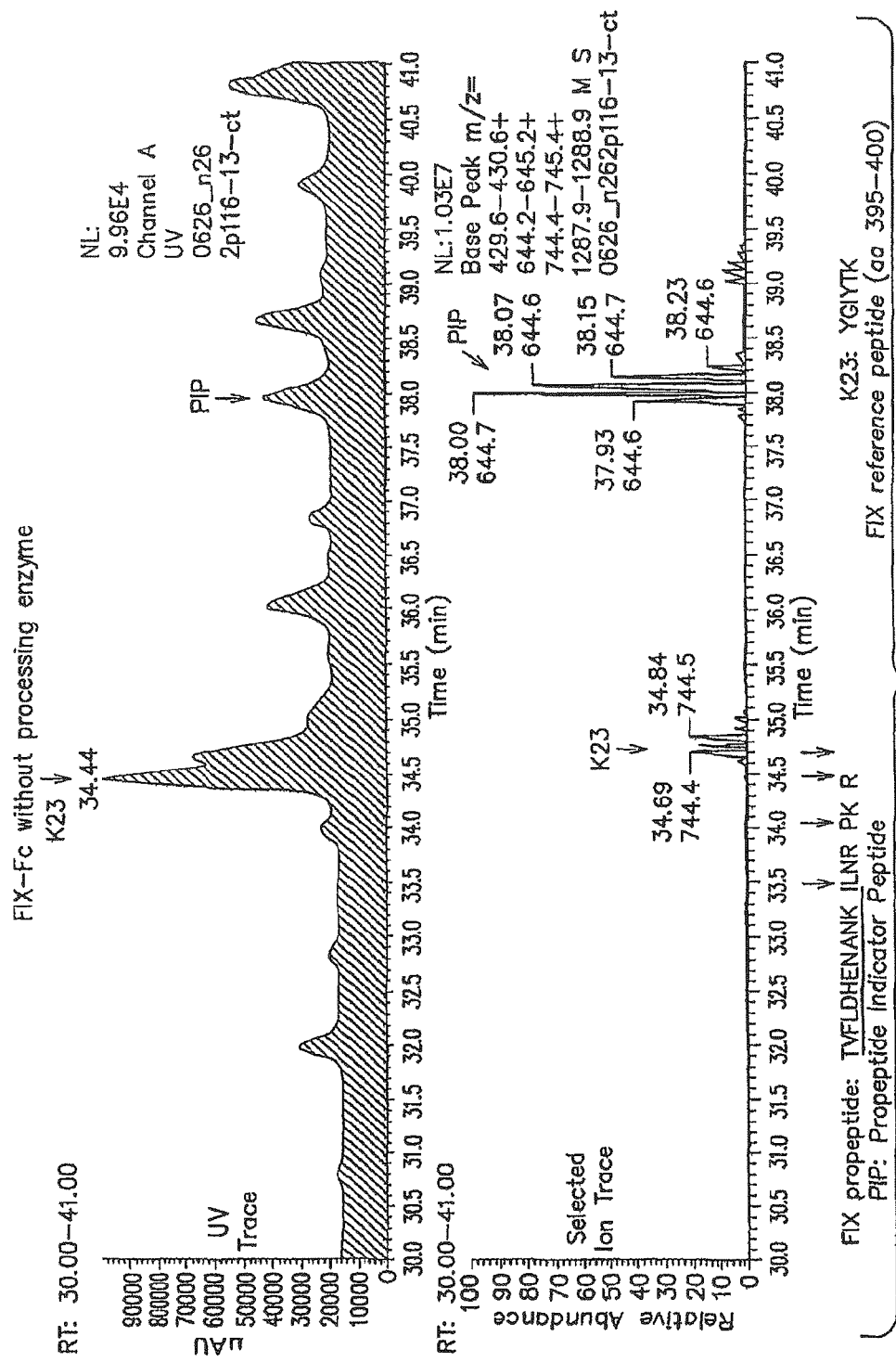
FIG. 11 shows peptide mapping data indicating the presence of proFIX-Fc in purified CHO-produced FIX-Fc without any processing enzyme, and the absence of proFIX-Fc from purified HEK-produced FIX-Fc monomer-dimer hybrid (monomer) with PC5. TVFLDHENANKILNRPKR, SEQ ID NO:17; YGIYTK, SEQ ID NO:19.
Figure 11B:
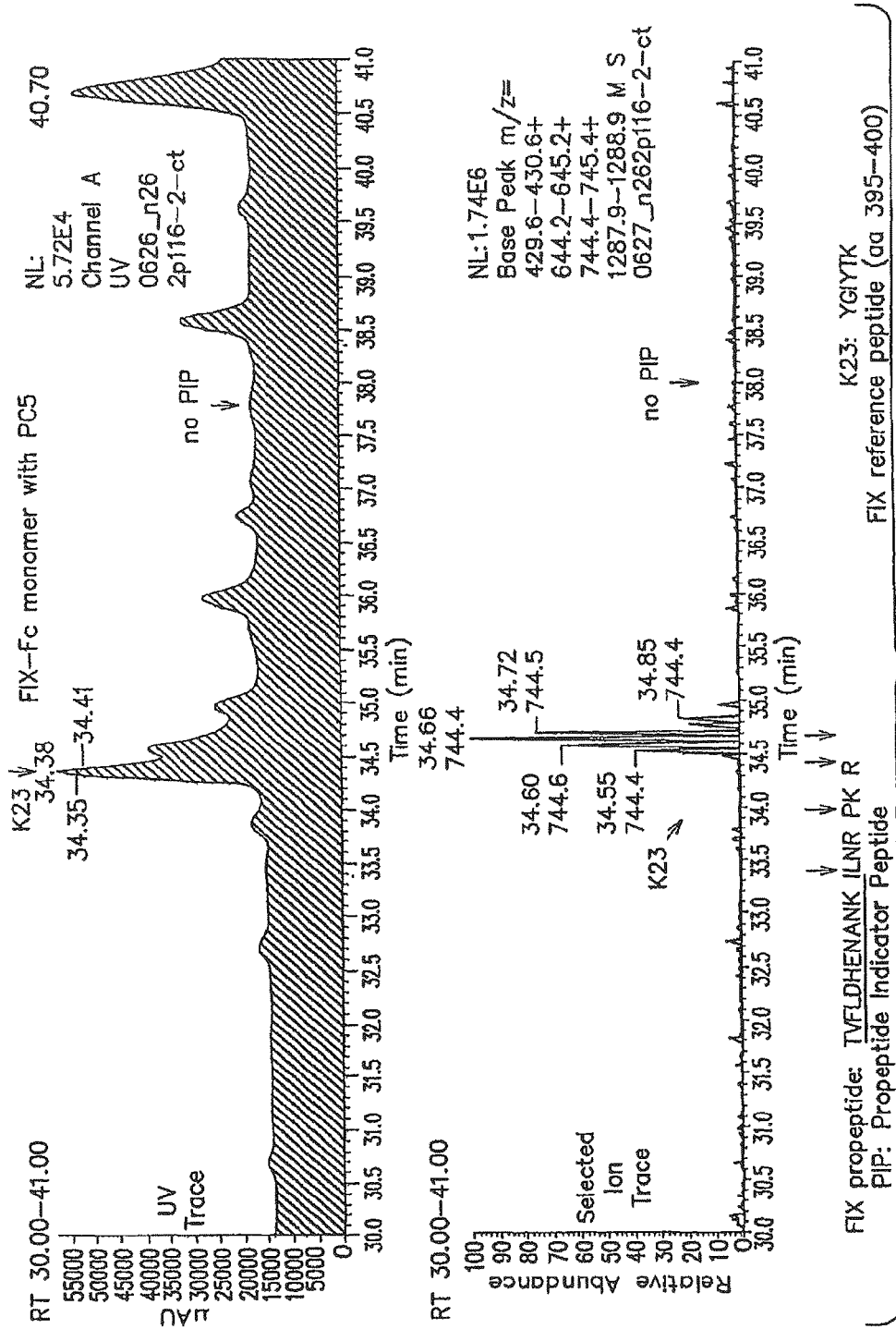
Figure 12A:
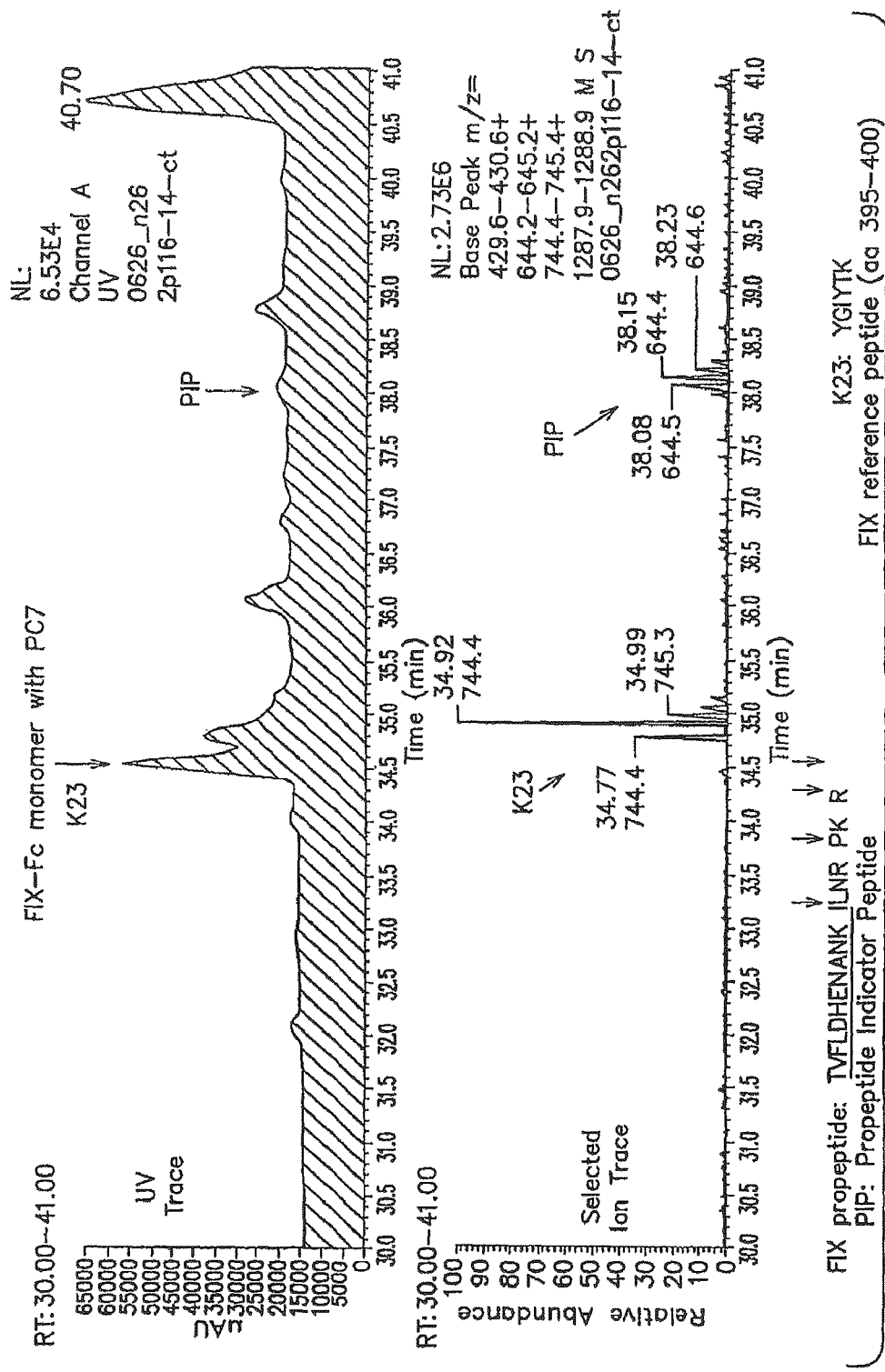
FIG. 12 shows peptide mapping data indicating the presence of proFIX-Fc in purified CHO-produced FIX-Fc with PC7-SOL, and the absence of proFIX-Fc from purified HEK-produced FIX-Fc monomer-dimer hybrid (monomer) with PC5. TVFLDHENANKILNRPKR, SEQ ID NO:17; YGIYTK, SEQ ID NO:19.
Figure 12B:
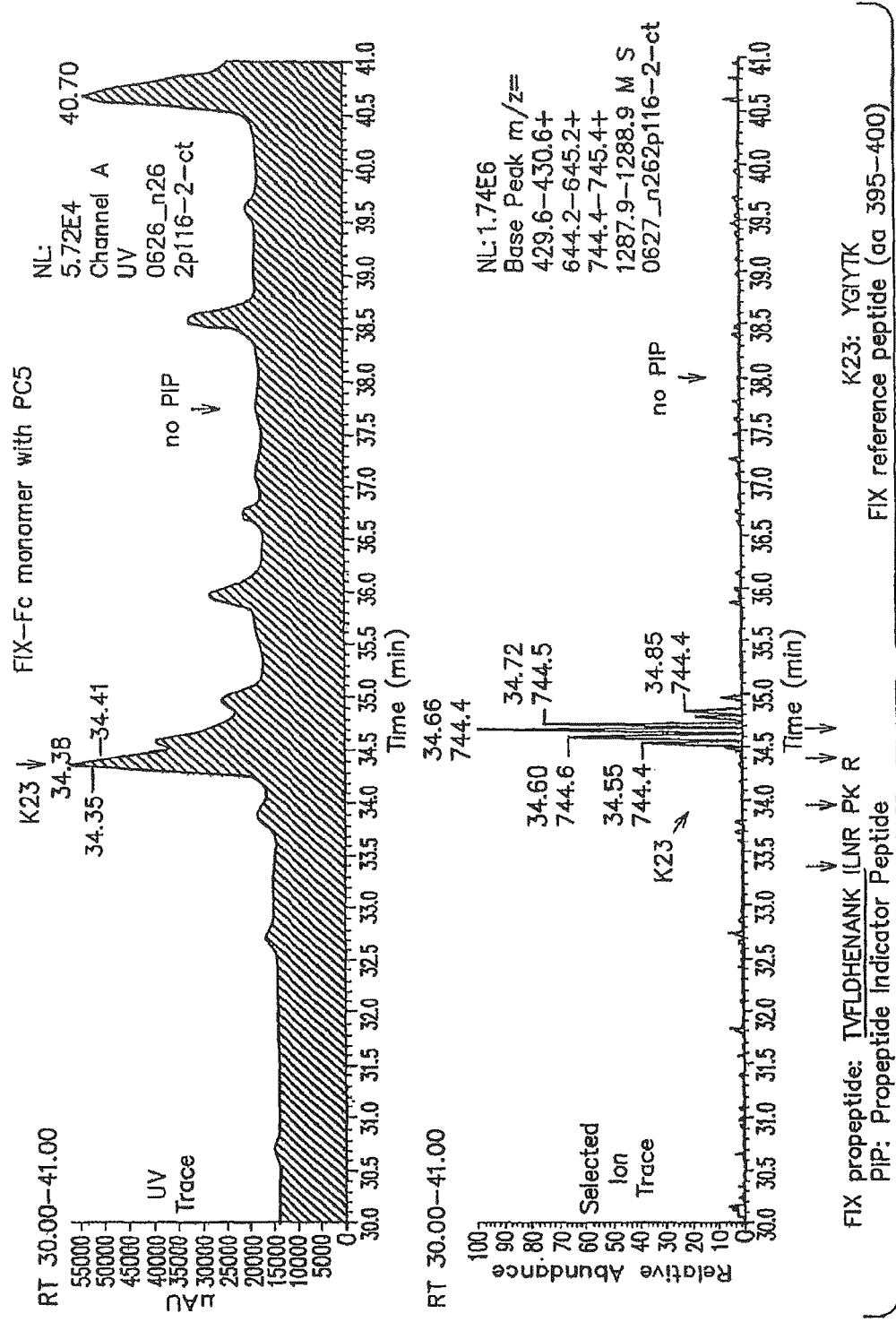
Figure 13A:
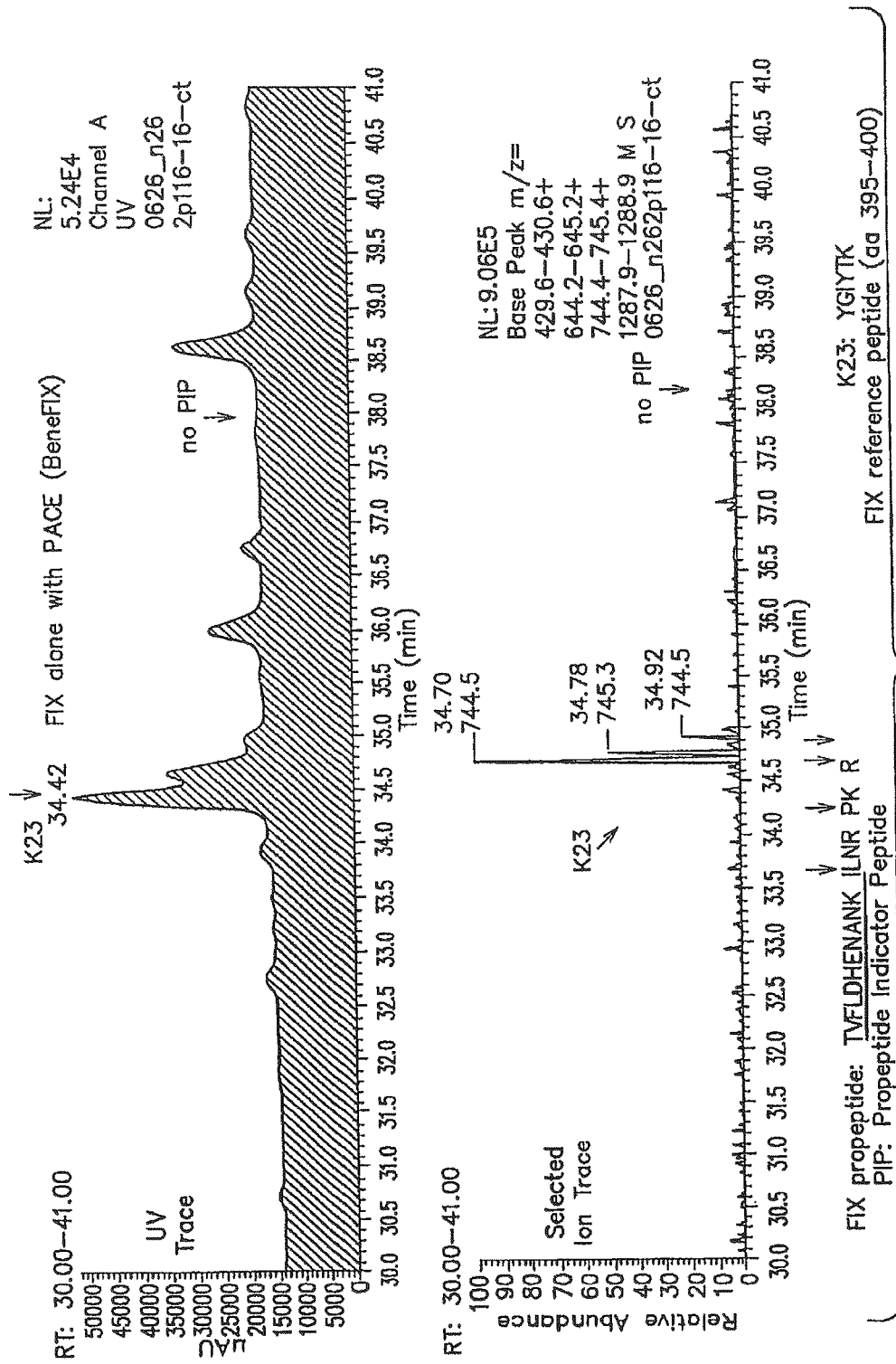
FIG. 13 shows peptide mapping data indicating the absence of propeptide from purified HEK-produced FIX-Fc monomer-dimer hybrid (monomer) with PC5 and from CHO-produced Factor IX alone. TVFLDHENANKILNRPKR, SEQ ID NO:17; YGIYTK, SEQ ID NO:19.
Figure 13B:
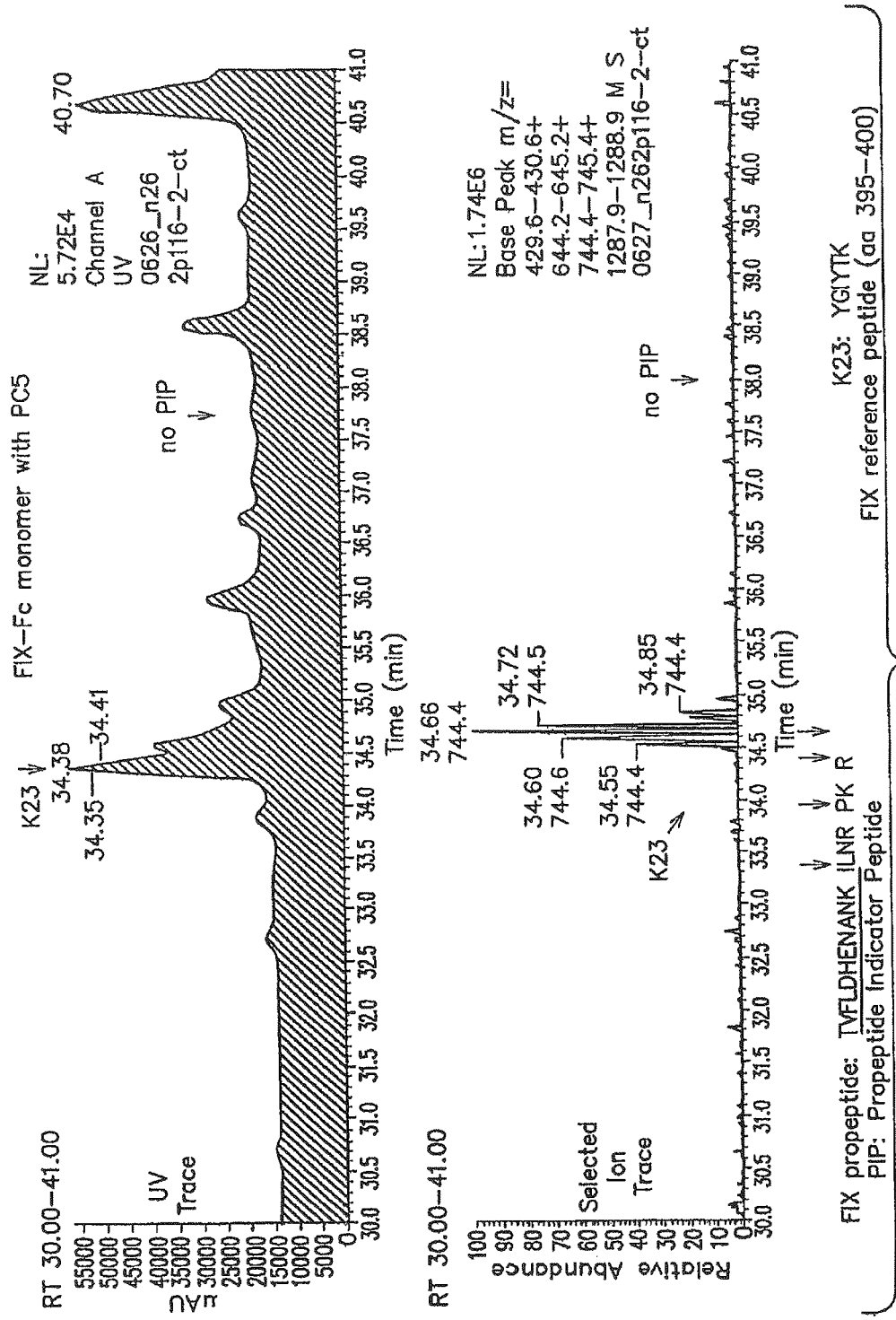

Western blotting results of stably transfected proteins were confirmed by peptide mapping. The propeptide indicator peptide (PIP) was detected both in the UV trace and selected ion trace in CHO FIX-Fc transfected alone, but undetectable in purified FIX-Fc monomer cotransfected with PC5 (FIG. 11). ProFIX-Fc was also found in CHO FIX-Fc protein that was contransfected with PC7, although possibly at lower levels as indicated in the UV trace (FIG. 12). FIX alone produced in the presence of PACE-SOL (BeneFIX®) appeared identical to FIX-Fc monomer produced with PC5 (FIG. 13), displaying no detectable PIP.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. The entire contents of all of the references (including literature references, issued patents, published patent applications, and co-pending patent applications) cited throughout this application are hereby expressly incorporated by reference.

---

What is claimed is:

1. An isolated host cell comprising a first polynucleotide and a second polynucleotide, wherein the first polynucleotide encodes a proprotein of Factor IX (proFIX) or a fusion protein comprising said proFIX, and the second polynucleotide encodes a functional PC5.

2. The host cell of claim 1, wherein the functional PC5 comprises SEQ ID NO: 1.

3. The host cell of claim 1, wherein the fusion protein comprises proFIX fused to a heterologous polypeptide.

4. The host cell of claim 3, wherein the fusion protein further comprises a linker connecting the proFIX and the heterologous polypeptide.

5. The host cell of claim 4, wherein said linker is selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

6. The host cell of claim 3, wherein the heterologous polypeptide is selected from the group consisting of an FcRn binding partner, albumin, and transferrin.

7. The host cell of claim 6, wherein said FcRn binding partner comprises Fc.

8. The host cell of claim 7, wherein said Fc is dimerized to a second Fc, forming proFIX-Fc monomer-dimer hybrid.

9. The host cell of claim 1, wherein the proFIX or fusion protein comprising said proFIX is modified, wherein said modification is selected from the group consisting of glycosylation, acetylation, phosphorylation, PEGylation, addition of a lipid moiety, and addition of any organic or inorganic molecule.

10. The host cell of claim 1, wherein the first polynucleotide and the second polynucleotide are in separate vectors.

11. The host cell of claim 1, wherein the first polynucleotide and the second polynucleotide are in a single vector.

12. The host cell of claim 1, which is a prokaryotic cell.

13. The host cell of claim 12, wherein the prokaryotic cell is *E. coli*.

14. The host cell of claim 1, which is an eukaryotic cell.

15. The host cell of claim 14, wherein said cell is selected from the group consisting of a HEK293 cell, a CHO cell, a HeLa cell, and a BHK cell.

16. A method of producing mature Factor IX or a fusion protein comprising mature Factor IX comprising culturing the host cell of claim 1 under conditions that allow expression of the proFIX or the fusion protein comprising said proFIX and the functional PC5 such that, upon expression, said PC5 cleaves proFIX or the fusion protein comprising said proFIX.

17. The method of claim 16, wherein said method increases yield of the mature Factor IX or fusion protein comprising mature Factor IX compared to the yield of mature Factor IX or a fusion protein comprising mature Factor IX produced under similar conditions without processing by the functional PC5.

18. The method of claim 17, wherein the functional PC5 comprises SEQ ID NO: 1.

19. The method of claim 17, wherein the fusion protein comprises a proFIX fused to a heterologous polypeptide.

20. The method of claim 19, wherein the heterologous polypeptide is selected from the group consisting of an FcRn binding partner, albumin, and transferrin.

21. The method of claim 20, wherein said FcRn binding partner comprises Fc.

22. The method of claim 21, wherein said Fc is dimerized to a second Fc, forming proFIX-Fc monomer-dimer hybrid.

23. The method of claim 17, wherein the proFIX or fusion protein comprising proFIX is modified, wherein said modification is selected from the group consisting of glycosylation, acetylation, phosphorylation, PEGylation, addition of a lipid moiety, and addition of any organic or inorganic molecule.

* * * * *

SEQUENCE LISTING

```
<160> NUMBER OF SEQ ID NOS: 68

<210> SEQ ID NO 1
<211> LENGTH: 913
<212> TYPE: PRT
<213> ORGANISM: Homo sapiens
<220> FEATURE:
<223> OTHER INFORMATION: human PC5A

<400> SEQUENCE: 1

Met Gly Trp Gly Ser Arg Cys Cys Cys Pro Gly Arg Leu Asp Leu Leu
1               5                   10                  15

Cys Val Leu Ala Leu Leu Gly Gly Cys Leu Leu Pro Val Cys Arg Thr
            20                  25                  30

Arg Val Tyr Thr Asn His Trp Ala Val Lys Ile Ala Gly Gly Phe Pro
        35                  40                  45
```

```
Glu Ala Asn Arg Ile Ala Ser Lys Tyr Gly Phe Ile Asn Ile Gly Gln
         50                  55                  60

Ile Gly Ala Leu Lys Asp Tyr Tyr His Phe Tyr His Ser Arg Thr Ile
 65                  70                  75                  80

Lys Arg Ser Val Ile Ser Ser Arg Gly Thr His Ser Phe Ile Ser Met
                     85                  90                  95

Glu Pro Lys Val Glu Trp Ile Gln Gln Gln Val Val Lys Lys Arg Thr
                100                 105                 110

Lys Arg Asp Tyr Asp Phe Ser Arg Ala Gln Ser Thr Tyr Phe Asn Asp
            115                 120                 125

Pro Lys Trp Pro Ser Met Trp Tyr Met His Cys Ser Asp Asn Thr His
        130                 135                 140

Pro Cys Gln Ser Asp Met Asn Ile Glu Gly Ala Trp Lys Arg Gly Tyr
145                 150                 155                 160

Thr Gly Lys Asn Ile Val Val Thr Ile Leu Asp Asp Gly Ile Glu Arg
                    165                 170                 175

Thr His Pro Asp Leu Met Gln Asn Tyr Asp Ala Leu Ala Ser Cys Asp
                180                 185                 190

Val Asn Gly Asn Asp Leu Asp Pro Met Pro Arg Tyr Asp Ala Ser Asn
            195                 200                 205

Glu Asn Lys His Gly Thr Arg Cys Ala Gly Glu Val Ala Ala Ala Ala
        210                 215                 220

Asn Asn Ser His Cys Thr Val Gly Ile Ala Phe Asn Ala Lys Ile Gly
225                 230                 235                 240

Gly Val Arg Met Leu Asp Gly Asp Val Thr Asp Met Val Glu Ala Lys
                    245                 250                 255

Ser Val Ser Phe Asn Pro Gln His Val His Ile Tyr Ser Ala Ser Trp
                260                 265                 270

Gly Pro Asp Asp Asp Gly Lys Thr Val Asp Gly Pro Ala Pro Leu Thr
            275                 280                 285

Arg Gln Ala Phe Glu Asn Gly Val Arg Met Gly Arg Arg Gly Leu Gly
        290                 295                 300

Ser Val Phe Val Trp Ala Ser Gly Asn Gly Gly Arg Ser Lys Asp His
305                 310                 315                 320

Cys Ser Cys Asp Gly Tyr Thr Asn Ser Ile Tyr Thr Ile Ser Ile Ser
                    325                 330                 335

Ser Thr Ala Glu Ser Gly Lys Lys Pro Trp Tyr Leu Glu Glu Cys Ser
                340                 345                 350

Ser Thr Leu Ala Thr Thr Tyr Ser Ser Gly Glu Ser Tyr Asp Lys Lys
            355                 360                 365

Ile Ile Thr Thr Asp Leu Arg Gln Arg Cys Thr Asp Asn His Thr Gly
        370                 375                 380

Thr Ser Ala Ser Ala Pro Met Ala Ala Gly Ile Ile Ala Leu Ala Leu
385                 390                 395                 400

Glu Ala Asn Pro Phe Leu Thr Trp Arg Asp Val Gln His Val Ile Val
                    405                 410                 415

Arg Thr Ser Arg Ala Gly His Leu Asn Ala Asn Asp Trp Lys Thr Asn
                420                 425                 430

Ala Ala Gly Phe Lys Val Ser His Leu Tyr Gly Phe Gly Leu Met Asp
            435                 440                 445

Ala Glu Ala Met Val Met Glu Ala Glu Lys Trp Thr Thr Val Pro Arg
450                 455                 460

Gln His Val Cys Val Glu Ser Thr Asp Arg Gln Ile Lys Thr Ile Arg
```

```
                465                 470                 475                 480
          Pro Asn Ser Ala Val Arg Ser Ile Tyr Lys Ala Ser Gly Cys Ser Asp
                          485                 490                 495

Asn Pro Asn Arg His Val Asn Tyr Leu Glu His Val Val Arg Ile
                          500                 505                 510

Thr Ile Thr His Pro Arg Arg Gly Asp Leu Ala Ile Tyr Leu Thr Ser
                          515                 520                 525

Pro Ser Gly Thr Arg Ser Gln Leu Leu Ala Asn Arg Leu Phe Asp His
                          530                 535                 540

Ser Met Glu Gly Phe Lys Asn Trp Glu Phe Met Thr Ile His Cys Trp
          545                 550                 555                 560

Gly Glu Arg Ala Ala Gly Asp Trp Val Leu Glu Val Tyr Asp Thr Pro
                          565                 570                 575

Ser Gln Leu Arg Asn Phe Lys Thr Pro Gly Lys Leu Lys Glu Trp Ser
                          580                 585                 590

Leu Val Leu Tyr Gly Thr Ser Val Gln Pro Tyr Ser Pro Thr Asn Glu
                          595                 600                 605

Phe Pro Lys Val Glu Arg Phe Arg Tyr Ser Arg Val Glu Asp Pro Thr
                          610                 615                 620

Asp Asp Tyr Gly Thr Glu Asp Tyr Ala Gly Pro Cys Asp Pro Glu Cys
          625                 630                 635                 640

Ser Glu Val Gly Cys Asp Gly Pro Gly Pro Asp His Cys Asn Asp Cys
                          645                 650                 655

Leu His Tyr Tyr Tyr Lys Leu Lys Asn Asn Thr Arg Ile Cys Val Ser
                          660                 665                 670

Ser Cys Pro Pro Gly His Tyr His Ala Asp Lys Lys Arg Cys Arg Lys
                          675                 680                 685

Cys Ala Pro Asn Cys Glu Ser Cys Phe Gly Ser His Gly Asp Gln Cys
          690                 695                 700

Met Ser Cys Lys Tyr Gly Tyr Phe Leu Asn Glu Glu Thr Asn Ser Cys
          705                 710                 715                 720

Val Thr His Cys Pro Asp Gly Ser Tyr Gln Asp Thr Lys Lys Asn Leu
                          725                 730                 735

Cys Arg Lys Cys Ser Glu Asn Cys Lys Thr Cys Thr Glu Phe His Asn
                          740                 745                 750

Cys Thr Glu Cys Arg Asp Gly Leu Ser Leu Gln Gly Ser Arg Cys Ser
                          755                 760                 765

Val Ser Cys Glu Asp Gly Arg Tyr Phe Asn Gly Gln Asp Cys Gln Pro
          770                 775                 780

Cys His Arg Phe Cys Ala Thr Cys Ala Gly Ala Gly Ala Asp Gly Cys
          785                 790                 795                 800

Ile Asn Cys Thr Glu Gly Tyr Phe Met Glu Asp Gly Arg Cys Val Gln
                          805                 810                 815

Ser Cys Ser Ile Ser Tyr Tyr Phe Asp His Ser Ser Glu Asn Gly Tyr
                          820                 825                 830

Lys Ser Cys Lys Lys Cys Asp Ile Ser Cys Leu Thr Cys Asn Gly Pro
                          835                 840                 845

Gly Phe Lys Asn Cys Thr Ser Cys Pro Ser Gly Tyr Leu Leu Asp Leu
                          850                 855                 860

Gly Met Cys Gln Met Gly Ala Ile Cys Lys Asp Ala Thr Glu Glu Ser
          865                 870                 875                 880

Trp Ala Glu Gly Gly Phe Cys Met Leu Val Lys Lys Asn Asn Leu Cys
                          885                 890                 895
```

```
        Gln Arg Lys Val Leu Gln Gln Leu Cys Cys Lys Thr Cys Thr Phe Gln
                900                 905                 910
Gly

<210> SEQ ID NO 2
<211> LENGTH: 2739
<212> TYPE: DNA
<213> ORGANISM: Homo sapiens
<220> FEATURE:
<223> OTHER INFORMATION: human PC5A

<400> SEQUENCE: 2
atgggctggg ggagccgctg ctgctgcccg ggacgtttgg acctgctgtg cgtgctggcg      60
ctgctcgggg gctgcctgct ccccgtgtgt cggacgcgcg tctacaccaa ccactgggca     120
gtcaaaatcg ccgggggctt cccggaggcc aaccgtatcg ccagcaagta cggattcatc     180
aacataggac agatagggc cctgaaggac tactaccact tctaccatag caggacgatt     240
aaaaggtcag ttatctcgag cagagggacc cacagtttca tttcaatgga accaaaggtg     300
gaatggatcc aacagcaagt ggtaaaaaag cggacaaaga gggattatga cttcagtcgt     360
gcccagtcta cctatttcaa tgatcccaag tggcccagca tgtggtatat gcactgcagt     420
gacaatacac atccctgcca gtctgacatg aatatcgaag agcctggaa gagaggctac     480 acgggaaaga acattgtggt cactatcctg gatgacggaa ttgagagaac ccatccagat     540
ctgatgcaaa actacgatgc tctggcaagt tgcgacgtga atgggaatga cttggaccca     600
atgcctcgtt atgatgcaag caacgagaac aagcatggga ctcgctgtgc tggagaagtg     660
gcagccgctg caaacaattc gcactgcaca gtcggaattg ctttcaacgc caagatcgga     720
ggagtgcgaa tgctggacgg agatgtcacg gacatggttg aagcaaaatc agttagcttc     780 aaccccccagc acgtgcacat ttacagcgcc agctggggcc cggatgatga tggcaagact     840
gtggacggac cagcccccct cacccggcaa gcctttgaaa acggcgttag aatgggcgg     900 agaggcctcg gctctgtgtt tgtttgggca tctggaaatg gtggaaggag caaagaccac     960
tgctcctgtg atggctacac caacagcatc tacaccatct ccatcagcag cactgcagaa    1020
agcggaaaga accttggta cctggaagag tgttcatcca cgctggccac aacctacagc    1080 agcgggagt cctacgataa gaaaatcatc actacagatc tgaggcagcg ttgcacggac    1140
aaccacactg ggacgtcagc ctcagcccc atggctgcag catcattgc gctggccctg    1200 gaagccaatc cgtttctgac ctggagagac gtacagcatg ttattgtcag acttcccgt    1260 gcgggacatt tgaacgctaa tgactggaaa accaatgctg ctggttttaa ggtgagccat    1320
ctttatggat ttggactgat ggacgcagaa gccatggtga tggaggcaga aagtggacc    1380 accgttcccc ggcagcacgt gtgtgtggag agcacagacc gacaaatcaa gacaatccgc    1440
cctaacagtg cagtgcgctc catctacaaa gcttcaggct gctcggataa ccccaaccgc    1500
catgtcaact acctggagca cgtcgttgtg cgcatcacca tcacccaccc caggagagga    1560
gacctggcca tctacctgac ctcgcccctct ggaactaggt ctcagctttt ggccaacagg    1620
ctatttgatc actccatgga aggattcaaa actgggagt catgaccat tcattgctgg    1680 ggagaaagag ctgctggtga ctgggtcctt gaagtttatg atactccctc tcagctaagg    1740
aactttaaga ctccaggtaa attgaaagaa tggtcttttg tcctctacgg cacctccgtg    1800
cagccatatt caccaaccaa tgaatttccg aaagtggaac ggttccgcta gccgagtt      1860 gaagacccca cagacgacta tggcacagag gattatgcag gtccctgcga ccctgagtgc    1920
agtgaggttg gctgtgacgg gccaggacca gaccactgca atgactgttt gcactactac    1980
```

```
tacaagctga aaacaatac caggatctgt gtctccagct gcccccctgg ccactaccac    2040
gccgacaaga agcgctgcag gaagtgtgcc cccaactgtg agtcctgctt tgggagccat    2100
ggtgaccaat gcatgtcctg caaatatgga tactttctga atgaagaaac caacagctgt    2160
gttactcact gccctgatgg gtcatatcag gataccaaga aaaatctttg ccggaaatgc    2220
agtgaaaact gcaagacatg tactgaattc cataactgta cagaatgtag ggatgggtta    2280
agcctgcagg gatcccggtg ctctgtctcc tgtgaagatg acggtatttt caacggccag    2340
gactgccagc cctgccaccg cttctgcgcc acttgtgctg gggcaggagc tgatgggtgc    2400
attaactgca cagagggcta cttcatggag gatgggagat gcgtgcagag ctgtagtatc    2460
agctattact ttgaccactc ttcagagaat ggatacaaat cctgcaaaaa atgtgatatc    2520
agttgtttga cgtgcaatgg cccaggattc aagaactgta caagctgccc tagtgggtat    2580
ctcttagact aggaatgtg tcaaatggga gccatttgca aggatgcaac ggaagagtcc    2640
tgggcggaag gaggcttctg tatgcttgtg aaaaagaaca atctgtgcca acggaaggtt    2700
cttcaacaac tttgctgcaa acatgtaca tttcaaggc                            2739
```

<210> SEQ ID NO 3
<211> LENGTH: 461
<212> TYPE: PRT
<213> ORGANISM: Homo sapiens
<220> FEATURE:
<223> OTHER INFORMATION: human factor IX proprotein

<400> SEQUENCE: 3

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
```

```
                225                 230                 235                 240
Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460

<210> SEQ ID NO 4
<211> LENGTH: 1383
<212> TYPE: DNA
<213> ORGANISM: Homo sapiens
<220> FEATURE:
<223> OTHER INFORMATION: human factor IX proprotein

<400> SEQUENCE: 4
atgcagcgcg tgaacatgat catggcagaa tcaccaggcc tcatcaccat ctgccttta       60
ggatatctac tcagtgctga atgtacagtt tttcttgatc atgaaaacgc caacaaaatt      120
ctgaatcggc caaagaggta taattcaggt aaattggaag agtttgttca agggaacctt      180
gagagagaat gtatggaaga aaagtgtagt tttgaagaag cacgagaagt ttttgaaaac      240
actgaaagaa caactgaatt ttggaagcag tatgttgatg gagatcagtg tgagtccaat      300
ccatgtttaa atggcggcag ttgcaaggat gacattaatt cctatgaatg ttggtgtccc      360
tttggatttg aaggaaagaa ctgtgaatta gatgtaacat gtaacattaa gaatggcaga      420
tgcgagcagt ttgtaaaaa tagtgctgat aacaaggtgg tttgctcctg tactgaggga      480
tatcgacttg cagaaaacca gaagtcctgt gaaccagcag tgccatttcc atgtggaaga      540
gtttctgttt cacaaacttc taagctcacc cgtgctgaga ctgttttcc tgatgtggac      600
tatgtaaatt ctactgaagc tgaaaccatt ttggataaca tcactcaaag cacccaatca      660
tttaatgact tcactcgggt tgttggtgga gaagatgcca aaccaggtca attcccttgg      720
caggttgttt tgaatggtaa agttgatgca ttctgtggag gctctatcgt taatgaaaaa      780
```

```
tggattgtaa ctgctgccca ctgtgttgaa actggtgtta aaattacagt tgtcgcaggt    840
gaacataata ttgaggagac agaacataca gagcaaaagc gaaatgtgat tcgaattatt    900
cctcaccaca actacaatgc agctattaat aagtacaacc atgacattgc ccttctggaa    960
ctggacgaac ccttagtgct aaacagctac gttacaccta tttgcattgc tgacaaggaa   1020
tacacgaaca tcttcctcaa atttggatct ggctatgtaa gtggctgggg aagagtcttc   1080
cacaaaggga gatcagcttt agttcttcag taccttagag ttccacttgt tgaccgagcc   1140
acatgtcttc gatctacaaa gttcaccatc tataacaaca tgttctgtgc tggcttccat   1200
gaaggaggta gagattcatg tcaaggagat agtgggggac ccatgttac tgaagtggaa    1260 gggaccagtt tcttaactgg aattattagc tggggtgaag agtgtgcaat gaaaggcaaa   1320
tatggaatat ataccaaggt atcccggtat gtcaactgga ttaaggaaaa aacaaagctc   1380
act                                                                 1383
```

<210> SEQ ID NO 5
<211> LENGTH: 227
<212> TYPE: PRT
<213> ORGANISM: Homo sapiens
<220> FEATURE:
<223> OTHER INFORMATION: human Fc gamma

<400> SEQUENCE: 5

```
Asp Lys Thr His Thr Cys Pro Pro Cys Pro Ala Pro Glu Leu Leu Gly
  1               5                  10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
     50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 6
<211> LENGTH: 4

```
<212> TYPE: PRT
<213> ORGANISM: Homo sapiens

<400> SEQUENCE: 6

Glu Leu Leu Gly
1

<210> SEQ ID NO 7
<211> LENGTH: 8
<212> TYPE: PRT
<213> ORGANISM: Artificial sequence
<220> FEATURE:
<223> OTHER INFORMATION: synthetic peptide

<400> SEQUENCE: 7

Glu Phe Ala Gly Ala Ala Ala Val
1               5

<210> SEQ ID NO 8
<211> LENGTH: 10
<212> TYPE: PRT
<213> ORGANISM: Artificial sequence
<220> FEATURE:
<223> OTHER INFORMATION: synthetic peptide; with respect to position
      2-10 any one or more Gly units may be absent

<400> SEQUENCE: 8

Gly Gly Gly Gly Gly Gly Gly Gly Gly Gly
1               5                   10

<210> SEQ ID NO 9
<211> LENGTH: 20
<212> TYPE: PRT
<213> ORGANISM: Artificial sequence
<220> FEATURE:
<223> OTHER INFORMATION: synthetic peptide; with respect to position
      3-20 any one or more Gly-Ala units may be absent

<400> SEQUENCE: 9

Gly Ala Gly Ala Gly Ala Gly Ala Gly Ala Gly Ala Gly Ala Gly Ala
1               5                   10                  15

Gly Ala Gly Ala
            20

<210> SEQ ID NO 10
<211> LENGTH: 30
<212> TYPE: PRT
<213> ORGANISM: Artificial sequence
<220> FEATURE:
<223> OTHER INFORMATION: synthetic peptide; with respect to position
      4-30 any one or more Gly-Gly-Ser units may be absent

<400> SEQUENCE: 10

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 11
<211> LENGTH: 50
<212> TYPE: PRT
<213> ORGANISM: Artificial sequence
<220> FEATURE:
<223> OTHER INFORMATION: synthetic peptide; with respect to position
      6-50 any one or more Gly-Gly-Gly-Gly-Ser units may be absent

<400> SEQUENCE: 11
```

```
Gly Gly Gly Gly Ser Gly Gly Gly Ser Gly Gly Gly Ser Gly
1               5                  10                 15

Gly Gly Gly Ser Gly Gly Gly Ser Gly Gly Gly Ser Gly Gly
                20              25              30

Gly Gly Ser Gly Gly Gly Ser Gly Gly Gly Ser Gly Gly Gly
        35              40              45

Gly Ser
    50

<210> SEQ ID NO 12
<211> LENGTH: 7
<212> TYPE: PRT
<213> ORGANISM: Artificial sequence
<220> FEATURE:
<223> OTHER INFORMATION: synthetic peptide

<400> SEQUENCE: 12

Ser Gly Gly Ser Gly Gly Ser
1               5

<210> SEQ ID NO 13
<211> LENGTH: 15
<212> TYPE: PRT
<213> ORGANISM: Artificial sequence
<220> FEATURE:
<223> OTHER INFORMATION: synthetic peptide

<400> SEQUENCE: 13

Gly Gly Ser Gly Gly Ser Gly Gly Ser Gly Gly Ser Gly Gly Gly
1               5                  10                 15

<210> SEQ ID NO 14
<211> LENGTH: 16
<212> TYPE: PRT
<213> ORGANISM: Artificial sequence
<220> FEATURE:
<223> OTHER INFORMATION: synthetic peptide

<400> SEQUENCE: 14

Gly Gly Ser Gly Gly Ser Gly Gly Gly Gly Ser Gly Gly Gly Gly Ser
1               5                  10                  15

<210> SEQ ID NO 15
<211> LENGTH: 18
<212> TYPE: PRT
<213> ORGANISM: Artificial sequence
<220> FEATURE:
<223> OTHER INFORMATION: synthetic peptide

<400> SEQUENCE: 15

Gly Gly Ser Gly Gly Ser Gly Gly Ser Gly Gly Ser Gly Gly Ser Gly
1               5                  10                  15

Gly Ser

<210> SEQ ID NO 16
<211> LENGTH: 30
<212> TYPE: PRT
<213> ORGANISM: Artificial sequence
<220> FEATURE:
<223> OTHER INFORMATION: synthetic peptide

<400> SEQUENCE: 16

Gly Gly Gly Gly Ser Gly Gly Gly Gly Ser Gly Gly Gly Gly Ser Gly
1               5                  10                  15

Gly Gly Gly Ser Gly Gly Gly Gly Ser Gly Gly Gly Gly Ser
```

-continued

<210> SEQ ID NO 17
<211> LENGTH: 18
<212> TYPE: PRT
<213> ORGANISM: Homo sapiens

<400> SEQUENCE: 17

Thr Val Phe Leu Asp His Glu Asn Ala Asn Lys Ile Leu Asn Arg Pro
1               5                   10                  15
Lys Arg

<210> SEQ ID NO 18
<211> LENGTH: 11
<212> TYPE: PRT
<213> ORGANISM: Homo sapiens

<400> SEQUENCE: 18

Thr Val Phe Leu Asp His Glu Asn Ala Asn Lys
1               5                   10

<210> SEQ ID NO 19
<211> LENGTH: 6
<212> TYPE: PRT
<213> ORGANISM: Homo sapiens

<400> SEQUENCE: 19

Tyr Gly Ile Tyr Thr Lys
1               5

<210> SEQ ID NO 20
<211> LENGTH: 69
<212> TYPE: DNA
<213> ORGANISM: Artificial sequence
<220> FEATURE:
<223> OTHER INFORMATION: synthetic oligonucleotide

<400> SEQUENCE: 20
gctgcggtcg acaaaactca cacatgccca ccgtgcccag ctccggaact cctgggcgga     60
ccgtcagtc                                                            69

<210> SEQ ID NO 21
<211> LENGTH: 36
<212> TYPE: DNA
<213> ORGANISM: Artificial sequence
<220> FEATURE:
<223> OTHER INFORMATION: synthetic oligonucleotide

<400> SEQUENCE: 21
attggaattc tcatttaccc ggagacaggg agaggc                               36

<210> SEQ ID NO 22
<211> LENGTH: 102
<212> TYPE: DNA
<213> ORGANISM: Artificial sequence
<220> FEATURE:
<223> OTHER INFORMATION: synthetic oligonucleotide

<400> SEQUENCE: 22
tttaagcttg ccgccaccat ggagacagac acactcctgc tatgggtact gctgctctgg     60
gttccaggtt ccactggtga caaaactcac acatgcccac cg                       102

<210> SEQ ID NO 23
<211> LENGTH: 22

```
<212> TYPE: DNA
<213> ORGANISM: Artificial sequence
<220> FEATURE:
<223> OTHER INFORMATION: synthetic oligonucleotide

<400> SEQUENCE: 23
ggtcagctca tcgcgggatg gg                                           22

<210> SEQ ID NO 24
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 24
cccatcccgc gatgagctga cc                                           22

<210> SEQ ID NO 25
<211> LENGTH: 9
<212> TYPE: DNA
<213> ORGANISM: Artificial sequence
<220> FEATURE:
<223> OTHER INFORMATION: synthetic oligonucleotide

<400> SEQUENCE: 25 gccgccacc                                                           9

<210> SEQ ID NO 26
<211> LENGTH: 33
<212> TYPE: DNA
<213> ORGANISM: Artificial sequence
<220> FEATURE:
<223> OTHER INFORMATION: synthetic oligonucleotide

<400> SEQUENCE: 26
ttactgcaga aggttatgca gcgcgtgaac atg                                33

<210> SEQ ID NO 27
<211> LENGTH: 26
<212> TYPE: DNA
<213> ORGANISM: Artificial sequence
<220> FEATURE:
<223> OTHER INFORMATION: synthetic oligonucleotide

<400> SEQUENCE: 27
agtgagcttt gttttttcct taatcc                                       26

<210> SEQ ID NO 28
<211> LENGTH: 38
<212> TYPE: DNA
<213> ORGANISM: Artificial sequence
<220> FEATURE:
<223> OTHER INFORMATION: synthetic oligonucleotide

<400> SEQUENCE: 28
caagggaatc tagagagaga atgtatggaa gaaaagtg                          38

<210> SEQ ID NO 29
<211> LENGTH: 37
<212> TYPE: DNA
<213> ORGANISM: Artificial sequence
<220> FEATURE:
<223> OTHER INFORMATION: synthetic oligonucleotide

<400> SEQUENCE: 29
acattctctc tctagattcc cttgaacaaa ctcttcc                           37
```

<210> SEQ ID NO 30
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 30
atgacatcca ctttgccttt ctct                                            24

<210> SEQ ID NO 31
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 31
atagaagcct ttgaccaggc                                                 20

<210> SEQ ID NO 32
<211> LENGTH: 39
<212> TYPE: DNA
<213> ORGANISM: Artificial sequence
<220> FEATURE:
<223> OTHER INFORMATION: synthetic oligonucleotide

<400> SEQUENCE: 32
aaaaacaaag ctcactgaca aaactcacac atgcccacc                            39

<210> SEQ ID NO 33
<211> LENGTH: 42
<212> TYPE: DNA
<213> ORGANISM: Artificial sequence
<220> FEATURE:
<223> OTHER INFORMATION: synthetic oligonucleotide

<400> SEQUENCE: 33
gtgtgagttt tgtcagtgag ctttgttttt tccttaatcc ag                        42

<210> SEQ ID NO 34
<211> LENGTH: 37
<212> TYPE: DNA
<213> ORGANISM: Artificial sequence
<220> FEATURE:
<223> OTHER INFORMATION: synthetic oligonucleotide

<400> SEQUENCE: 34
atgcggccgc gccgccacca tggagacaga cacactc                              37

<210> SEQ ID NO 35
<211> LENGTH: 26
<212> TYPE: DNA
<213> ORGANISM: Artificial sequence
<220> FEATURE:
<223> OTHER INFORMATION: synthetic oligonucleotide

<400> SEQUENCE: 35
atctcgagtc atttacccgg agacag                                          26

<210> SEQ ID NO 36
<211> LENGTH: 51
<212> TYPE: DNA
<213> ORGANISM: Artificial sequence
<220> FEATURE:
<223> OTHER INFORMATION: synthetic oligonucleotide

```
<400> SEQUENCE: 36
gtcaaagctt cgcgacgtac ggccgccacc atgcagcgcg tgaacatgat c       51

<210> SEQ ID NO 37
<211> LENGTH: 35
<212> TYPE: DNA
<213> ORGANISM: Artificial sequence
<220> FEATURE:
<223> OTHER INFORMATION: synthetic oligonucleotide

<400> SEQUENCE: 37
ctgtgatgtt cccacagtac ttaccaacct gcgtg                         35

<210> SEQ ID NO 38
<211> LENGTH: 21
<212> TYPE: DNA
<213> ORGANISM: Artificial sequence
<220> FEATURE:
<223> OTHER INFORMATION: synthetic oligonucleotide

<400> SEQUENCE: 38
agtactgtgg gaacatcaca g                                        21

<210> SEQ ID NO 39
<211> LENGTH: 33
<212> TYPE: DNA
<213> ORGANISM: Artificial sequence
<220> FEATURE:
<223> OTHER INFORMATION: synthetic oligonucleotide

<400> SEQUENCE: 39
tgactctaga ttcccttgaa caaactcttc caa                           33

<210> SEQ ID NO 40
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 40
atctacacca tctccatcag cagc                                     24

<210> SEQ ID NO 41
<211> LENGTH: 37
<212> TYPE: DNA
<213> ORGANISM: Artificial sequence
<220> FEATURE:
<223> OTHER INFORMATION: synthetic oligonucleotide

<400> SEQUENCE: 41
aaggcggccg ctcagccttg aaatgtacat gttttgc                       37

<210> SEQ ID NO 42
<211> LENGTH: 18
<212> TYPE: DNA
<213> ORGANISM: Artificial sequence
<220> FEATURE:
<223> OTHER INFORMATION: synthetic oligonucleotide

<400> SEQUENCE: 42
agcgagggag cagcgagg                                            18

<210> SEQ ID NO 43
<211> LENGTH: 21
```

```
<212> TYPE: DNA
<213> ORGANISM: Artificial sequence
<220> FEATURE:
<223> OTHER INFORMATION: synthetic oligonucleotide

<400> SEQUENCE: 43
ggtagttgac atggcggttg g                                              21

<210> SEQ ID NO 44
<211> LENGTH: 34
<212> TYPE: DNA
<213> ORGANISM: Artificial sequence
<220> FEATURE:
<223> OTHER INFORMATION: synthetic oligonucleotide

<400> SEQUENCE: 44
cagcgactta agccaccatg ggctggggga gccg                                34

<210> SEQ ID NO 45
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 45
gtaggttgtg gccagcgtgg                                                20

<210> SEQ ID NO 46
<211> LENGTH: 34
<212> TYPE: DNA
<213> ORGANISM: Artificial sequence
<220> FEATURE:
<223> OTHER INFORMATION: synthetic oligonucleotide

<400> SEQUENCE: 46
ggtaagcttg ccatggagct gaggccctgg ttgc                                34

<210> SEQ ID NO 47
<211> LENGTH: 27
<212> TYPE: DNA
<213> ORGANISM: Artificial sequence
<220> FEATURE:
<223> OTHER INFORMATION: synthetic oligonucleotide

<400> SEQUENCE: 47
gttttcaatc tctaggaccc actcgcc                                        27

<210> SEQ ID NO 48
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 48
gccaggccac atgactactc cgc                                            23

<210> SEQ ID NO 49
<211> LENGTH: 34
<212> TYPE: DNA
<213> ORGANISM: Artificial sequence
<220> FEATURE:
<223> OTHER INFORMATION: synthetic oligonucleotide

<400> SEQUENCE: 49
ggtgaattct cactcaggca ggtgtgaggg cagc                                34
```

<210> SEQ ID NO 50
<211> LENGTH: 53
<212> TYPE: DNA
<213> ORGANISM: Artificial sequence
<220> FEATURE:
<223> OTHER INFORMATION: synthetic oligonucleotide

<400> SEQUENCE: 50
gcgctagccg tacggccgcc accatgaaag tgaggaaata tattacttta tgc        53

<210> SEQ ID NO 51
<211> LENGTH: 29
<212> TYPE: DNA
<213> ORGANISM: Artificial sequence
<220> FEATURE:
<223> OTHER INFORMATION: synthetic oligonucleotide

<400> SEQUENCE: 51
gctattgatc acaaagatct acatcctcc                                    29

<210> SEQ ID NO 52
<211> LENGTH: 29
<212> TYPE: DNA
<213> ORGANISM: Artificial sequence
<220> FEATURE:
<223> OTHER INFORMATION: synthetic oligonucleotide

<400> SEQUENCE: 52
ggaggatgta gatctttgtg atcaatagc                                    29

<210> SEQ ID NO 53
<211> LENGTH: 59
<212> TYPE: DNA
<213> ORGANISM: Artificial sequence
<220> FEATURE:
<223> OTHER INFORMATION: synthetic oligonucleotide

<400> SEQUENCE: 53
gcgaattccg gtccgtcatt gcctagggct cgagagtttt ttaggagtgt ttggatcag    59

<210> SEQ ID NO 54
<211> LENGTH: 21
<212> TYPE: DNA
<213> ORGANISM: Artificial sequence
<220> FEATURE:
<223> OTHER INFORMATION: synthetic oligonucleotide

<400> SEQUENCE: 54
gcatggactc cgatcccaac g                                            21

<210> SEQ ID NO 55
<211> LENGTH: 21
<212> TYPE: DNA
<213> ORGANISM: Artificial sequence
<220> FEATURE:
<223> OTHER INFORMATION: synthetic oligonucleotide

<400> SEQUENCE: 55
cgttgggatc ggagtccatg c                                            21

<210> SEQ ID NO 56
<211> LENGTH: 40
<212> TYPE: DNA
<213> ORGANISM: Artificial sequence
<220> FEATURE:
<223> OTHER INFORMATION: synthetic oligonucleotide -continued

<400> SEQUENCE: 56
ggtaagcttg ccgccaccat gccgaagggg aggcagaaag                    40

<210> SEQ ID NO 57
<211> LENGTH: 33
<212> TYPE: DNA
<213> ORGANISM: Artificial sequence
<220> FEATURE:
<223> OTHER INFORMATION: synthetic oligonucleotide

<400> SEQUENCE: 57
tttgaattct cagttggggg tgatggtgta acc                           33

<210> SEQ ID NO 58
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 58
ggcacctgaa taaccgacgg                                          20

<210> SEQ ID NO 59
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 59
cgtcacgttg atgtccctgc                                          20

<210> SEQ ID NO 60
<211> LENGTH: 19
<212> TYPE: PRT
<213> ORGANISM: Artificial sequence
<220> FEATURE:
<223> OTHER INFORMATION: synthetic peptide

<400> SEQUENCE: 60

Thr Val Phe Leu Asp His Glu Asn Ala Asn Lys Ile Leu Asn Arg Pro
1               5                   10                  15

Lys Arg Cys

<210> SEQ ID NO 61
<211> LENGTH: 2739
<212> TYPE: DNA
<213> ORGANISM: Artificial sequence
<220> FEATURE:
<223> OTHER INFORMATION: synthetic oligonucleotide

<400> SEQUENCE: 61
atgggctggg ggagccgctg ctgctgcccg gacgtttgg acctgctgtg cgtgctggcg      60
ctgctcgggg gctgcctgct ccccgtgtgt cggacgcgcg tctacaccaa ccactgggca    120
gtcaaaatcg ccgggggctt cccggaggcc aaccgtatcg ccagcaagta cggattcatc    180
aacataggac agatagggc cctgaaggac tactaccact tctaccatag caggacgatt    240
aaaaggtcag ttatctcgag cagagggacc cacagtttca tttcaatgga accaaaggtg    300
gaatggatcc aacagcaagt ggtaaaaaag cggacaaaga gggattatga cttcagtcgt    360
gcccagtcta cctatttcaa tgatcccaag tggcccagta tgtggtatat gcactgcagt    420

```
gacaatacac atccctgcca gtctgacatg aatatcgaag gagcctggaa gagaggctac    480 acggaaaga acattgtggt cactatcctg gatgacggaa ttgagagaac ccatccagat    540
ctgatgcaaa actacgatgc tctggcaagt tgcgacgtga atgggaatga cttggaccca    600
atgcctcgtt atgatgcaag caacgagaac aagcatggga ctcgctgtgc tggagaagtg    660
gcagccgctg caaacaattc gcactgcaca gtcggaattg ctttcaacgc aagatcgga     720 ggagtgcgaa tgctggacgg agatgtcacg gacatggttg aagcaaaatc agttagcttc    780
aacccccagc acgtgcacat ttacagcgcc agctggggcc cggatgatga tggcaagact    840
gtggacggac cagcccccct cacccggcaa gcctttgaaa acggcgttag aatggggcgg    900
agaggcctcg gctctgtgtt tgtttgggca tctggaaatg gtggaaggag caaagaccac    960
tgctcctgtg atggctacac caacagcatc tacaccatct ccatcagcag cactgcagaa   1020
agcggaaaga aaccttggta cctggaagag tgttcatcca cgctggccac aacctacagc   1080
agcggggagt cctacgataa gaaaatcatc actacagatc tgaggcagcg ttgcacggac   1140
aaccacactg gacgtcagc ctcagccccc atggctgcag catcattgc gctggccctg    1200 gaagccaatc cgtttctgac ctggagagac gtacagcatg ttattgtcag gacttcccgt   1260
gcgggacatt tgaacgctaa tgactggaaa accaatgctg ctggttttaa ggtgagccat   1320
ctttatggat ttggactgat ggacgcagaa gccatggtga tggaggcaga aagtggacc    1380 accgttcccc ggcagcacgt gtgtgtggag agcacagacc gacaaatcaa gacaatccgc   1440
cctaacagtg cagtgcgctc catctacaaa gcctcaggct gctcagataa ccccaaccgc   1500
catgtcaact acctggagca cgtcgttgtg cgcatcacca tcacccaccc caggagagga   1560
gacctggcca tctacctgac ctcgccctct ggaactaggt ctcagctttt ggccaacagg   1620
ctatttgatc actccatgga aggattcaaa aactgggagt tcatgaccat tcattgctgg   1680
ggagaaagag ctgctggtga ctgggtcctt gaagtttatg atactccctc tcagctaagg   1740
aactttaaga ctccaggtaa attgaaagaa tggtctttgg tcctctacgg cacctccgtg   1800
cagccatatt caccaaccaa tgaatttccg aaagtggaac ggttccgcta tagccgagtt   1860 gaagaccca cagacgacta tggcacagag gattatgcag gtccctgcga ccctgagtgc   1920
agtgaggttg gctgtgacgg gccaggacca gaccactgca atgactgttt gcactactac   1980
tacaagctga aaaacaatac caggatctgt gtctccagct gcccccctgg ccactaccac   2040
gccgacaaga agcgctgcag gaagtgtgcc cccaactgtg agtcctgctt tgggagccat   2100
ggtgaccaat gcatgtcctg caaatatgga tactttctga tgaagaaac caacagctgt   2160 gttactcact gccctgatgg gtcatatcag gataccaaga aaaatctttg ccggaaatgc   2220
agtgaaaact gcaagacatg tactgaattc cataactgta cagaatgtag ggatgggtta   2280
agcctgcagg gatcccggtg ctctgtctcc tgtgaagatg gacggtattt caacggccag   2340
gactgccagc cctgccaccg cttctgcgcc acttgtgctg gggcaggagc tgatgggtgc   2400
attaactgca cagagggcta cttcatggag gatgggagat gcgtgcagag ctgtagtatc   2460
agctattact ttgaccactc ttcagagaat ggatacaaat cctgcaaaaa atgtgatatc   2520
agttgtttga cgtgcaatgg cccaggattc aagaactgta caagctgccc tagtgggtat   2580
ctcttagact taggaatgtg tcaaatggga gccatttgca aggatgcaac ggaagagtcc   2640
tgggcggaag gaggcttctg tatgcttgtg aaaaagaaca atctgtgcca acggaaggtt   2700
cttcaacaac tttgctgcaa acatgtaca tttcaaggc                           2739
```

<210> SEQ ID NO 62

<211> LENGTH: 681
<212> TYPE: DNA
<213> ORGANISM: Homo sapiens
<220> FEATURE:
<223> OTHER INFORMATION: human Fc gamma 1

<400> SEQUENCE: 62

```
gacaaaactc acacatgccc accgtgccca gcacctgaac tcctgggggg accgtcagtc     60
ttcctcttcc cccaaaaacc caaggacacc ctcatgatct cccggacccc tgaggtcaca    120
tgcgtggtgg tggacgtgag ccacgaagac cctgaggtca agttcaactg gtacgtggac    180
ggcgtggagg tgcataatgc caagacaaag ccgcgggagg agcagtacaa cagcacgtac    240
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360
gggcagcccc gagaaccaca ggtgtacacc ctgcccccat cccgggatga gctgaccaag    420
aaccaggtca gcctgacctg cctggtcaaa ggcttctatc ccagcgacat cgccgtggag    480
tgggagagca atgggcagcc ggagaacaac tacaagacca cgcctcccgt gctggactcc    540
gacggctcct tcttcctcta cagcaagctc accgtggaca agagcaggtg gcagcagggg    600
aacgtcttct catgctccgt gatgcatgag gctctgcaca accactacac gcagaagagc    660
ctctccctgt ctccgggtaa a                                              681
```

<210> SEQ ID NO 63
<211> LENGTH: 741
<212> TYPE: DNA
<213> ORGANISM: Artificial sequence
<220> FEATURE:
<223> OTHER INFORMATION: synthetic oligonucleotide

<400> SEQUENCE: 63

```
atggagacag acacactcct gctatgggta ctgctgctct gggttccagg ttccactggt     60
gacaaaactc acacatgccc accgtgccca gctccgaac tgctgggcgg accgtcagtc    120
ttcctcttcc cccaaaaacc caaggacacc ctcatgatct cccggacccc tgaggtcaca    180
tgcgtggtgg tggacgtgag ccacgaagac cctgaggtca agttcaactg gtacgtggac    240
ggcgtggagg tgcataatgc caagacaaag ccgcgggagg agcagtacaa cagcacgtac    300
cgtgtggtca gcgtcctcac cgtcctgcac caggactggc tgaatggcaa ggagtacaag    360
tgcaaggtct ccaacaaagc cctcccagcc cccatcgaga aaaccatctc caaagccaaa    420
gggcagcccc gagaaccaca ggtgtacacc ctgcccccat cccgcgatga gctgaccaag    480
aaccaggtca gcctgacctg cctggtcaaa ggcttctatc ccagcgacat cgccgtggag    540
tgggagagca atgggcagcc ggagaacaac tacaagacca cgcctcccgt gttggactcc    600
gacggctcct tcttcctcta cagcaagctc accgtggaca agagcaggtg gcagcagggg    660
aacgtcttct catgctccgt gatgcatgag gctctgcaca accactacac gcagaagagc    720
ctctccctgt ctccgggtaa a                                              741
```

<210> SEQ ID NO 64
<211> LENGTH: 247
<212> TYPE: PRT
<213> ORGANISM: Artificial sequence
<220> FEATURE:
<223> OTHER INFORMATION: synthetic peptide

<400> SEQUENCE: 64

```
Met Glu Thr Asp Thr Leu Leu Leu Trp Val Leu Leu Leu Trp Val Pro
1               5                   10                  15
```

```
Gly Ser Thr Gly Asp Lys Thr His Thr Cys Pro Pro Cys Pro Ala Pro
            20                  25                  30
Glu Leu Leu Gly Gly Pro Ser Val Phe Leu Phe Pro Pro Lys Pro Lys
        35                  40                  45
Asp Thr Leu Met Ile Ser Arg Thr Pro Glu Val Thr Cys Val Val Val
 50                  55                  60
Asp Val Ser His Glu Asp Pro Glu Val Lys Phe Asn Trp Tyr Val Asp
65                  70                  75                  80
Gly Val Glu Val His Asn Ala Lys Thr Lys Pro Arg Glu Glu Gln Tyr
                85                  90                  95
Asn Ser Thr Tyr Arg Val Val Ser Val Leu Thr Val Leu His Gln Asp
            100                 105                 110
Trp Leu Asn Gly Lys Glu Tyr Lys Cys Lys Val Ser Asn Lys Ala Leu
        115                 120                 125
Pro Ala Pro Ile Glu Lys Thr Ile Ser Lys Ala Lys Gly Gln Pro Arg
130                 135                 140
Glu Pro Gln Val Tyr Thr Leu Pro Pro Ser Arg Asp Glu Leu Thr Lys
145                 150                 155                 160
Asn Gln Val Ser Leu Thr Cys Leu Val Lys Gly Phe Tyr Pro Ser Asp
                165                 170                 175
Ile Ala Val Glu Trp Glu Ser Asn Gly Gln Pro Glu Asn Asn Tyr Lys
            180                 185                 190
Thr Thr Pro Pro Val Leu Asp Ser Asp Gly Ser Phe Phe Leu Tyr Ser
        195                 200                 205
Lys Leu Thr Val Asp Lys Ser Arg Trp Gln Gln Gly Asn Val Phe Ser
210                 215                 220
Cys Ser Val Met His Glu Ala Leu His Asn His Tyr Thr Gln Lys Ser
225                 230                 235                 240
Leu Ser Leu Ser Pro Gly Lys
                245

<210> SEQ ID NO 65
<211> LENGTH: 2064
<212> TYPE: DNA
<213> ORGANISM: Artificial sequence
<220> FEATURE:
<223> OTHER INFORMATION: synthetic oligonucleotide; FIX-Fc

<400> SEQUENCE: 65
atgcagcgcg tgaacatgat catggcagaa tcaccaggcc tcatcaccat ctgcctttta      60
ggatatctac tcagtgctga atgtacagtt tttcttgatc atgaaaacgc caacaaaatt     120
ctgaatcggc caaagaggta taattcaggt aaattggaag agtttgttca agggaatcta     180
gagagagaat gtatggaaga aaagtgtagt tttgaagaag cacgagaagt ttttgaaaac     240
actgaaagaa caactgaatt tggaagcag tatgttgatg agatcagtg tgagtccaat       300 ccatgtttaa atggcggcag ttgcaaggat gacattaatt cctatgaatg ttggtgtccc     360
tttggatttg aaggaaagaa ctgtgaatta gatgtaacat gtaacattaa gaatggcaga     420
tgcgagcagt tttgtaaaaa tagtgctgat aacaaggtgg tttgctcctg tactgaggga     480
tatcgacttg cagaaaacca gaagtcctgt gaaccagcag tgccatttcc atgtggaaga     540
gtttctgttt cacaaacttc taagctcacc cgtgctgaga ctgttttcc tgatgtggac      600 tatgtaaatt ctactgaagc tgaaaccatt ttggataaca tcactcaaag cacccaatca    660
tttaatgact tcactcgggt tgttggtgga agatgccaa accaggtca attcccttgg      720
```

```
caggttgttt tgaatggtaa agttgatgca ttctgtggag gctctatcgt taatgaaaaa    780
tggattgtaa ctgctgccca ctgtgttgaa actggtgtta aaattacagt tgtcgcaggt    840
gaacataata ttgaggagac agaacataca gagcaaaagc gaaatgtgat tcgaattatt    900
cctcaccaca actacaatgc agctattaat aagtacaacc atgacattgc ccttctggaa    960
ctggacgaac ccttagtgct aaacagctac gttacaccta tttgcattgc tgacaaggaa   1020
tacacgaaca tcttcctcaa atttggatct ggctatgtaa gtggctgggg aagagtcttc   1080
cacaaaggga gatcagcttt agttcttcag taccttagag ttccacttgt tgaccgagcc   1140
acatgtcttc gatctacaaa gttcaccatc tataacaaca tgttctgtgc tggcttccat   1200
gaaggaggta gagattcatg tcaaggagat agtgggggac cccatgttac tgaagtggaa   1260
gggaccagtt tcttaactgg aattattagc tggggtgaag agtgtgcaat gaaaggcaaa   1320
tatggaatat ataccaaggt gtcccggtat gtcaactgga ttaaggaaaa aacaaagctc   1380
actgacaaaa ctcacacatg cccaccgtgc ccagctccgg aactcctggg cggaccgtca   1440
gtcttcctct tccccccaaa acccaaggac accctcatga tctcccggac ccctgaggtc   1500
acatgcgtgg tggtggacgt gagccacgaa gaccctgagg tcaagttcaa ctggtacgtg   1560
gacggcgtgg aggtgcataa tgccaagaca aagccgcggg aggagcagta caacagcacg   1620
taccgtgtgg tcagcgtcct caccgtcctg caccaggact ggctgaatgg caaggagtac   1680
aagtgcaagg tctccaacaa agccctccca gcccccatcg agaaaaccat ctccaaagcc   1740
aaagggcagc cccgagaacc acaggtgtac accctgcccc catcccggga tgagctgacc   1800
aagaaccagg tcagcctgac ctgcctggtc aaaggcttct atcccagcga catcgccgtg   1860
gagtgggaga gcaatgggca gccggagaac aactacaaga ccacgcctcc cgtgttggac   1920
tccgacggct ccttcttcct ctacagcaag ctcaccgtgg acaagagcag gtggcagcag   1980
gggaacgtct tctcatgctc cgtgatgcat gaggctctgc acaaccacta cacgcagaag   2040
agcctctccc tgtctccggg taaa                                         2064
```

<210> SEQ ID NO 66
<211> LENGTH: 688
<212> TYPE: PRT
<213> ORGANISM: artificial sequence
<220> FEATURE:
<223> OTHER INFORMATION: synthetic peptide

<400> SEQUENCE: 66

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125
```

-continued

```
Glu Leu Asp Val Thr Cys Asn Ile Lys Asn Gly Arg Cys Glu Gln Phe
    130                 135                 140
Cys Lys Asn Ser Ala Asp Asn Lys Val Val Cys Ser Cys Thr Glu Gly
145                 150                 155                 160
Tyr Arg Leu Ala Glu Asn Gln Lys Ser Cys Glu Pro Ala Val Pro Phe
                165                 170                 175
Pro Cys Gly Arg Val Ser Val Ser Gln Thr Ser Lys Leu Thr Arg Ala
            180                 185                 190
Glu Thr Val Phe Pro Asp Val Asp Tyr Val Asn Ser Thr Glu Ala Glu
        195                 200                 205
Thr Ile Leu Asp Asn Ile Thr Gln Ser Thr Gln Ser Phe Asn Asp Phe
210                 215                 220
Thr Arg Val Val Gly Gly Glu Asp Ala Lys Pro Gly Gln Phe Pro Trp
225                 230                 235                 240
Gln Val Val Leu Asn Gly Lys Val Asp Ala Phe Cys Gly Gly Ser Ile
                245                 250                 255
Val Asn Glu Lys Trp Ile Val Thr Ala Ala His Cys Val Glu Thr Gly
            260                 265                 270
Val Lys Ile Thr Val Val Ala Gly Glu His Asn Ile Glu Glu Thr Glu
        275                 280                 285
His Thr Glu Gln Lys Arg Asn Val Ile Arg Ile Ile Pro His His Asn
        290                 295                 300
Tyr Asn Ala Ala Ile Asn Lys Tyr Asn His Asp Ile Ala Leu Leu Glu
305                 310                 315                 320
Leu Asp Glu Pro Leu Val Leu Asn Ser Tyr Val Thr Pro Ile Cys Ile
                325                 330                 335
Ala Asp Lys Glu Tyr Thr Asn Ile Phe Leu Lys Phe Gly Ser Gly Tyr
            340                 345                 350
Val Ser Gly Trp Gly Arg Val Phe His Lys Gly Arg Ser Ala Leu Val
        355                 360                 365
Leu Gln Tyr Leu Arg Val Pro Leu Val Asp Arg Ala Thr Cys Leu Arg
        370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
            420                 425                 430
Glu Glu Cys Ala Met Lys Gly Lys Tyr Gly Ile Tyr Thr Lys Val Ser
        435                 440                 445
Arg Tyr Val Asn Trp Ile Lys Glu Lys Thr Lys Leu Thr Asp Lys Thr
450                 455                 460
His Thr Cys Pro Pro Cys Pro Ala Pro Glu Leu Leu Gly Gly Pro Ser
465                 470                 475                 480
Val Phe Leu Phe Pro Pro Lys Pro Lys Asp Thr Leu Met Ile Ser Arg
                485                 490                 495
Thr Pro Glu Val Thr Cys Val Val Val Asp Val Ser His Glu Asp Pro
            500                 505                 510
Glu Val Lys Phe Asn Trp Tyr Val Asp Gly Val Glu Val His Asn Ala
        515                 520                 525
Lys Thr Lys Pro Arg Glu Glu Gln Tyr Asn Ser Thr Tyr Arg Val Val
        530                 535                 540
Ser Val Leu Thr Val Leu His Gln Asp Trp Leu Asn Gly Lys Glu Tyr
545                 550                 555                 560
```

| | | | | | | | | | | | |
|---|---|---|---|---|---|---|---|---|---|---|---|
|Lys|Cys|Lys|Val|Ser|Asn|Lys|Ala|Leu|Pro|Ala|Pro|Ile|Glu|Lys|Thr|
| | | | |565| | | |570| | | |575| | | |
|Ile|Ser|Lys|Ala|Lys|Gly|Gln|Pro|Arg|Glu|Pro|Gln|Val|Tyr|Thr|Leu|
| | | | |580| | | |585| | | |590| | | |
|Pro|Pro|Ser|Arg|Asp|Glu|Leu|Thr|Lys|Asn|Gln|Val|Ser|Leu|Thr|Cys|
| | | | |595| | | |600| | | |605| | | |
|Leu|Val|Lys|Gly|Phe|Tyr|Pro|Ser|Asp|Ile|Ala|Val|Glu|Trp|Glu|Ser|
| | | | |610| | | |615| | | |620| | | |
|Asn|Gly|Gln|Pro|Glu|Asn|Asn|Tyr|Lys|Thr|Thr|Pro|Pro|Val|Leu|Asp|
| | | |625| | | | |630| | | |635| | | |640|
|Ser|Asp|Gly|Ser|Phe|Phe|Leu|Tyr|Ser|Lys|Leu|Thr|Val|Asp|Lys|Ser|
| | | | |645| | | |650| | | |655| | | |
|Arg|Trp|Gln|Gln|Gly|Asn|Val|Phe|Ser|Cys|Ser|Val|Met|His|Glu|Ala|
| | | | |660| | | |665| | | |670| | | |
|Leu|His|Asn|His|Tyr|Thr|Gln|Lys|Ser|Leu|Ser|Leu|Ser|Pro|Gly|Lys|
| | | | |675| | | |680| | | |685| | | |

<210> SEQ ID NO 67
<211> LENGTH: 741
<212> TYPE: DNA
<213> ORGANISM: Artificial sequence
<220> FEATURE:
<223> OTHER INFORMATION: synthetic oligonucleotide

<400> SEQUENCE: 67

```
atggagacag acacactcct gctatgggta ctgctgctct ggttccagg ttccactggt      60
gacaaaactc acacatgccc accgtgccca gcacctgaac tcctgggagg accgtcagtc    120
ttcctcttcc ccccaaaacc caaggacacc ctcatgatct cccggacccc tgaggtcaca    180
tgcgtggtgg tggacgtgag ccacgaagac cctgaggtca agttcaactg gtacgtggac    240
ggcgtggagg tgcataatgc caagacaaag ccgcgggagg agcagtacaa cagcacgtac    300
cgtgtggtca gcgtcctcac cgtcctgcac caggactggc tgaatggcaa ggagtacaag    360
tgcaaggtct ccaacaaagc cctcccagcc cccatcgaga aaaccatctc caaagccaaa    420
gggcagcccc gagaaccaca ggtgtacacc ctgcccccat cccgcgatga gctgaccaag    480
aaccaggtca gcctgacctg cctggtcaaa ggcttctatc ccagcgacat cgccgtggag    540
tgggagagca atgggcagcc ggagaacaac tacaagacca cgcctcccgt gttggactcc    600
gacggctcct tcttcctcta cagcaagctc accgtggaca agagcaggtg gcagcagggg    660
aacgtcttct catgctccgt gatgcatgag gctctgcaca accactacac gcagaagagc    720
ctctccctgt ctccgggtaa a                                              741
```

<210> SEQ ID NO 68
<211> LENGTH: 2363
<212> TYPE: DNA
<213> ORGANISM: Artificial sequence
<220> FEATURE:
<223> OTHER INFORMATION: synthetic oligonucleotide; FIX-Fc

<400> SEQUENCE: 68

```
atgcagcgcg tgaacatgat catggcagaa tcaccaggcc tcatcaccat ctgccttta      60
ggatatctac tcagtgctga atgtacaggt ttgtttcctt ttttaaaata cattgagtat    120
gcttgccttt tagatataga aatatctgat gctgtcttct tcactaaatt ttgattacat    180
```

```
gatttgacag caatattgaa gagtctaaca gccagcacgc aggttggtaa gtactgtggg       240
aacatcacag attttggctc catgccctaa agagaaattg gctttcagat tatttggatt       300
aaaaacaaag actttcttaa gagatgtaaa attttcatga tgttttcttt tttgctaaaa       360
ctaaagaatt attcttttac atttcagttt ttcttgatca tgaaaacgcc aacaaaattc       420
tgaatcggcc aaagaggtat aattcaggta aattggaaga gtttgttcaa gggaatctag       480
agagagaatg tatggaagaa aagtgtagtt ttgaagaagc acgagaagtt tttgaaaaca       540
ctgaaagaac aactgaattt tggaagcagt atgttgatgg agatcagtgt gagtccaatc       600 catgttttaaa tggcggcagt tgcaaggatg acattaattc ctatgaatgt tggtgtccct       660
ttggatttga aggaaagaac tgtgaattag atgtaacatg taacattaag aatggcagat       720
gcgagcagtt ttgtaaaaat agtgctgata caaggtggt ttgctcctgt actgagggat        780
atcgacttgc agaaaccag aagtcctgtg aaccagcagt gccatttcca tgtggaagag        840
tttctgtttc acaaacttct aagctcaccc gtgctgagac tgttttttcct gatgtggact       900 atgtaaattc tactgaagct gaaaccattt tggataacat cactcaaagc acccaatcat       960
ttaatgactt cactcgggtt gttggtggag aagatgccaa accaggtcaa ttcccttggc      1020
aggttgtttt gaatggtaaa gttgatgcat tctgtggagg ctctatcgtt aatgaaaaat      1080
ggattgtaac tgctgcccac tgtgttgaaa ctggtgttaa aattacagtt gtcgcaggtg      1140
aacataatat tgaggagaca gaacatacag agcaaaagcg aaatgtgatt cgaattattc      1200
ctcaccacaa ctacaatgca gctattaata agtacaacca tgacattgcc cttctggaac      1260
tggacgaacc cttagtgcta aacagctacg ttacacctat ttgcattgct gacaaggaat      1320
acacgaacat cttcctcaaa tttggatctg gctatgtaag tggctgggga agagtcttcc      1380
acaaagggag atcagctta gttcttcagt accttagagt tccacttgtt gaccgagcca       1440
catgtcttcg atctacaaag ttcaccatct ataacaacat gttctgtgct ggcttccatg      1500
aaggaggtag agattcatgt caaggagata gtgggggacc ccatgttact gaagtggaag      1560
ggaccagttt cttaactgga attattagct ggggtgaaga gtgtgcaatg aaaggcaaat      1620
atggaatata taccaaggtg tcccggtatg tcaactggat taaggaaaaa acaaagctca      1680
ctgacaaaac tcacacatgc ccaccgtgcc cagctccgga actcctgggc ggaccgtcag      1740
tcttcctctt ccccccaaaa cccaaggaca ccctcatgat ctcccggacc cctgaggtca      1800
catgcgtggt ggtggacgtg agccacgaag accctgaggt caagttcaac tggtacgtgg      1860
acggcgtgga ggtgcataat gccaagacaa agccgcggga ggagcagtac aacagcacgt      1920
accgtgtggt cagcgtcctc accgtcctgc accaggactg gctgaatggc aaggagtaca      1980
agtgcaaggt ctccaacaaa gccctcccag cccccatcga gaaaaccatc tccaaagcca      2040
aagggcagcc ccgagaacca caggtgtaca ccctgccccc atcccgggat gagctgacca      2100
agaaccaggt cagcctgacc tgcctggtca aaggcttcta tcccagcgac atcgccgtgg      2160
agtgggagag caatgggcag ccggagaaca actacaagac cacgcctccc gtgttggact      2220
ccgacggctc cttcttcctc tacagcaagc tcaccgtgga caagagcagg tggcagcagg      2280
ggaacgtctt ctcatgctcc gtgatgcatg aggctctgca caaccactac acgcagaaga      2340
gcctctccct gtctccgggt aaa                                              2363
```